(12) United States Patent
Sparks

(10) Patent No.: US 7,883,903 B2
(45) Date of Patent: Feb. 8, 2011

(54) DENDRITIC CHEMILUMINESCENT SUBSTRATES

(75) Inventor: Alison L. Sparks, North Andover, MA (US)

(73) Assignee: Applied Biosystems, LLC

( * ) Notice: Subject to any disclaimer, the term of this patent is extended or adjusted under 35 U.S.C. 154(b) by 663 days.

(21) Appl. No.: 11/730,715

(22) Filed: Apr. 3, 2007

(65) Prior Publication Data
US 2007/0184491 A1   Aug. 9, 2007

Related U.S. Application Data

(62) Division of application No. 10/038,626, filed on Jan. 8, 2002, now Pat. No. 7,214,546.

(60) Provisional application No. 60/259,870, filed on Jan. 8, 2001, provisional application No. 60/286,383, filed on Apr. 26, 2001.

(51) Int. Cl.
*G01N 33/533* (2006.01)
*G01N 33/544* (2006.01)
*G01N 33/545* (2006.01)
*G01N 21/76* (2006.01)

(52) U.S. Cl. ............ 436/546; 436/172; 436/528; 436/531; 436/805

(58) Field of Classification Search ............ None
See application file for complete search history.

(56) References Cited

U.S. PATENT DOCUMENTS

| | | |
|---|---|---|
| 4,978,614 A | 12/1990 | Bronstein |
| 5,112,960 A | 5/1992 | Bronstein et al. |
| 5,145,772 A | 9/1992 | Voyta et al. |
| 5,338,532 A | 8/1994 | Tomalia et al. |
| 5,443,953 A | 8/1995 | Hansen et al. |
| 5,482,698 A | 1/1996 | Griffiths |
| 5,527,524 A | 6/1996 | Tomalia et al. |
| 5,538,847 A | 7/1996 | Bronstein et al. |
| 5,582,980 A | 12/1996 | Bronstein et al. |
| 5,635,603 A | 6/1997 | Hansen et al. |
| 5,714,166 A | 2/1998 | Tomalia et al. |
| RE36,536 E | 1/2000 | Bronstein |
| 6,083,708 A | 7/2000 | Singh et al. |
| 6,440,405 B1 | 8/2002 | Cooper et al. |
| 7,097,856 B2 * | 8/2006 | Frechet et al. ............ 424/486 |

FOREIGN PATENT DOCUMENTS

WO    WO 95/01341    1/1995

OTHER PUBLICATIONS

Adamczyk et al., "Tracemer™ Signal Generators: An Arborescent Approach to the Incorporation of Multiple Chemiluminescent Labels," Bioorganic & Medicinal Chemistry Letters, vol. 8, pp. 3595-3598 (1998).

(Continued)

*Primary Examiner*—Shafiqul Haq

(57) ABSTRACT

Chemiluminescent substrate delivery systems comprising a conjugate a dendrimer and at least one chemiluminescent substrate are provided. The substrate delivery systems can also include a chemiluminescence enhancer. The dendrimer/chemiluminescent substrate conjugates can be used in kits including an enzyme capable of activating the chemiluminescent substrate to produce a peroxygenated intermediate that decomposes to produce light. The dendrimer/chemiluminescent substrate conjugates can be used in assays to detect the presence of an analyte (e.g., an enzyme, an antibody, an antigen or a nucleic acid) in a sample.

15 Claims, 52 Drawing Sheets

OTHER PUBLICATIONS

Arakawa et al., "Chemiluminescence Enzyme Immunoassay for Thyroxin with Use of Glucose Oxidase and a Bis(2,4,6-trichlorophenyl)oxalate-Fluorescent dye System," Clin. Chem., 31, 3, pp. 430-434 (1985).

Arakawa et al., "Chemiluminescence Enzyme Immunoassay of Cortisol Using Peroxidase as Label," Analytical Biochemistry, 97, pp. 248-254 (1979) (cited as vol. 79 on p. 8 of the specification).

Barnard et al., "Recent Advances in Chemiluminescence Immunoassay," Bioluminescence and Chemiluminescence: Instruments and Applications, Chapter 7, vol. I, K. Van Dyke (ed.), CRC Press, Inc., Boca Raton, Florida, pp. 151-183 (1985).

D. Simons, "Spacers, Probability and Yields," Bioconjugate Chemistry, vol. 10, pp. 3-8 (1999).

Kricka et al., "Luminescent Immunoassays," Clinical and Biochemical Luminescence, L.J. Kricka et al., (eds.), Chapter 8, vol. 12, Marcel Dekker, Inc., New York, pp. 153-178 (1982).

Lehmann et al., "Dendrimers Consisting of Stilbene or Distyrylbenzene Building Blocks synthesis and Stability," Tetrahedron, vol. 55, pp. 13377-13394 (1999).

Mayer et al., "Luminescent Labels—More than Just an Alternative to Radioisotopes?," Angewandte Chem. Int. Ed. Engl., vol. 33, pp. 1044-1073 (1994).

McCarpra et al., "Selected Chemical Reactions that Produce Light," Bioluminescence and Chemiluminescence: Instruments and Applications, Chapter 2, vol. I, K. Van Dyke (ed.), CRC Press, Inc., Boca Raton, Florida, pp. 9-42 (1985).

Newkome et al., "Dendritic Molecules: Concepts, Syntheses, Perspectives," G.R. Newkome et al. (eds.), VCH Publishers, Inc., New York (1996).

Schroeder et al., "Chemiluminescence Yields and Detection Limits of Some Isoluminol Derivatives in Various Oxidation Systems," Analytical Chemistry, 50, 8, pp. 1114-1120 (1978).

* cited by examiner

DENDRITIC CHEMILUMINESCENT SUBSTRATES

CROSS-REFERENCES TO RELATED APPLICATIONS

This application is a divisional of U.S. application Ser. No. 10/038,626, filed Jan. 8, 2002 now U.S. Pat. No. 7,214,546, which claims the benefit of U.S. Provisional Application No. 60/259,870, filed Jan. 8, 2001 and U.S. Provisional Application No. 60/286,383, filed Apr. 26, 2001.

BACKGROUND OF THE INVENTION

1. Field of the Invention

The present invention concerns dendritic polymer chemiluminescent substrate conjugates; synthesis of dendritic polymer chemiluminescent substrate conjugates; compositions containing dendritic polymer chemiluminescent substrate conjugates; and methods of using dendritic polymer chemiluminescent substrate conjugates. The invention also concerns the use of enhancer substances in combination with the dendritic polymer chemiluminescent substrate conjugates. The dendritic polymer chemiluminescent substrate conjugates and enhancer dendritic polymer chemiluminescent substrate conjugates, which amplify the detectable chemiluminescent signal by coupling multiple (i.e., from 3 to 3072) enzyme activable chemiluminescent substrates, are useful in detecting the presence or determining the concentration of chemical or biological substances in immunoassays, chemical assays and nucleic acid probe assays, and in chemical/physical probe procedures for studying the microstructures of macromolecules, including synthetic polymers, proteins, nucleic acids and the like.

2. Background of the Technology

Dendritic polymers (otherwise known as "dendrimers") are uniform polymers, variously referred to in the literature as hyperbranched dendrimers, arborols, fractal polymers and starburst dendrimers, having a central core, an interior dendritic (hyperbranched) structure and an exterior surface with end groups. These polymers differ from the classical linear polymers both in form and function. Linear polymer chemistry results from chaotic, uncontrolled processes that yield a distribution of product species from microscopic to macroscopic size. The molecular linearity of the polymers produces a heavily entangled macromolecular population that defines macroscopic behavior such as sharply increasing viscosity with increased molecular weight, mediocre chemical reactivity due to hidden sites in random coils and variable or mediocre solubility. In contrast, dendrimer chemistry constructs macromolecules with tight control of size, shape topology, flexibility and surface groups. In what is known as divergent synthesis, these macromolecules start by reacting an initiator core in high-yield iterative reaction sequences to build symmetrical branches radiating from the core with well-defined surface groups. Alternatively, in what is known as convergent synthesis, dendritic wedges are constructed from the periphery inwards towards a focal point and then several dendritic wedges are coupled at the focal points with a polyfunctional core. Dendritic syntheses form concentric layers, known as generations, with each generation doubling the molecular mass and the number of reactive groups at the branch ends so that the end generation dendrimer is a highly pure, uniform monodisperse macromolecule that solubilizes readily over a range of conditions. For the reasons discussed below, dendrimer molecular weights range from 300 to 700,000 daltons and the number of surface groups (e.g., reactive sites for coupling) range from 3 to 3072.

As dendrimers grow with each generation, the steric constraints from congestion of the branches force the polymer shape to change from a starfish-shaped molecule to a globular molecule. For example, with starburst polyamidoamine ("PAMAM") dendrimers, generations 0-3 are dome-shaped, generation 4 is a transition generation with an oblate spheriod shape, and generations 5 and greater are symmetrically spherical with a hollow interior and a surface skin. This change of shape, from domes to spheres, with increasing size (caused by increasing surface congestion at the branch ends) is a general feature of dendritic polymers.

Dendritic growth, shape and topology are controlled by the core, the interior branch structure and the surface groups. Dendrimers expand symmetrically in a way that maintains a constant terminal surface group area. For example, with starburst dendrimers the surface group —$CO_2Me$ requires 93 $A^2$/group whereas the surface group —$NH_2$ requires 150 $A^2$/group. Terminal groups with greater steric bulk, such as $NH_2$, promote greater core hollowness by surface steric interaction as observed with the PAMAMs. In contrast, polyether starburst dendrimers become congested within 3 generations with very little internal cavity. In general, dendritic growth becomes self-limiting as steric congestion of the surface reactive sites precludes further chemical modification; for PAMAM starburst dendrimers this occurs at generations 9-10.

As discussed herein, dendritic surfaces can have from 3 to 3072 end groups available for surface chemistry; the number of end groups depending on the type of dendrimer structure (which defines steric congestion) and the dendrimer generation. Amino ($NH_2$) terminated dendrimers react with, e.g., Michael acceptors ($CH_2$=$CHCO_2R$), α-haloesters, epoxides, aziridines, activated carboxylic acids, acid chlorides, benzyl halides, carbonates and aldehydes. Hydroxyl (OH) terminated dendrimers react with, e.g., halosulfonic esters, activated carboxylic acids and acid chlorides. Ester and acid ($CO_2R$, $CO_2H$) terminated dendrimers react with, e.g., amines and halide terminated dendrimers react with, e.g., amines and alkoxide and thioalkoxide anions. Other reactive surface groups include carboxyhalide, imino, imido, alkylamino, dialkylamino, alkylarylamino, cyano, sulfonic esters, dithiopyridyl and sulfhydryl, among others. Chemical reactions on the dendrimer surface usually occur as readily as with single organic molecules, with high specificity and high yields, as long as there is no steric congestion on the surface. Structures of commercially available dendrimers, which include the Starburst PAMAM dendrimers ($NH_2$-terminated, OH-terminated and $CO_2R$-terminated) and Astramol PEI dendrimers ($NH_2$-terminated), which are shown in FIGS. 1A to 1D are available from Aldrich Chemical Co., Dendritech Inc. and DSM Fine Chemicals. In addition, many other dendritic polymers with reactive surface groups have been synthesized and reported in the literature (for a review, see, for example, "Dendritic Molecules: Concepts, Syntheses, Perspectives," G. R. Newkome, C. N. Moorefield, F. Vogtle, VCH Publishers, Inc. New York (1996) and references cited at the end of this application).

In recent years, it has been found that the size, shape and properties of dendritic polymers can be molecularly tailored to meet specialized end uses. Dendritic polymers thus have significant advantages which can provide a means for the delivery of high concentrations of carried material per unit of polymer, controlled delivery, targeted delivery and/or multiple species delivery or use.

U.S. Pat. Nos. 5,338,532; 5,527,524 and 5,714,166 disclose dense star polymers or starburst polymers associated with a variety of materials, including drugs, toxins, metal ions, radionuclides, signal generators, signal reflectors, chelated metal, signal absorbers, antibodies, hormones, biological response modifiers, diagnostic opacifiers, fluorescent moieties and scavenging agents; processes for preparing the conjugates; compositions containing the conjugates; and methods of using the conjugates.

U.S. Pat. No. 5,482,698 discloses methods for detecting or treating lesions that includes a polymer comprising multiple avidin or biotin binding sites; adding a detection or therapeutic agent to the avidin or biotin; and detecting or treating the lesion.

U.S. Pat. Nos. 5,443,953 and 5,635,603 disclose a soluble immunoconjugate that includes a glycosylated antibody fragment, and an intermediate conjugate comprising a polymer carrier having at least one free amine group and a detectable label molecule covalently bound to the polymer carrier.

None of the references cited above disclose the association of dendritic polymers with chemiluminescent substrates.

1,2-dioxetane enzyme substrates have been well established as highly efficient chemiluminescent reporter molecules for use in enzyme assays of a wide variety of types. These assays provide a preferred alternative to conventional assays that rely on radioisotopes, fluorophores, complicated color shifting, secondary reactions and the like. Dioxetanes developed for this purpose include those disclosed in U.S. Pat. Nos. 4,978,614; 5,112,960; 5,538,847 and 5,582,980, as well as U.S. application Ser. No. 09/362,047 (pending). U.S. Pat. No. 4,978,614 discloses, among others, 3-(2'-spiroadamantane)4-methoxy-4-(3"-phosphoryloxy)phenyl-1,2-dioxetane, which is commercially available from Applied Biosystems under the trade name AMPPD®, which is a registered trademark of PE Corporation (NY). U.S. Pat. Nos. 5,112,960; 5,538,847 and 5,582,980 disclose similar compounds, wherein the adamantyl stabilizing ring is substituted, at either bridgehead position, with a variety of substituents, including hydroxy, halogen, and the like, which convert the otherwise static or passive adamantyl stabilizing group into an active group involved in the kinetics of decomposition of the dioxetane ring. Compounds of this type give a faster and stronger signal than AMPPD® in many applications. CSPD®, which is a registered trademark of PE Corporation (NY), is a second-generation dioxetane with a chlorine substituent on the adamantyl group. This material is also available from Applied Biosystems. CSPD® gives improved light intensity and detection sensitivity. U.S. application Ser. No. 09/362,047 discloses enzymatically cleavable chemiluminescent 1,2-dioxetanes that emit in wavelengths close to the red or green end of the visible spectrum. Each of the patents and applications cited in this paragraph are incorporated herein by reference in their entirety.

Reactions that produce chemiluminescence exemplify yet another instance in which the medium, although not the message, can determine the intensity of the message transmitted. Chemiluminescent compounds that, upon decomposition in substances such as moderately polar or polar aprotic organic solvents, e.g., n-butanol, acetonitrile, dimethylsulfoxide or dimethylformamide, produce fluorophores that in turn emit light of adequate intensity for easy detection and quantitation, will produce light of considerably lessened intensity when decomposed in a polar protic environment, and especially in aqueous media. But since all biological systems are aqueous—indeed, humans are approximately 97% water—the need to enhance the intensity of light produced by chemiluminescent labels or substrates in immunoassays, nucleic acid probe assays, chemical/physical probe techniques and other bioassays is obvious. One way to provide such enhancement is to use expensive optical or electronic equipment: single photon counters, luminometers, scintillation counters, etc.

Although dioxetanes have been particularly developed for enhanced sensitivity in assays for the presence of analytes in concentrations as low as $10^{-12}$ M, in certain applications, dioxetanes are used in conjunction with enhancers to detect analytes in concentrations of $10^{-12}$ M or lower. These enhancement agents, which include natural and synthetic water-soluble macromolecules, are disclosed in detail in U.S. Pat. No. 5,145,772. Preferred enhancement agents include water-soluble polymeric quaternary ammonium, phosphonium or sulfonium salts, and copolymers and/or mixtures thereof, such as poly(vinylbenzyltrimethylammonium chloride) (TMQ), poly(vinylbenzyltributylammonium chloride) (TBQ) and poly(vinylbenzyldimethylbenzylammonium chloride) (BDMQ).

These enhancement agents improve the chemiluminescent signal of the dioxetane reporter molecules, apparently by providing a hydrophobic environment in which the dioxetane is sequestered. Water, unavoidable in most assays due to the use of body fluids, is a natural "quencher" of the dioxetane chemiluminescence. The enhancement molecules apparently exclude water from the microenvironment in which the dioxetane molecules, or at least the excited state emitter species reside, resulting in enhanced chemiluminescence. Other effects associated with the enhancer-dioxetane interaction could also contribute to the chemiluminescence enhancement.

In addition to dioxetane, luminol derivatives, acridinium esters, acridinium sulfonylamides and luciferin have been employed as chemiluminescent labels in bioassays (Schroeder et al., Anal. Chem., 50, 1114 (1978); Arakawa et al., Anal. Biochem., 79, 248 (1979); and Arakawa et al., Clin. Chem., 31, 430 (1985). For reviews, see: Kricka et al., Clinical and Biochemical Luminescence, L. J. Kricka and T. J. N. Carter (Eds.), Chapter 8, Marcel Dekker, Inc., New York (1982); Kricka, Ligand-Binder Assays, Chapter 7, Marcel Dekker, Inc., New York, (1985); McCapra et al., Bioluminescence and Chemiluminescence: Instruments and Applications, Vol. I, K. Van Dyke (Ed.), CRC Press, Inc., Boca Raton, Fla. (1985), Chapter 2 (note, in particular, the section on dioxetanes, page 13); and Barnard et al., Ibid, Ch. 7). The enzyme labels have been detected by color or fluorescence development techniques. More recently, chemiluminescent enzyme immunoassays have been based on peroxidase conjugates assayed with luminol/hydrogen peroxide, pyrogallol/hydrogen peroxide, Pholas dactylus luciferin, or luminol under alkaline conditions (Kricka et al., Clinical and Biochemical Luminescence, Chapter 8, L. J. Kricka and T. J. N. Carter (Eds.), Marcel Dekker, Inc., New York (1982)).

By way of background, the enzymatically-activated chemiluminescent substrates are used as reporter molecules by acting as substrates for enzymes which cleave an enzyme-labile group thereon. Thus, the enzyme (e.g., alkaline phosphatase) can be covalently linked or otherwise complexed with either an antigen or antibody, in conventional antigen/antibody ligand binding assays, or a nucleic acid probe in nucleic acid assays. The enzyme-bearing antigen or antibody, or nucleic acid probe, is then admixed with the analyte suspected of containing the target antigen, or nucleic acid sequence, under conditions which permit complexing or hybridization between the antigen/antibody or probe/nucleic acid sequence. After washing away or separating off all non-complexed or nonhybridized material, the chemiluminescent substrate is added. If the suspected analyte is present, the enzyme will cleave the enzyme-labile group chemiluminescent substrate, yielding an intermediate that decomposes. The decomposition event is the light-releasing event.

To detect analytes in extremely low concentrations (below, e.g., about $10^{-12}$ M) it is desirable to improve the intensity of the signal of the chemiluminescent substrate reporter molecule, and it is simultaneously desirable to avoid increasing the background noise due to nonenzymatically-induced light release, so as to improve the overall sensitivity of the assay. Thus, further improvements in the use of chemiluminescent substrates are sought.

All patents and literature that are cited in this disclosure are incorporated herein by reference.

SUMMARY OF THE INVENTION

It is an object of the invention to improve the performance of chemiluminescent substrates, including improving the machine readability, sensitivity and performance aspects of the assays, which, in turn, are dependent on the signal released by the chemiluminescent reporter.

It is another object of the invention to improve the intensity and resolution of the signal of the chemiluminescent substrates, and to simultaneously avoid increasing the background noise due to nonenzymatically-induced light release, so as to improve the overall sensitivity of the assay in order to automate clinical assays and to provide for high throughput screening on high density arrays (microarrays).

The above goals are met by a new class of dendritic polymer chemiluminescent substrates, in which the light signal is amplified by coupling one or more enzyme-activatable chemiluminescent substrates to a dendritic polymer. Signal resolution may also improve due to the frictional drag of the high molecular weight dendritic backbone, i.e., slowed molecular diffusion due to increased molecular size, shape, branching and/or cumulative charge effects, which would confine light emission to the region of substrate activation by an enzyme label.

The chemiluminescent substrates according to the invention can be further enhanced by linking multiple substrate reporter molecules to an enhancing region of the dendritic polymer. In this manner, more efficient sequestration of the substrate from aqueous quenching can be realized. Once the substrate is generated, the incipient reporter can fold into the proximate hydrophobic enhancing region of the dendritic polymer for efficient enhanced chemiluminescence. The enhanced chemiluminescent signal results in increased detection sensitivity.

In accordance with the above objects, the invention provides improvements in the detectability of electromagnetic (e.g., optically detectable) energy released by the decomposition of the chemiluminescent substrates in aqueous and mixed media. In particular, the invention provides means for enhanced detection of electromagnetic (e.g., optically detectable) energy released by the decomposition of chemiluminescent substrates used to detect the presence or determine the concentration or structure of a substance in an aqueous and mixed sample. The invention further provides improvements in the detectability of electromagnetic (e.g., optically detectable) energy released by the decomposition of chemiluminescent substrates used to detect the presence or determine the concentration of chemical or biological substances by art-recognized immunoassay, chemical assay or nucleic acid probe assay techniques. The invention also provides improvements in the detectability of electromagnetic (e.g., optically detectable) energy released by the decomposition of chemiluminescent substrates for studying molecular structures or microstructures.

The invention also provides methods of preparing dendritic polymer chemiluminescent substrates and intermediates therefor. For example, a first process for preparing a conjugate of a dendritic polymer and a chemiluminescent substrate comprises reacting the dendritic polymer with the chemiluminescent substrate in a suitable solvent at a temperature which facilitates the association of the chemiluminescent substrate and the dendritic polymer. Thus, the dendritic surface can be modified by coupling with molecules, such as dioxetanes, luminols, isoluminols, acridinium esters, acridinium sulfonylamides and other luciferins, that have an appropriate reactive site on a linker moiety. A more complete discussion of the process is provided below.

The present invention is thus directed to dendritic polymer chemiluminescent substrate conjugates, processes for preparing the conjugates, compositions containing the conjugates and methods of using the conjugates and compositions.

These and other objects, as well as the nature, scope and utilization of this invention, will become readily apparent to those skilled in the art from the following description, and drawings.

BRIEF DESCRIPTION OF THE DRAWINGS

The present invention may be better understood with reference to the accompanying drawings in which:

FIGS. 1A-1D show the structures of a number of commercially available dendrimers wherein: FIG. 1A shows a polyamidoamine (PAMAM) dendrimer with $NH_2$ surface groups; FIG. 1B shows a polyamidoamine (PAMAM) dendrimer with carboxylic acid surface groups; FIG. 1C shows a polyamidoamine (PAMAM) dendrimer with hydroxyl surface groups; and FIG. 1D shows a polypropyleneimine (PEI) dendrimer with $NH_2$ surface groups;

FIGS. 4A-4F show the synthesis scheme for the dendritic polymer conjugates shown in FIGS. 3A-3L wherein: FIG. 4A corresponds to FIG. 3A and FIG. 3G; FIG. 4B corresponds to FIG. 3B and FIG. 3H; FIG. 4C corresponds to FIG. 3C and FIG. 3I; FIG. 4D corresponds to FIG. 3D and FIG. 3J; FIG. 4E corresponds to FIG. 3E and FIG. 3K; and FIG. 4F corresponds to FIG. 3F and FIG. 3L;

The above figures are merely illustrative and are not to be construed as limiting the scope of the invention.

DETAILED DESCRIPTION OF THE INVENTION

Enzymatic assay design provides significant signal amplification by enzymatic turnover of substrate to generate a signal with increased detection sensitivity. The enzyme substrates are usually colorimetric, fluorimetric or chemiluminescent. In general, chemiluminescent enzyme substrates provide a wider dynamic range of detection as well as increased sensitivity, due to lower intrinsic noise (such as light scattering and autofluorescence), and higher intensity signal output. The instrumentation for detecting chemiluminescent output is also simpler than that required for fluorescence detection, since no excitation source is needed. Examples of chemiluminescent substrates include dioxetanes (activated by hydrolytic enzymes such as esterases, alkaline phosphatases and glycosidases such as β-galactosidase and β-glucuronidase), and luminols, isoluminols, acridinium esters, acridinium sulfonylamides and luciferins (activated by oxidative enzymes such as horseradish peroxidase, glucose or galactose oxidase and luciferase). These substrates are enzyme-activated to produce destabilized peroxygenated intermediates that decompose with light emission. Measurement of the resulting chemiluminescent signal allows detection of enzyme labels in immunoassay, reporter gene assay, DNA probe assay and array formats.

Figure 1A:
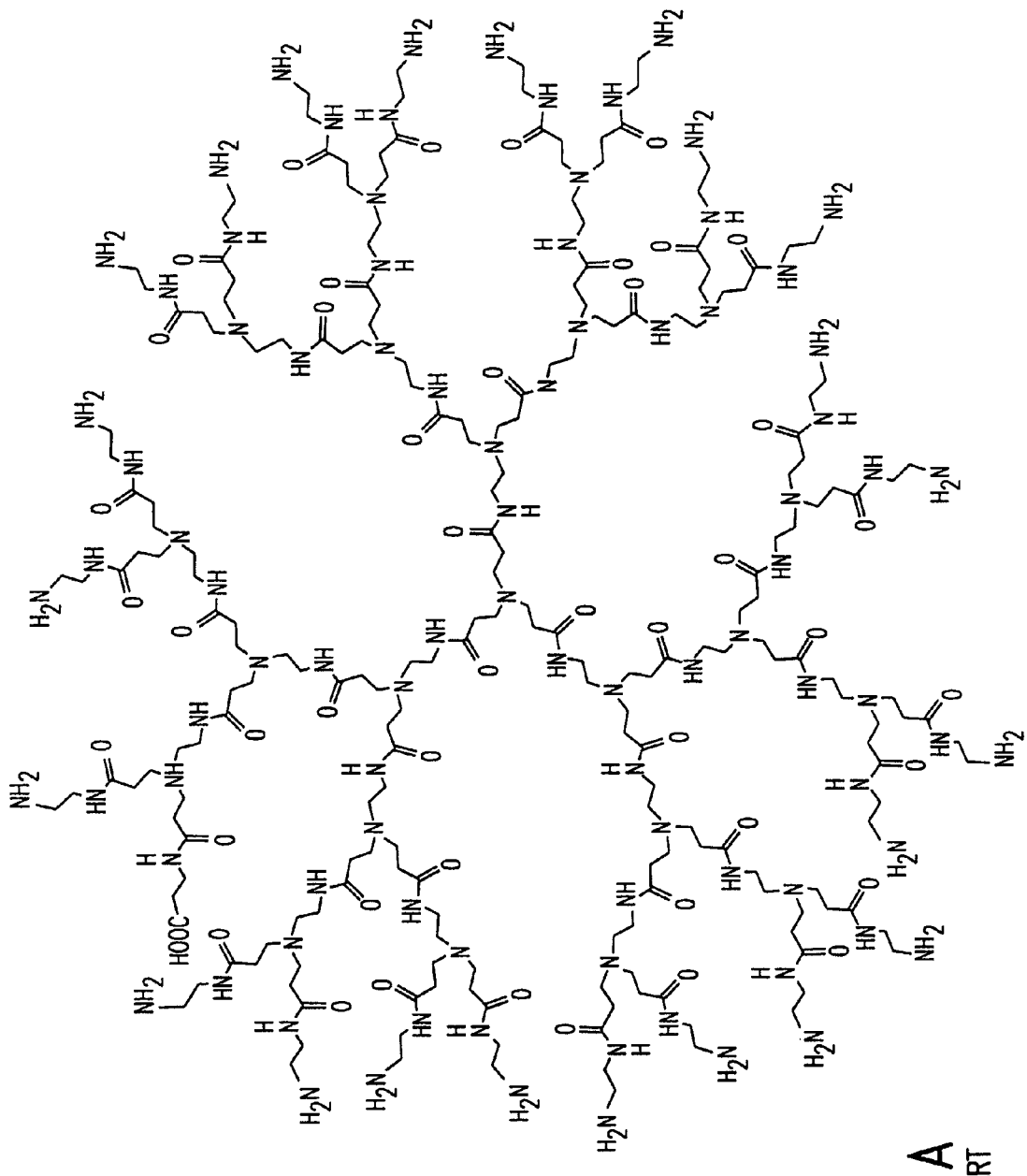
Figure 1B:
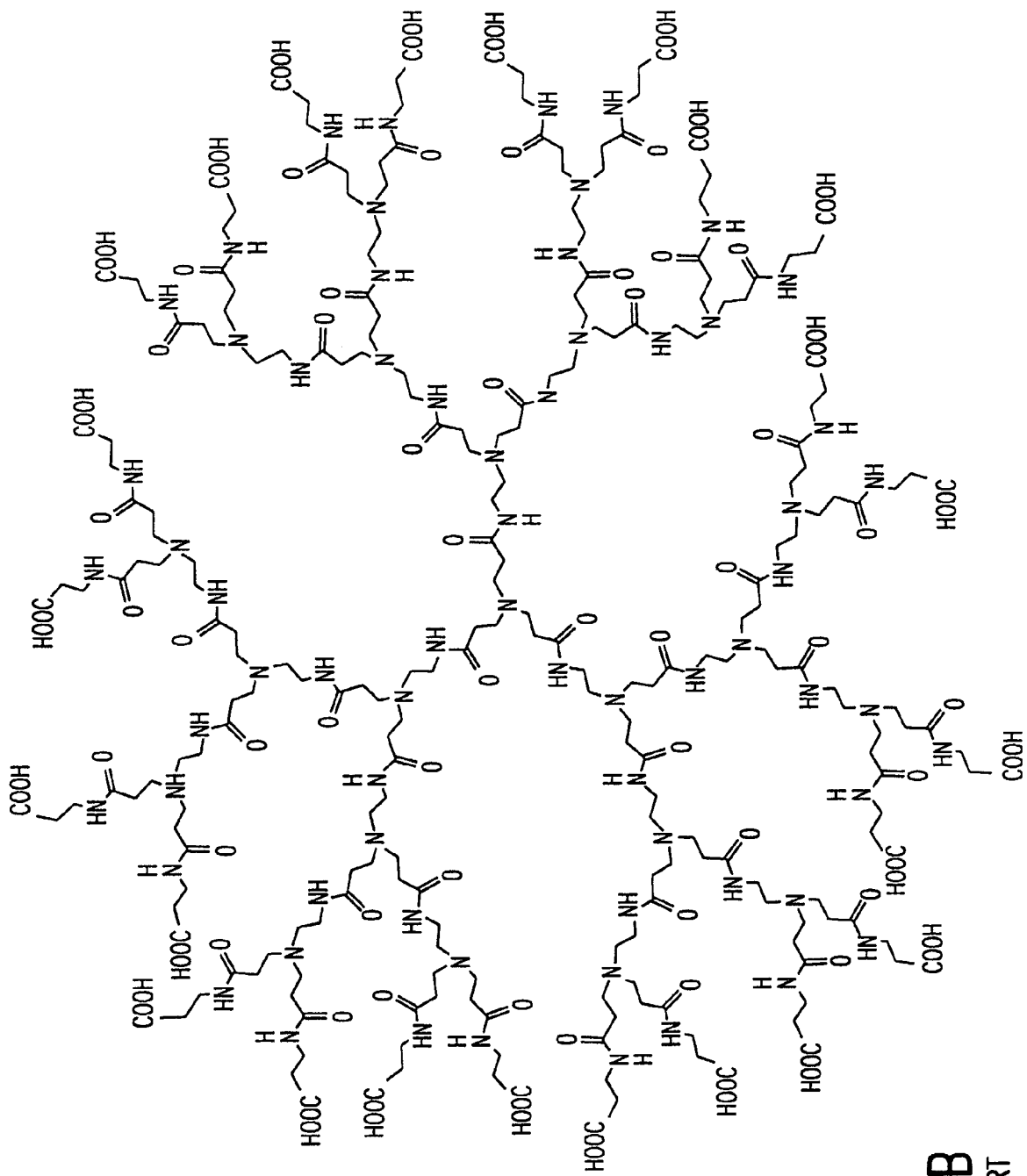
Figure 1C:
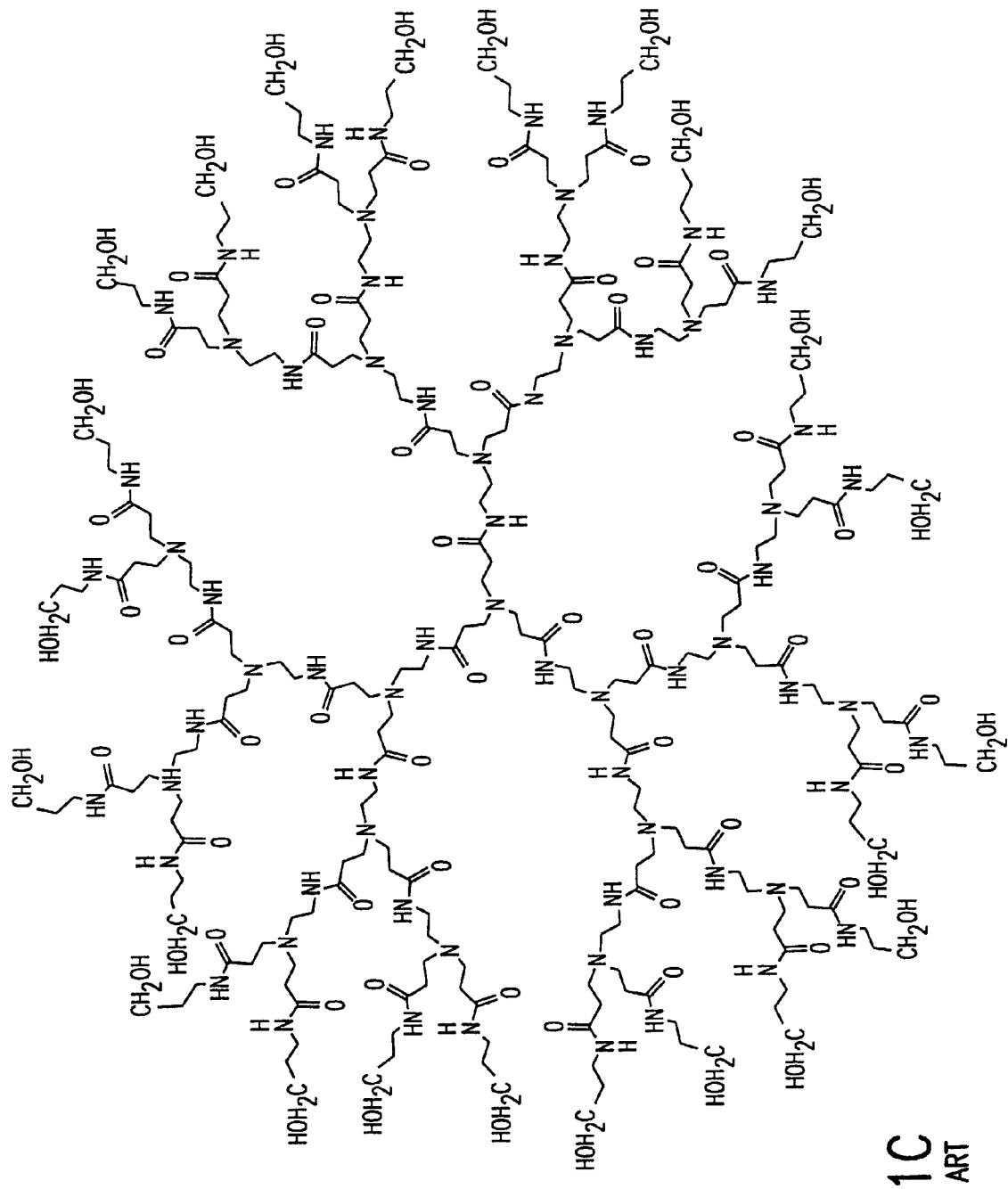
Figure 1D:
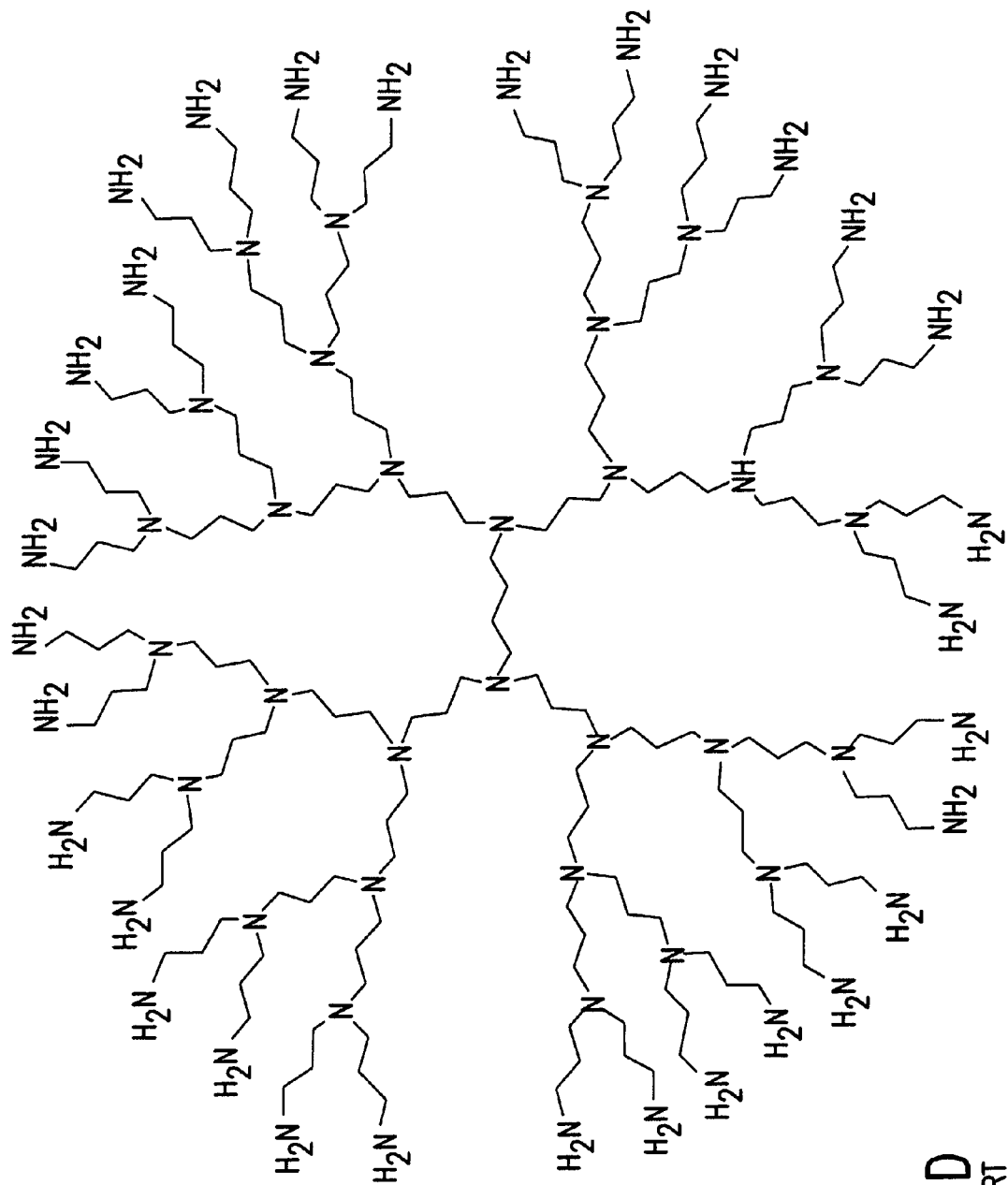
Figure 2A:
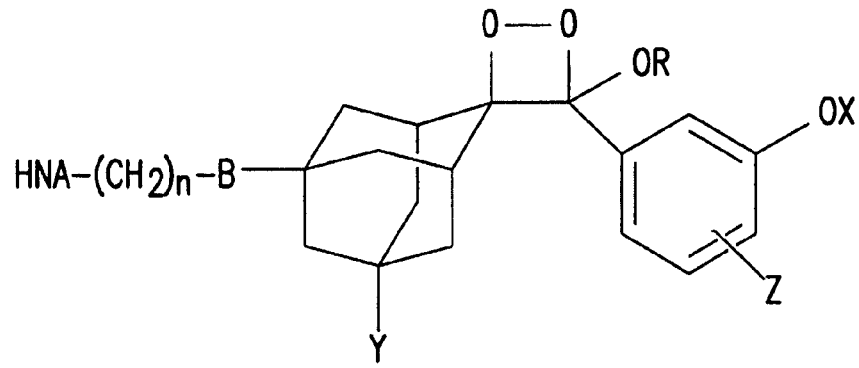
FIGS. 2A-2L show dioxetane coupling precursors according to the invention.
Figure 2B:
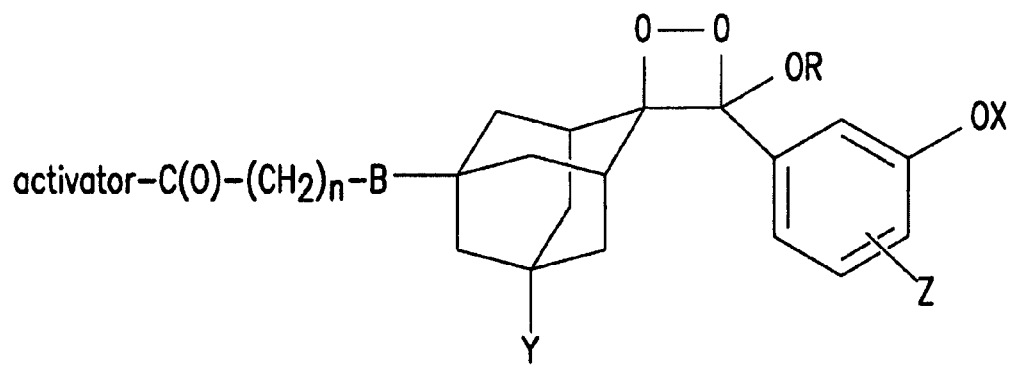
Figure 2C:
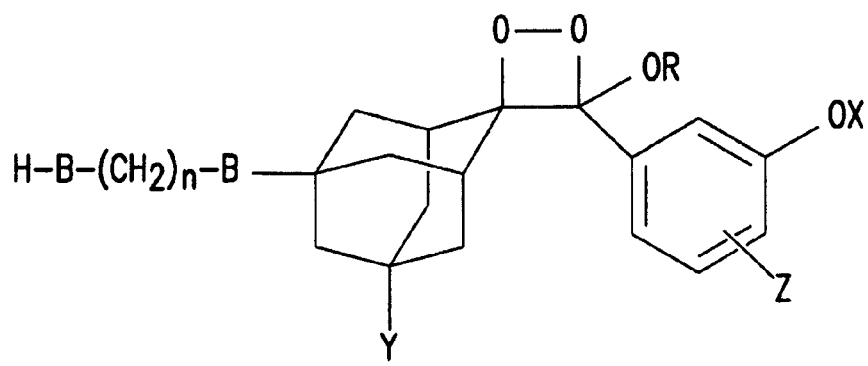
Figure 2D:
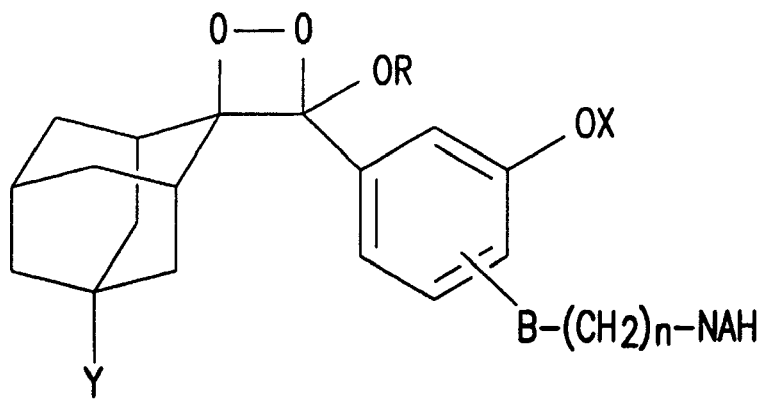
Figure 2E:
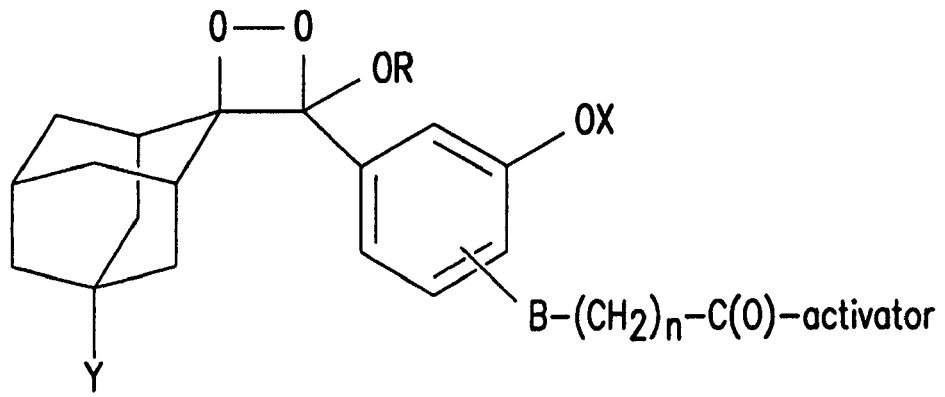
Figure 2F:
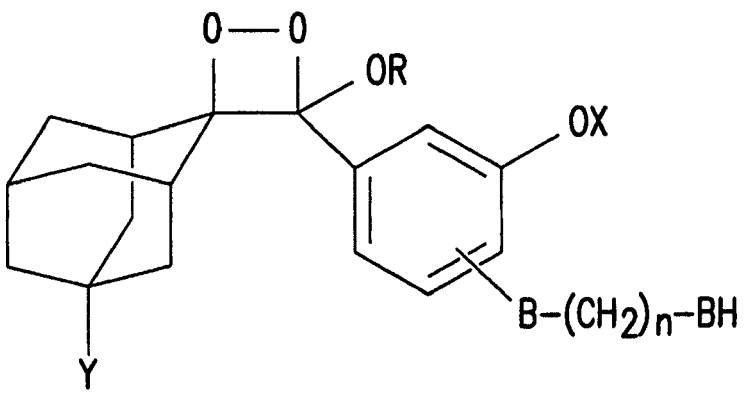
Figure 2G:
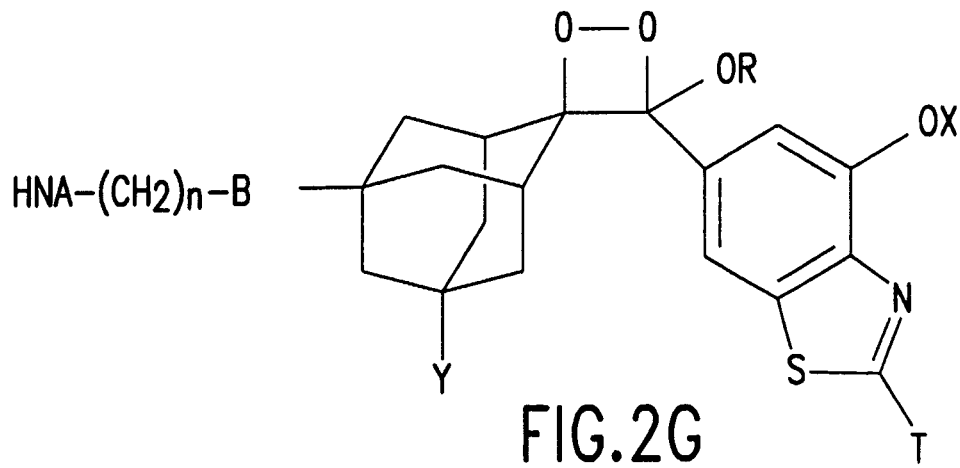
Figure 2H:
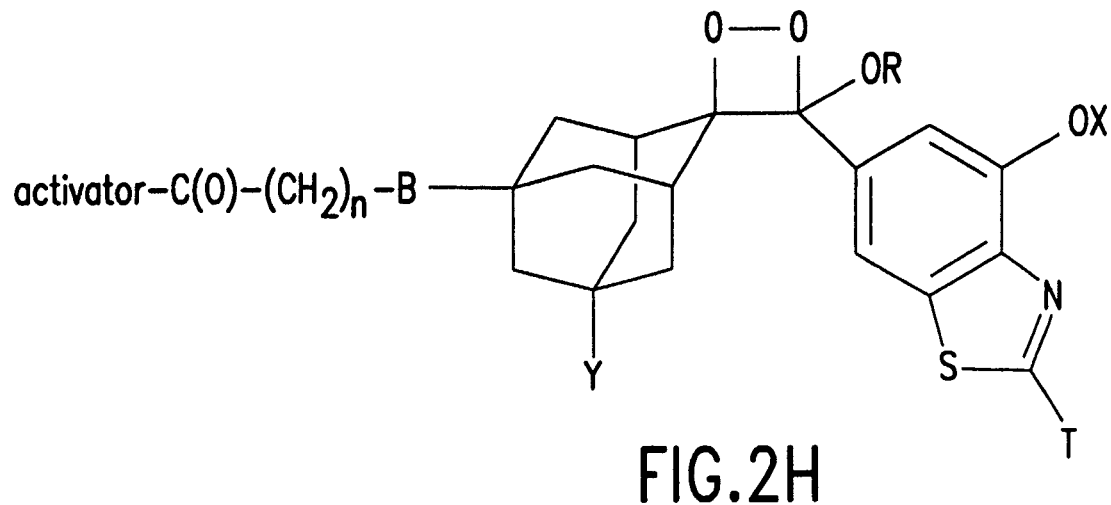
Figure 2I:
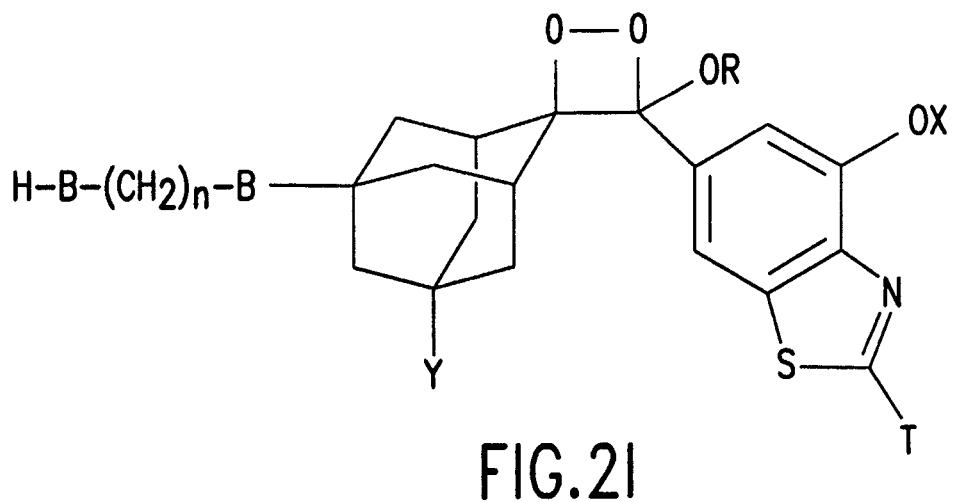
Figure 2J:
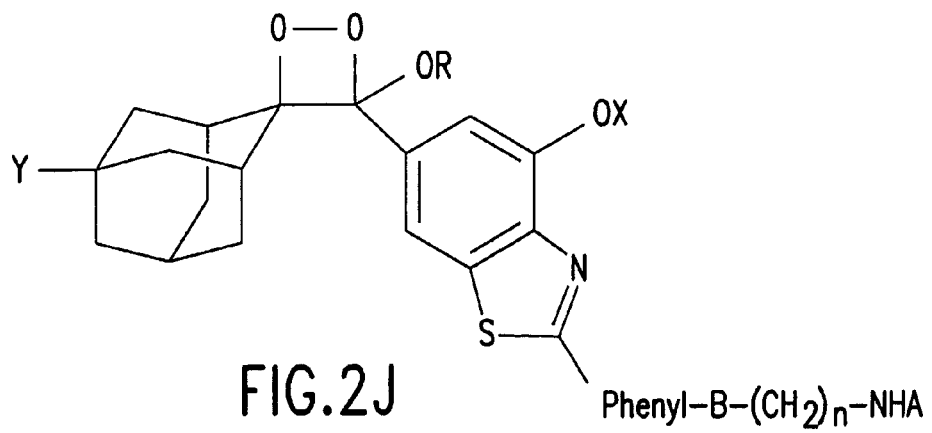
Figure 2K:
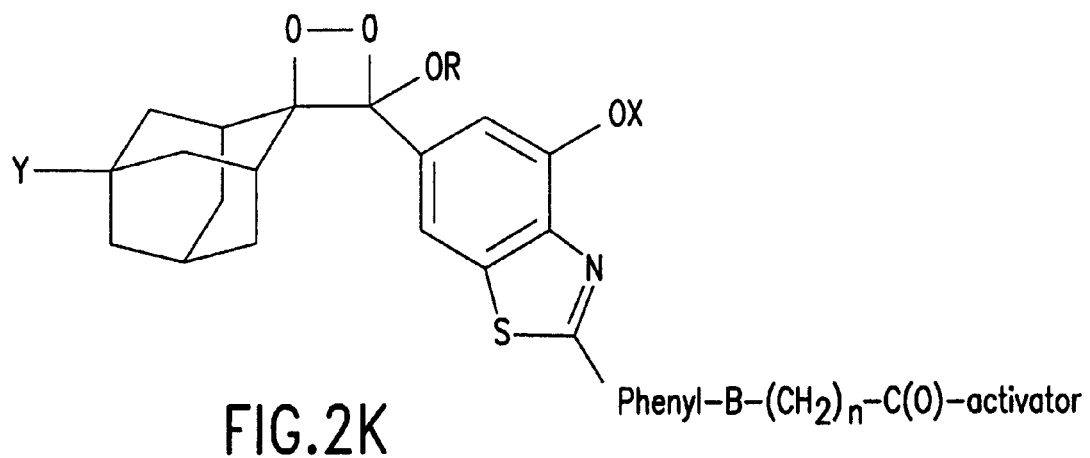
Figure 2L:
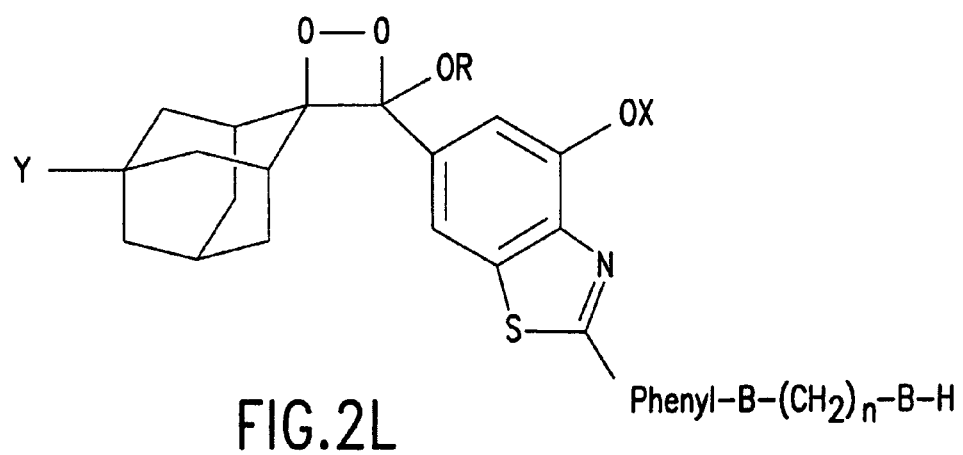

According to an embodiment of the invention, dendritic polymer chemiluminescent substrates containing one or more dioxetanes, luminols, isoluminols, acridinium esters, acridinium sulfonylamides and/or luciferins coupled to the surface of known dendrimer polymers can be synthesized. Non-limiting examples of some dendrimer starting materials that may be employed to synthesize the dendritic polymer chemiluminescent substrates of the invention are depicted in FIGS. 1A-1D. FIG. 1A shows a polyamidoamine (PAMAM) dendrimer with $NH_2$ surface groups. FIG. 1B shows a polyamidoamine (PAMAM) dendrimer with carboxylic acid surface groups. FIG. 1C shows a polyamidoamine (PAMAM) dendrimer with hydroxyl surface groups. FIG. 1D shows a polypropyleneimine (PEI) dendrimer with $NH_2$ surface groups.

Chemiluminescent substrate coupling precursors that may be employed to synthesize the dendritic polymer chemiluminescent substrates of the invention are shown in FIGS. 2A-2L. In FIGS. 2A-2L, the substituents are defined as follows:

A is H, alkyl, trihaloalkyl or aryl;

B is NA, NC(O)A, O, S or $CH_2$ wherein A is independently H, alkyl, trihaloalkyl or aryl;

Y is independently H, a hydroxyl group, a halogen, an unsubstituted lower alkyl group, a hydroxy lower alkyl group, a halo lower alkyl group, a phenyl group, a halo phenyl group, an alkoxy phenyl group, an alkoxy phenoxy group, a hydroxy alkoxy group, a cyano group, an amide group, an alkoxy group or a carboxyl group;

R is an alkyl group (e.g., a $C_1$-$C_{12}$ alkyl group), a haloalkyl group (e.g., a mono-, di-, or trihaloalkyl), an aryl group or an aralkyl group;

X is an enzyme-labile group selected from the group consisting of a phosphate, galactoside, acetate, 1-phospho-2,3-diacylglyceride, 1-thio-D-glucoside, adenosine triphosphate, adenosine diphosphate, adenosine monophosphate, adenosine, α-D-glucoside, β-D-glucoside, β-D-glucuronide, β-D-mannoside, β-D-fructofuranoside, β-glucosiduronate, 5-acetamido-3-5-dideoxy-α-D-glycero-D-galacto-2-nonulopyranoside and alkoxy derivatives (e.g., 4,7-di-O-methyl), p-toluenesulfonyl-L-arginine ester, and p-toluenesulfonyl-L-arginine amide;

Z is a halo, alkoxy or alkyl group; and

T is H, an electron donating group, an electron withdrawing group, or an organic linker group which may be attached to an ancillary fluorophore or to any biological moiety.

Figure 3A:
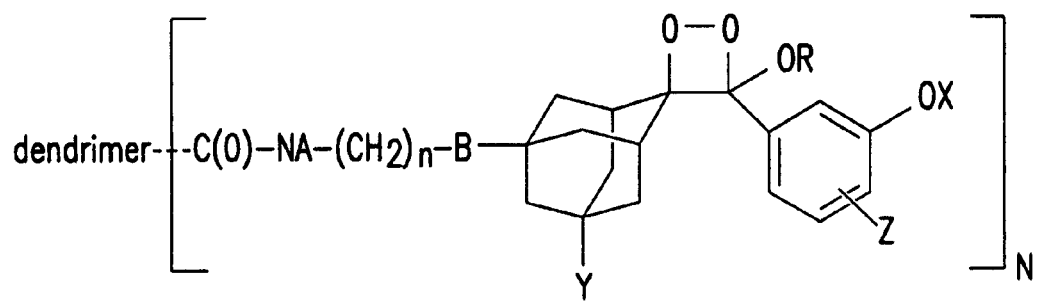
FIGS. 3A-3O show dendritic polymer dioxetane conjugates according to the invention.
Figure 3B:
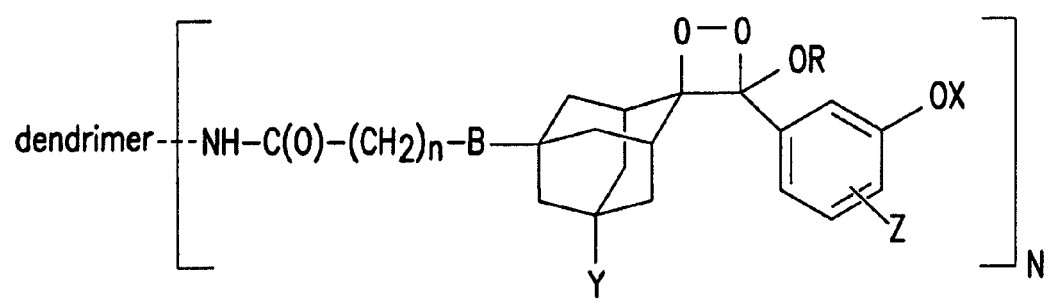
Figure 3C:
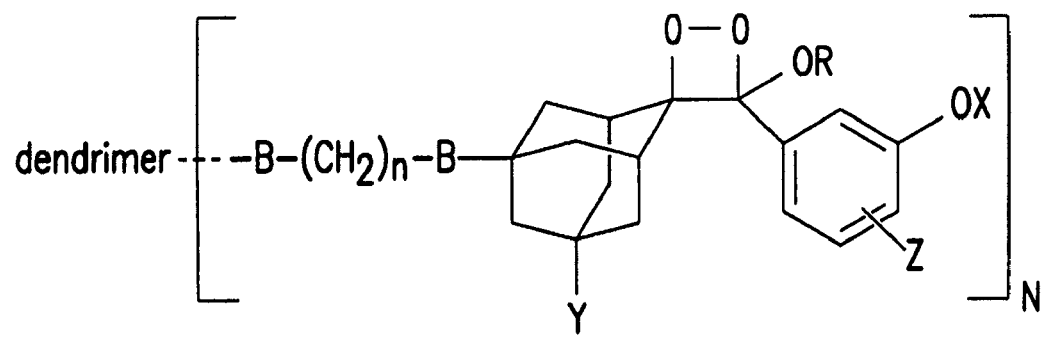
Figure 3D:
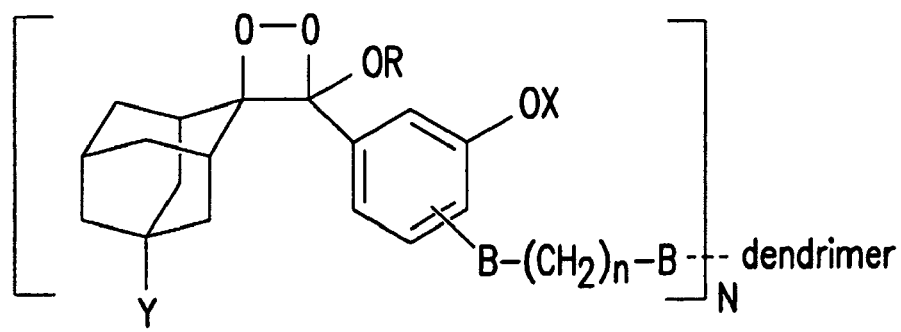
Figure 3E:
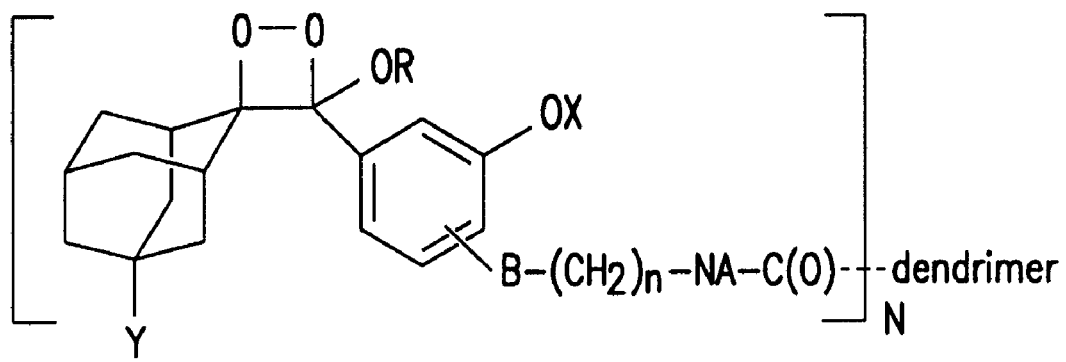
Figure 3F:
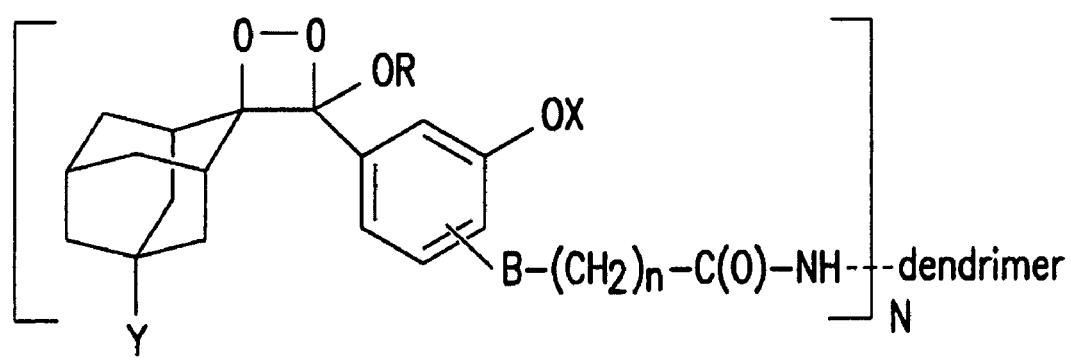

Examples of general structures of dendritic polymer dioxetane conjugates according to the invention are shown in FIGS. 3A-3O. In FIGS. 3A-3L, the substituents A, B, Y, R, X, Z and T are defined as set forth above with respect to FIGS. 2A-2L. N, which represents the number of dioxetane moieties conjugated to the dendrimer, is a positive integer. According to a preferred embodiment of the invention, N in FIGS. 3A-3F is from 6 to 768.

Figure 3G:
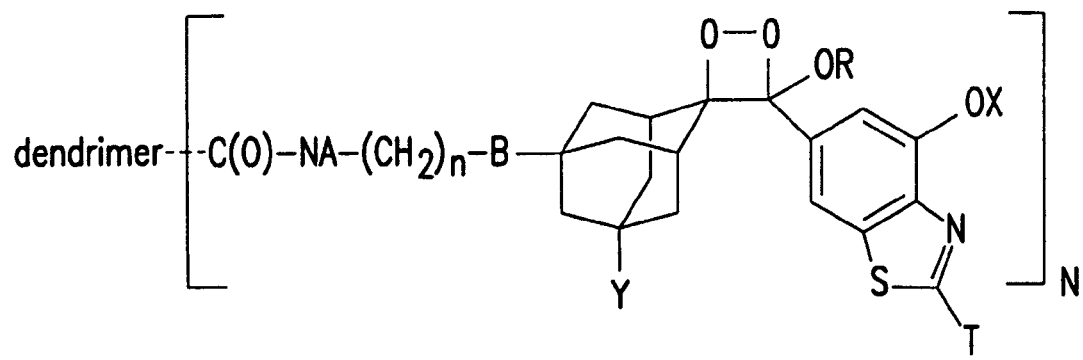
Figure 3H:
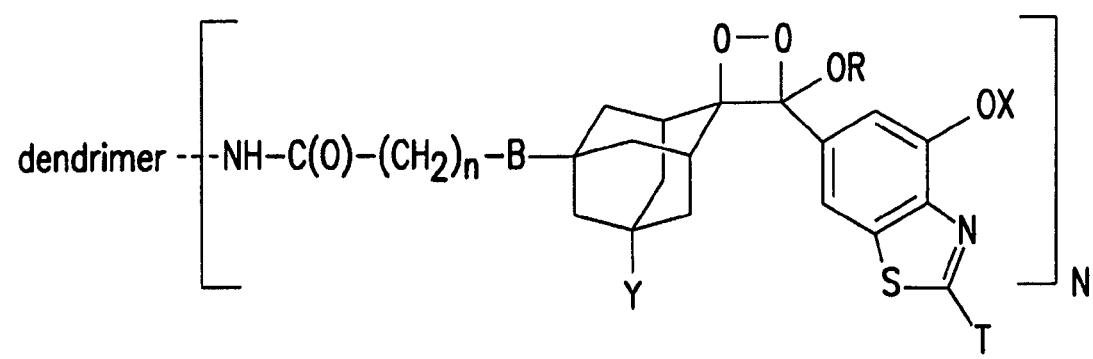
Figure 3I:
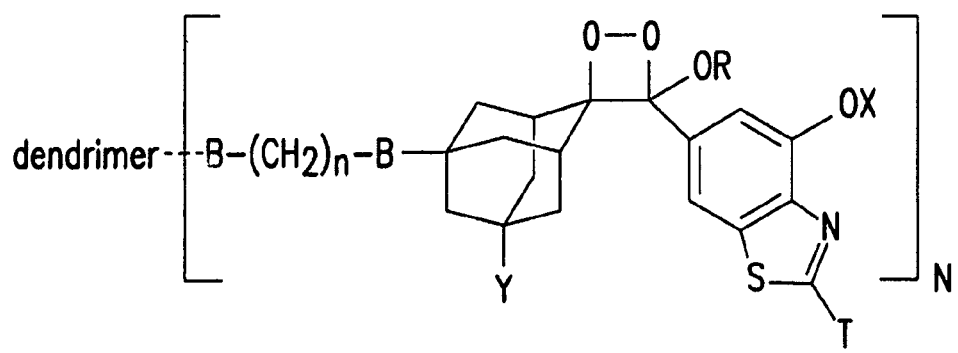
Figure 3J:
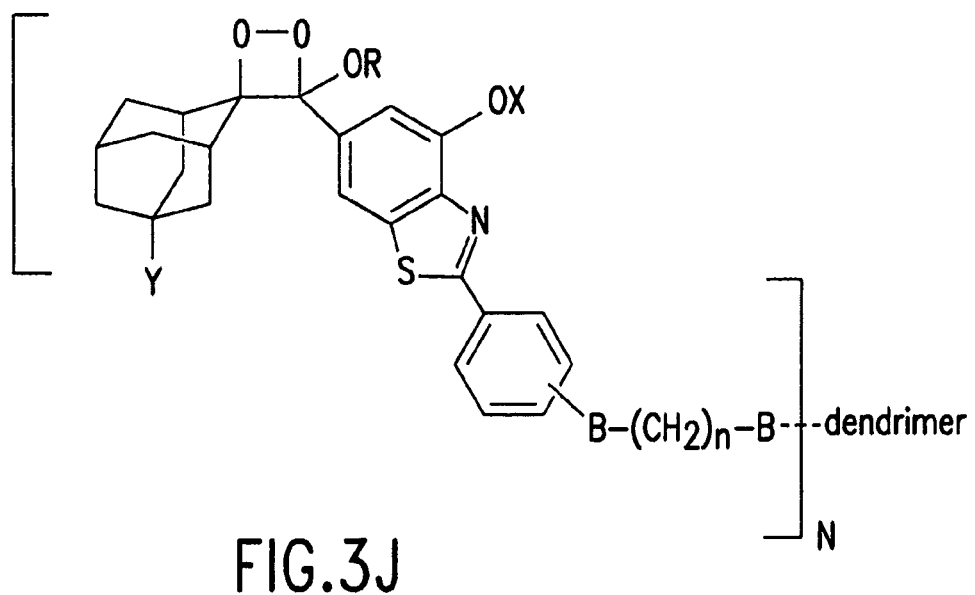
Figure 3K:
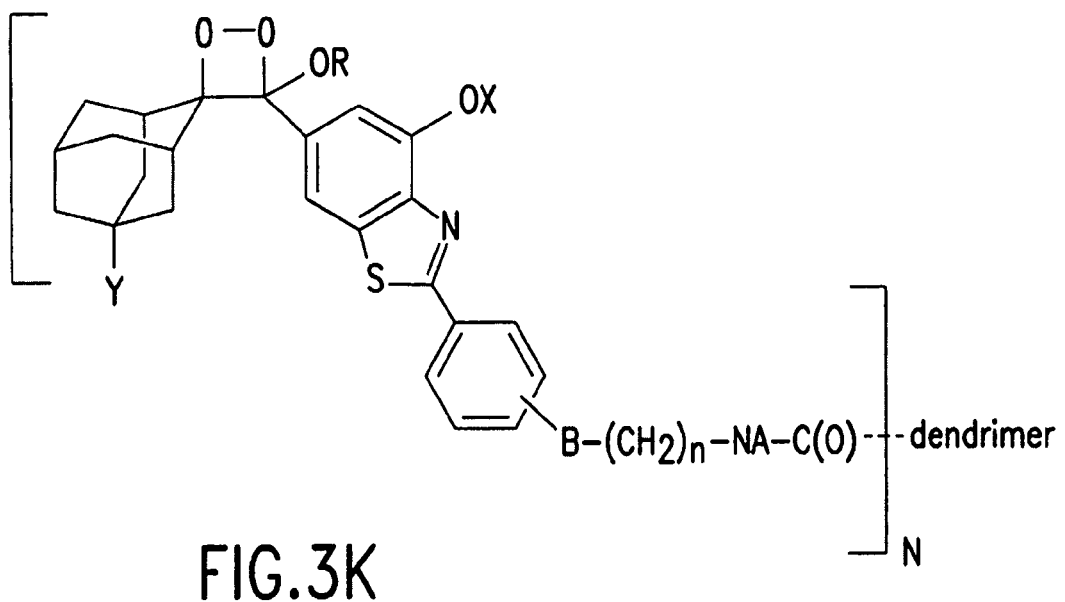
Figure 3L:
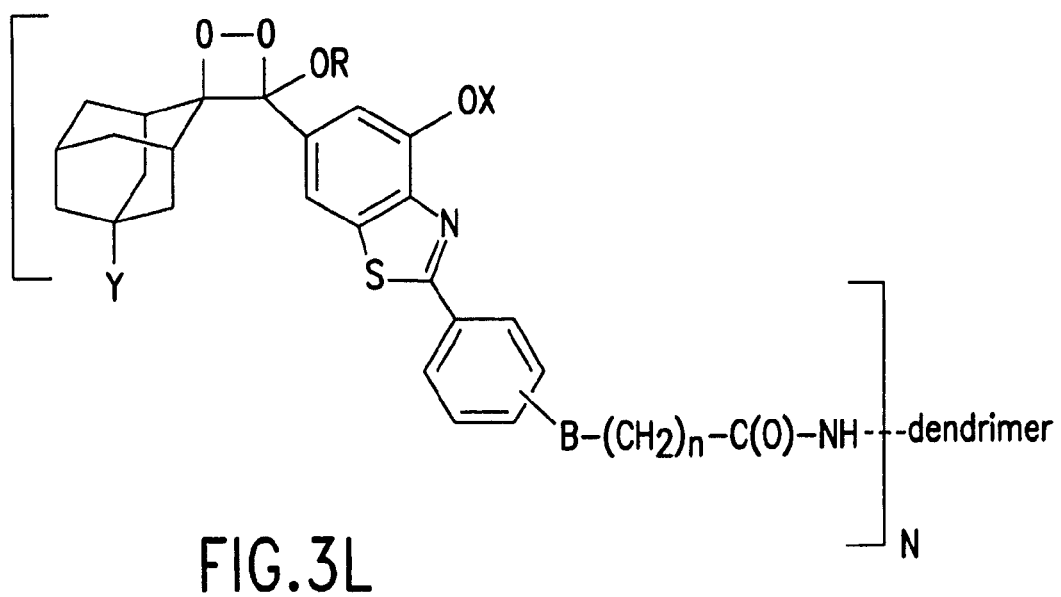
Figure 3M:
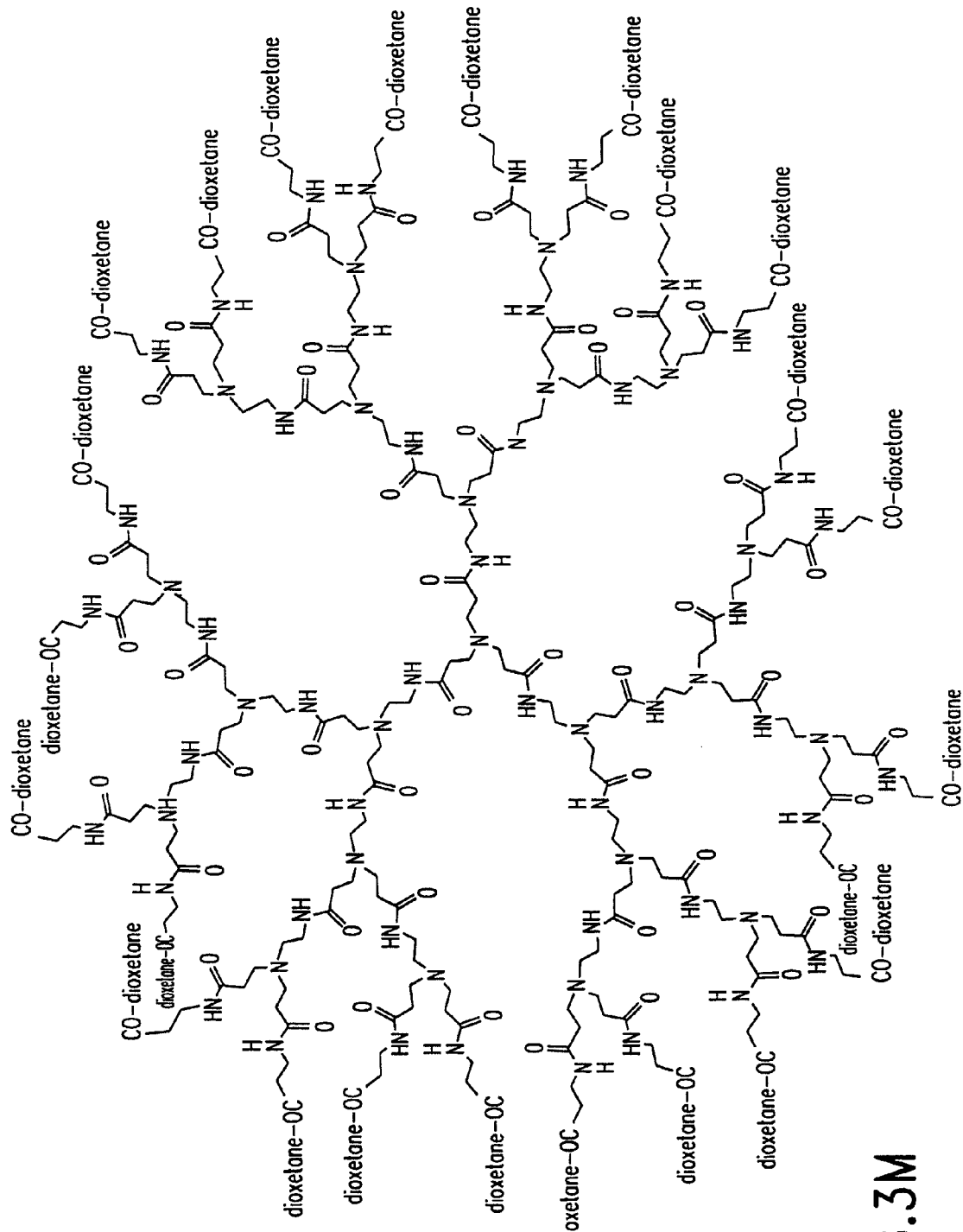
Figure 3N:
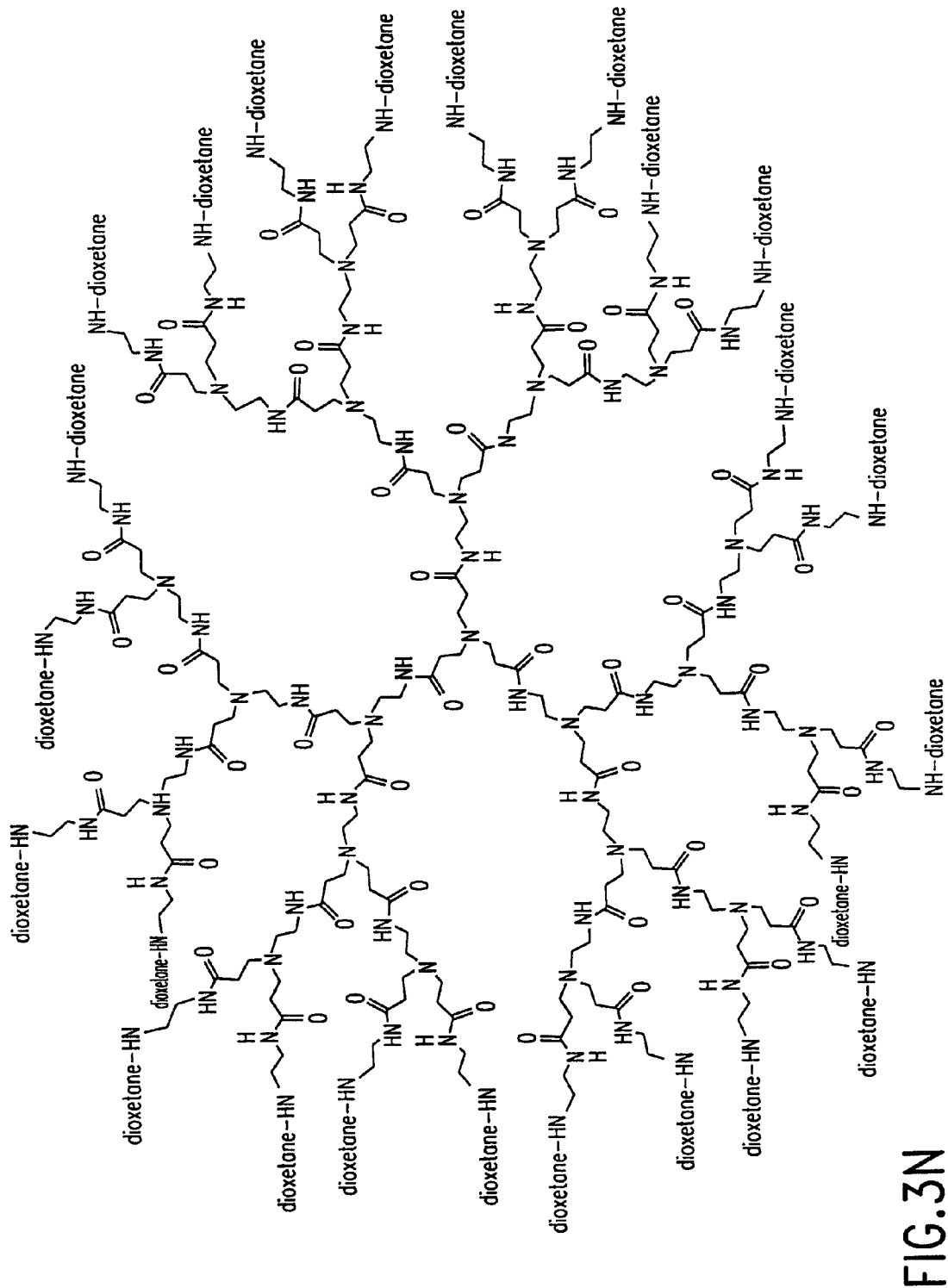
Figure 30:
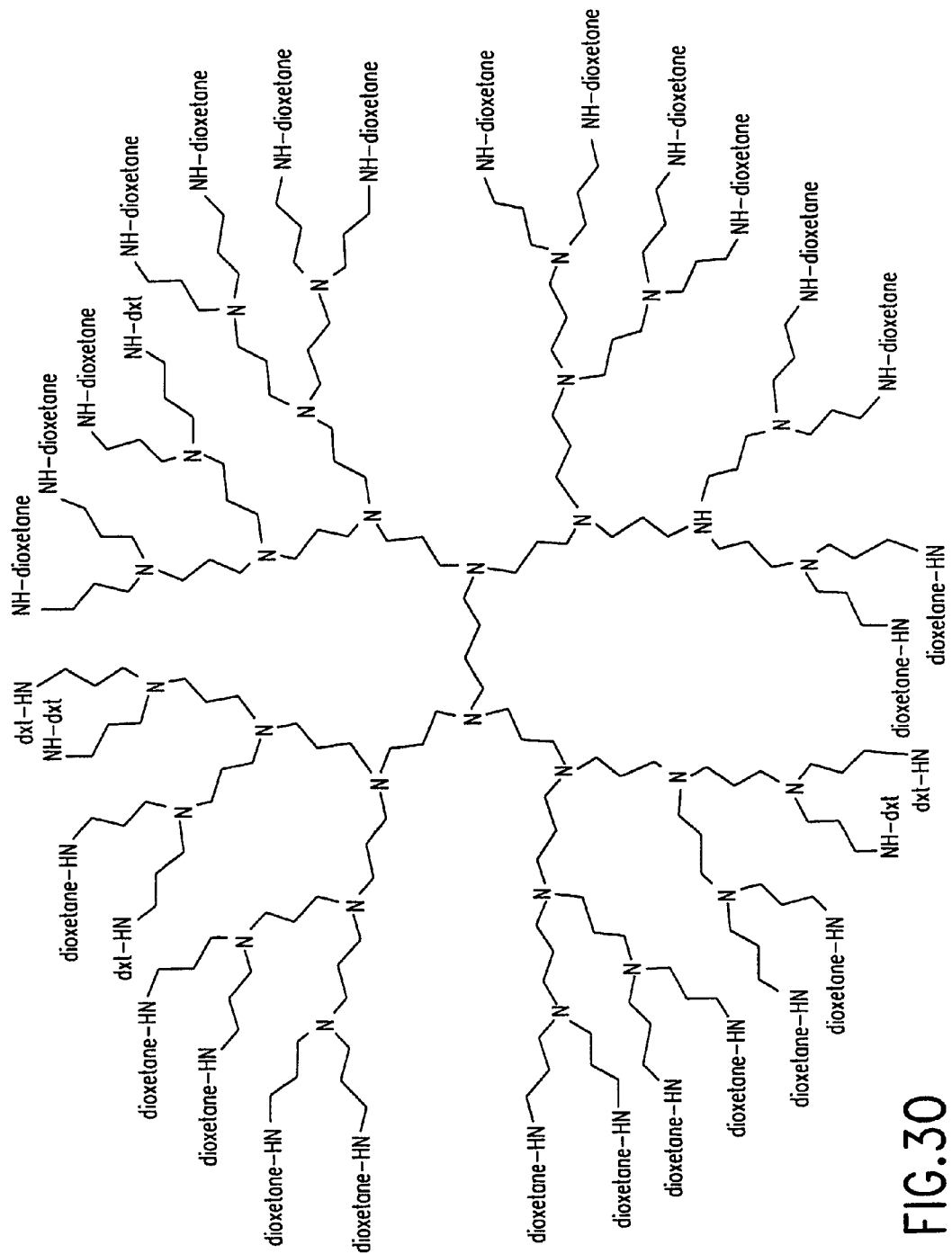

FIG. 3M shows a polyamidoamine (PAMAM) Starburst Dendrimer having carboxylic acid surface groups conjugated with a plurality of dioxetanes according to the invention. FIG. 3N shows a polyamidoamine (PAMAM) Starburst Dendrimer having amino terminal groups conjugated with a plurality of dioxetanes according to another embodiment of the invention. FIG. 3O shows a polypropyleneimine (PEI) starburst dendrimer having amino surface groups conjugated with a plurality of dioxetanes according to a further embodiment of the invention.

FIGS. 4A-4F shows synthesis schemes for the dendritic polymer conjugates shown in FIGS. 3A-3L. In FIGS. 4A-4F, the substituents A, B, Y, R, X and N are as defined above. The "activator" can be a mixed anhydride, an NHS ester, or another standard functionality used in peptide chemistry to facilitate peptide bond formation. The "leaving group" can be a halogen or a sulfonic ester such as mesylate, tosylate or triflate.

Figure 4A:
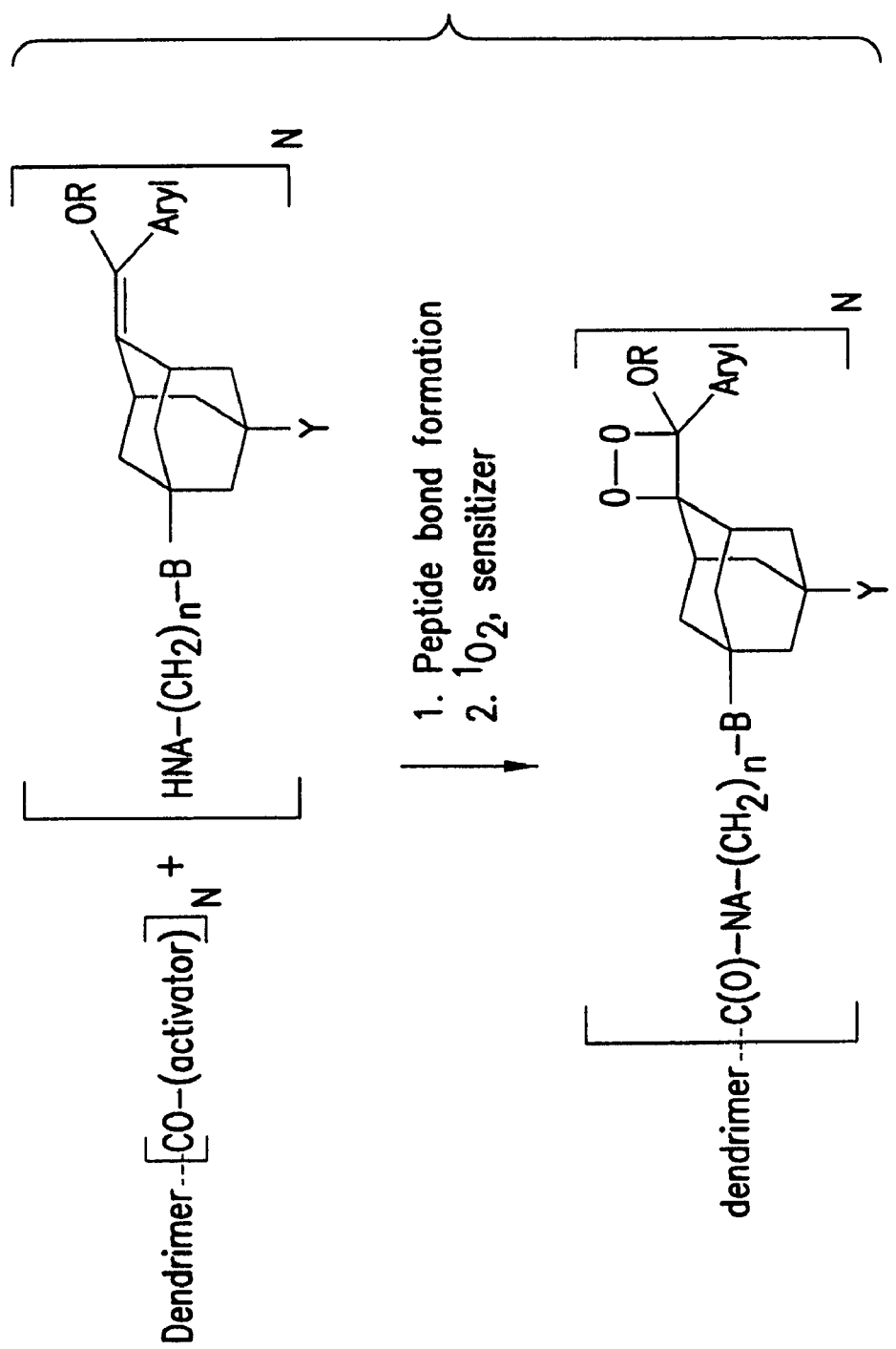
Figure 4B:
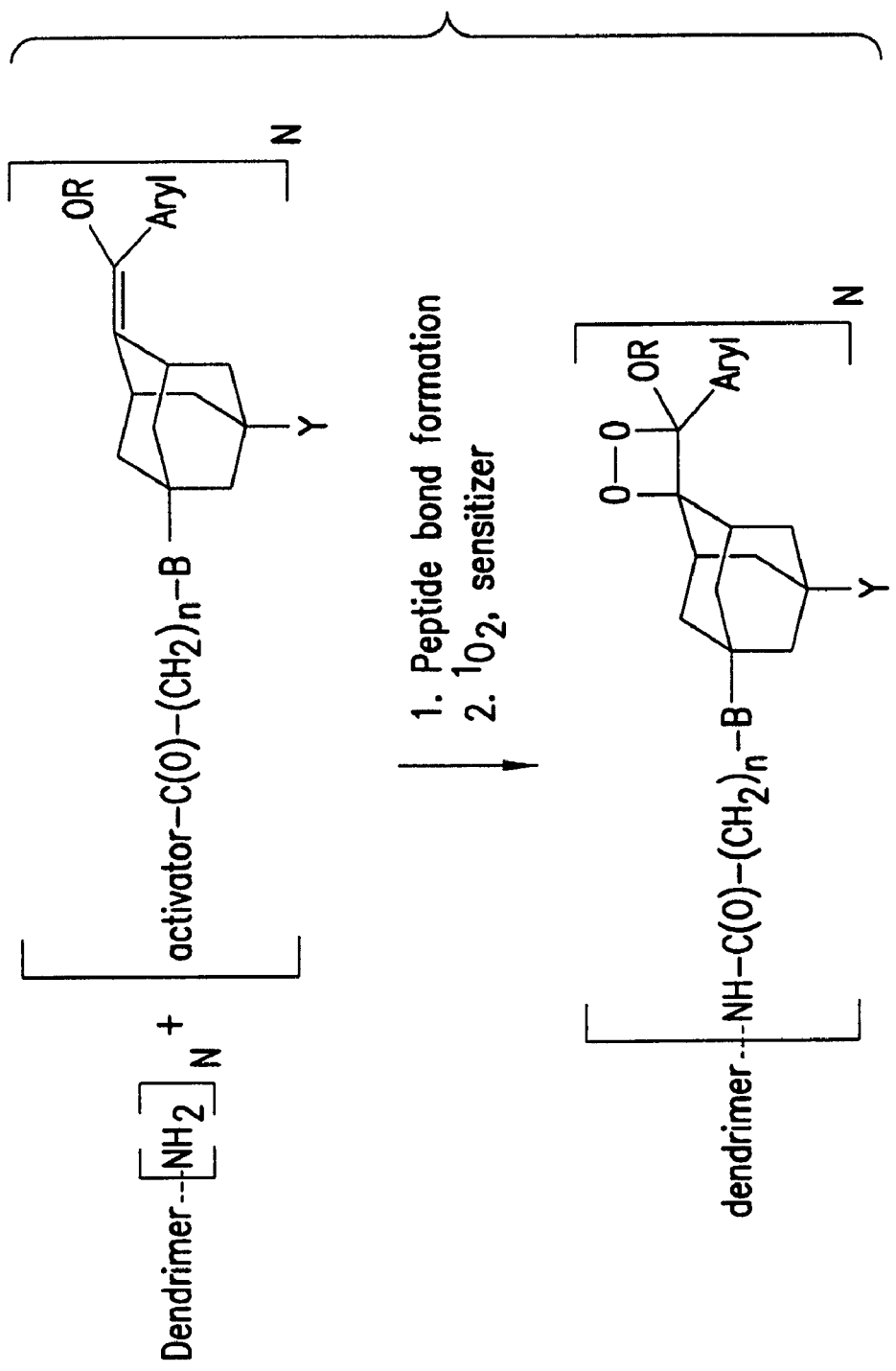
Figure 4C:
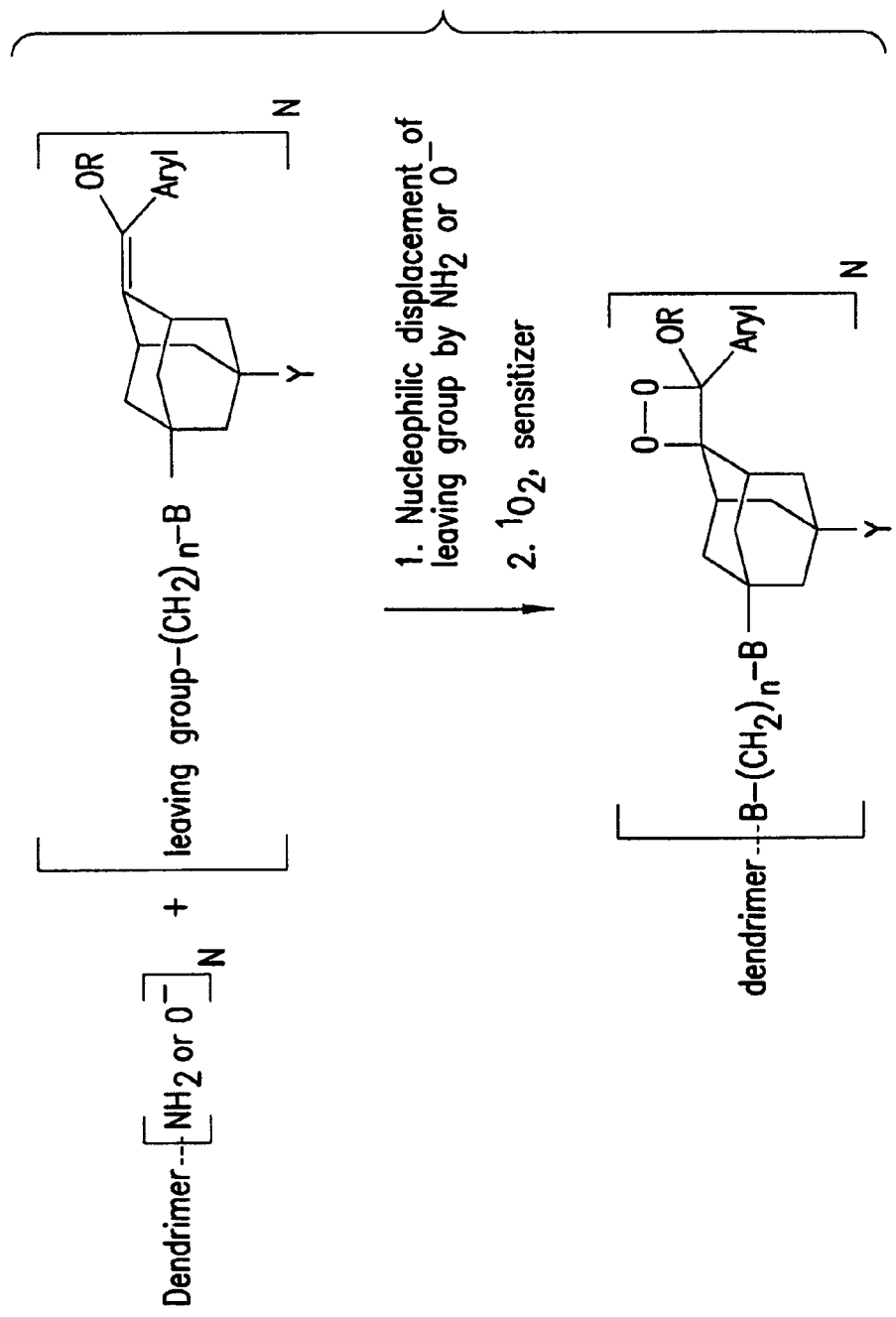
Figure 4D:
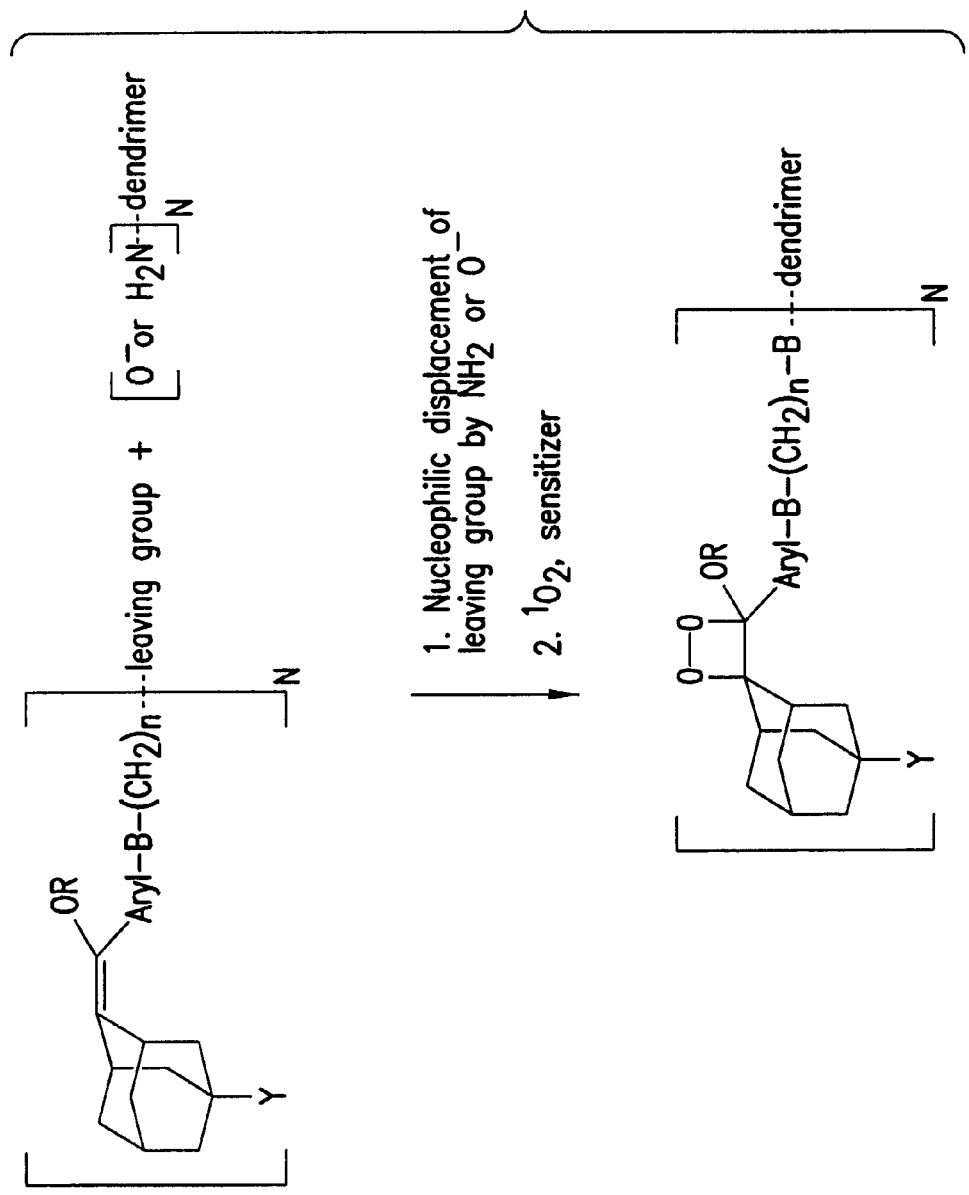
Figure 4E:
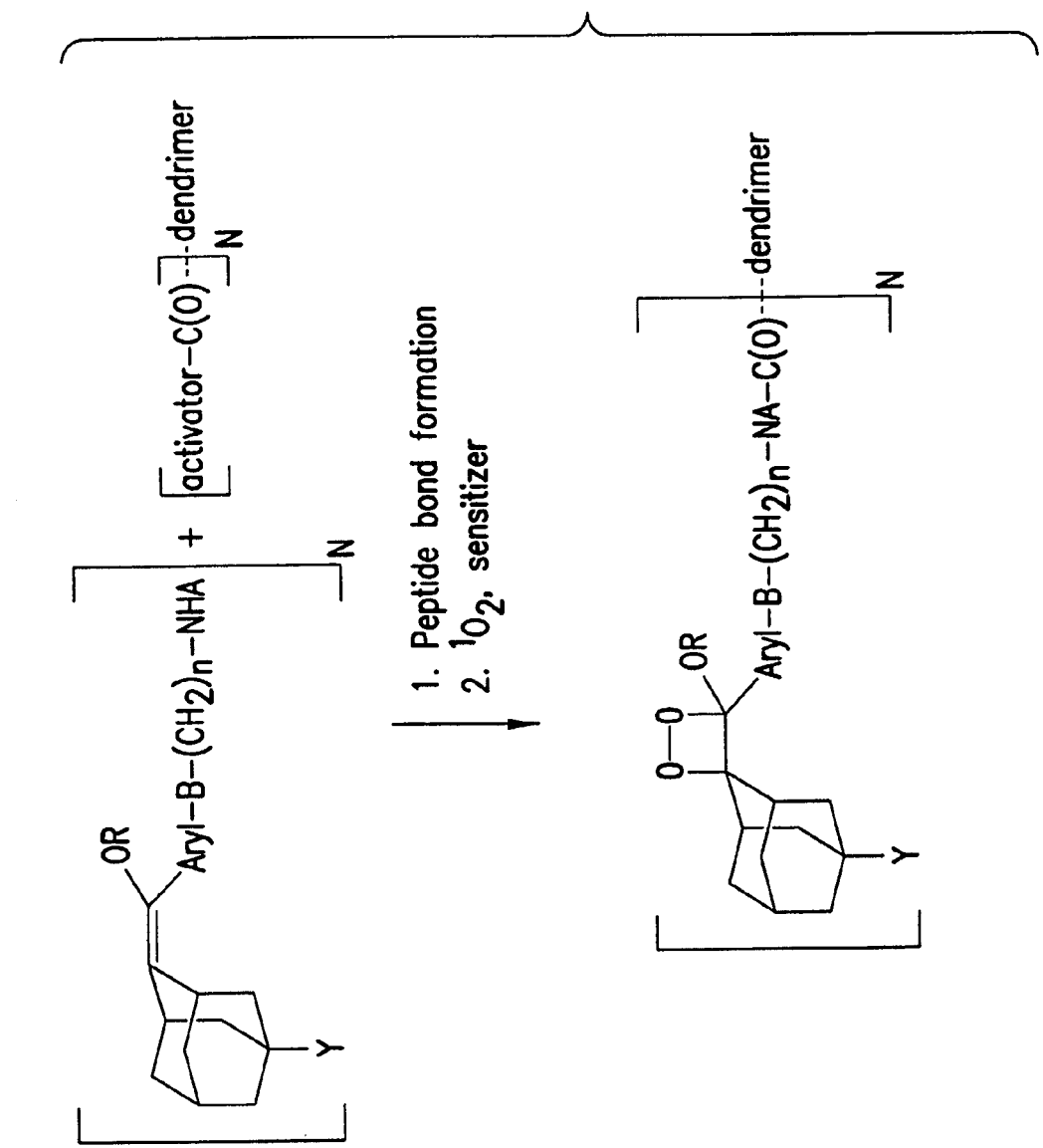
Figure 4F:
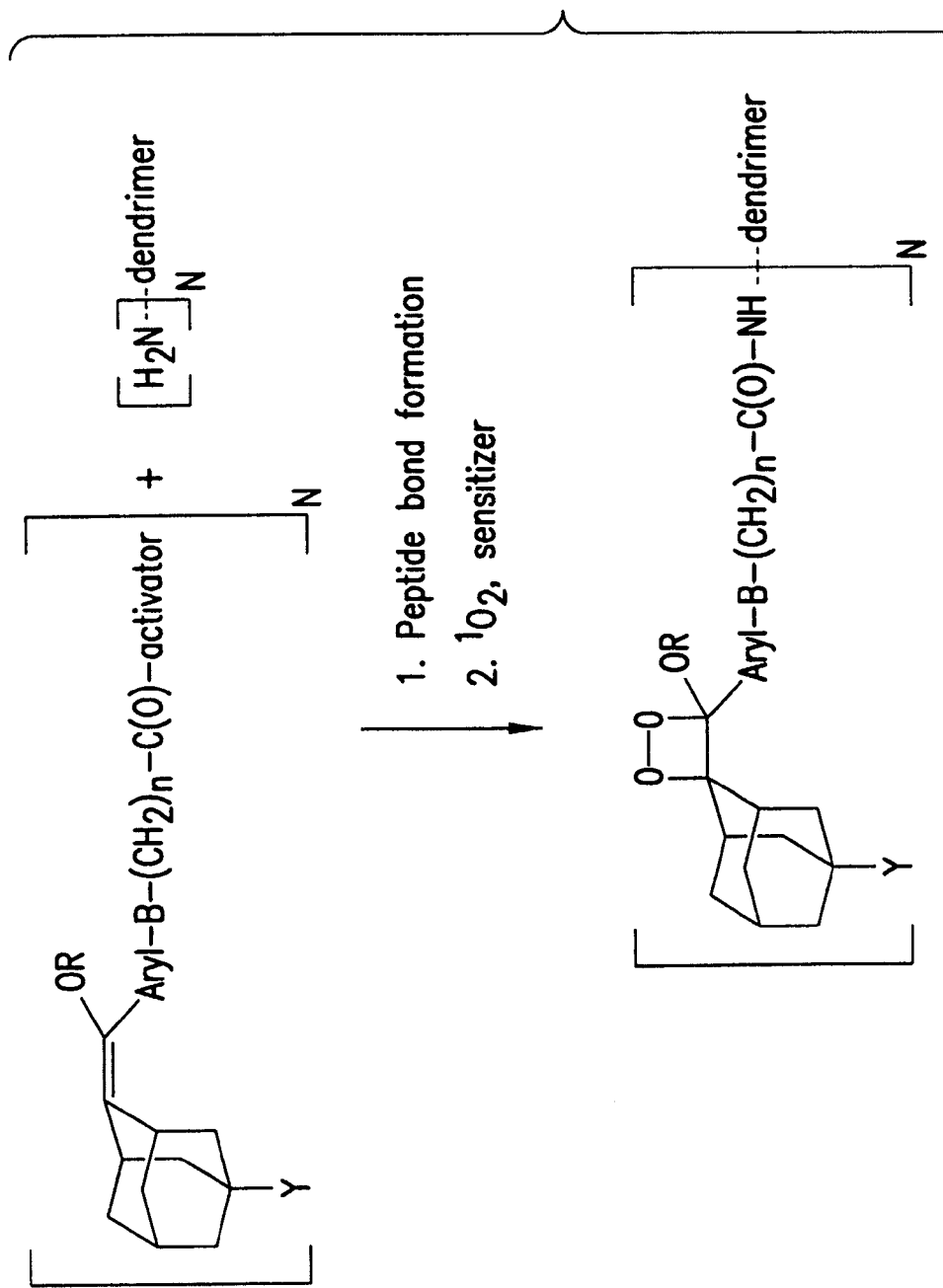

In FIG. 4A, the "Aryl" substituent can be a phenyl group or a benzothiazole as defined in FIG. 3A or 3G. In FIG. 4B, the "Aryl" substituent can be a phenyl group or a benzothiazole as defined in FIG. 3B or 3H. In FIG. 4C, the "Aryl" substituent can be a phenyl group or a benzothiazole as defined in FIG. 3C or 3I. In FIG. 4D, the "Aryl" substituent can be a phenyl group or a benzothiazole as defined in FIG. 3D or 3J. In FIG. 4E, the "Aryl" substituent can be a phenyl group or a benzothiazole as defined in FIG. 3E or 3K. In FIG. 4F, the "Aryl" substituent can be a phenyl group or a benzothiazole as defined in FIG. 3F or 3L.

Figure 5A:
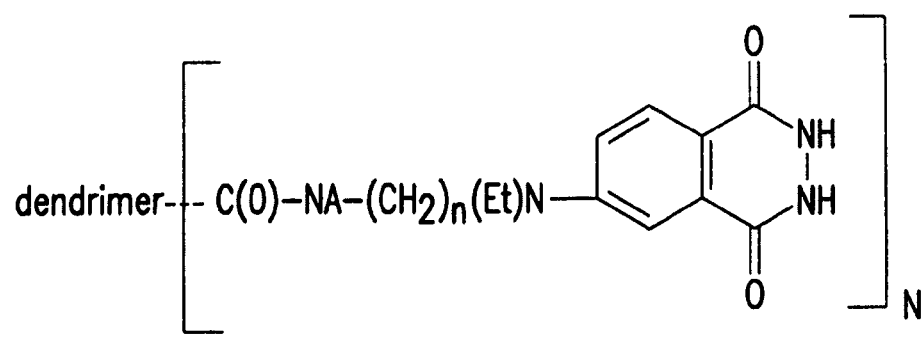
FIGS. 5A-5I and FIGS. 6A-6R show dendritic polymer isoluminol, acridinium ester, acridan, acridinium sulfonylamide, and luciferin conjugates according to the invention.
Figure 5B:
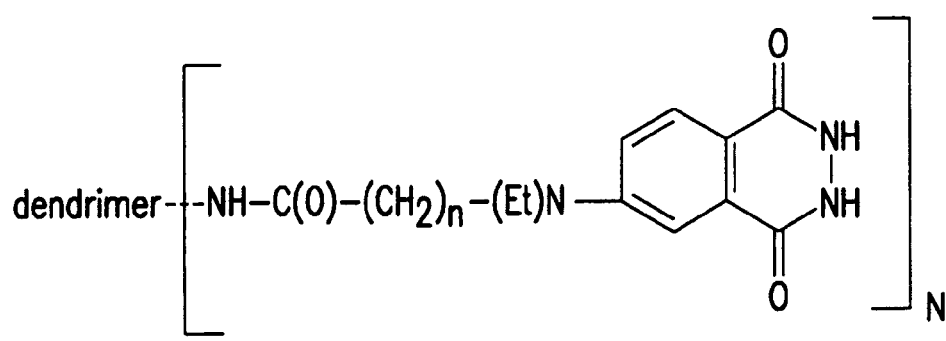
Figure 5C:
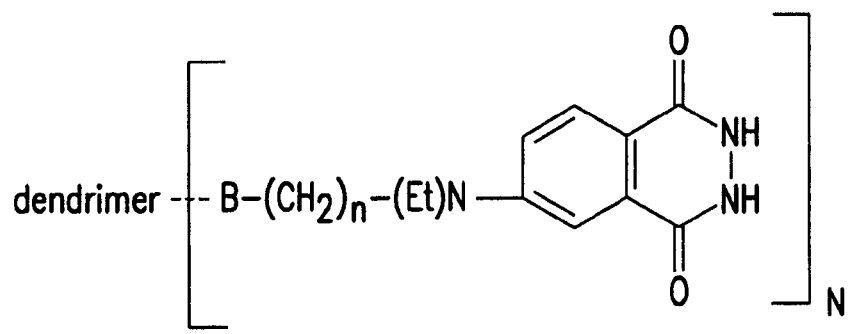

Further examples of dendritic polymer conjugates are shown in FIGS. 5A-5I and in FIGS. 6A-6J. FIGS. 5A-5C show dendritic polymer isoluminol conjugates according to the invention. In FIGS. 5A-5C, the substituent N is defined as set forth above. According to a preferred embodiment of the invention, N is from 6 to 768. In FIG. 5A, the substituent A can be hydrogen or an alkyl group. In FIG. 5C, the substituents A and B are defined as set forth above.

Figure 5D:
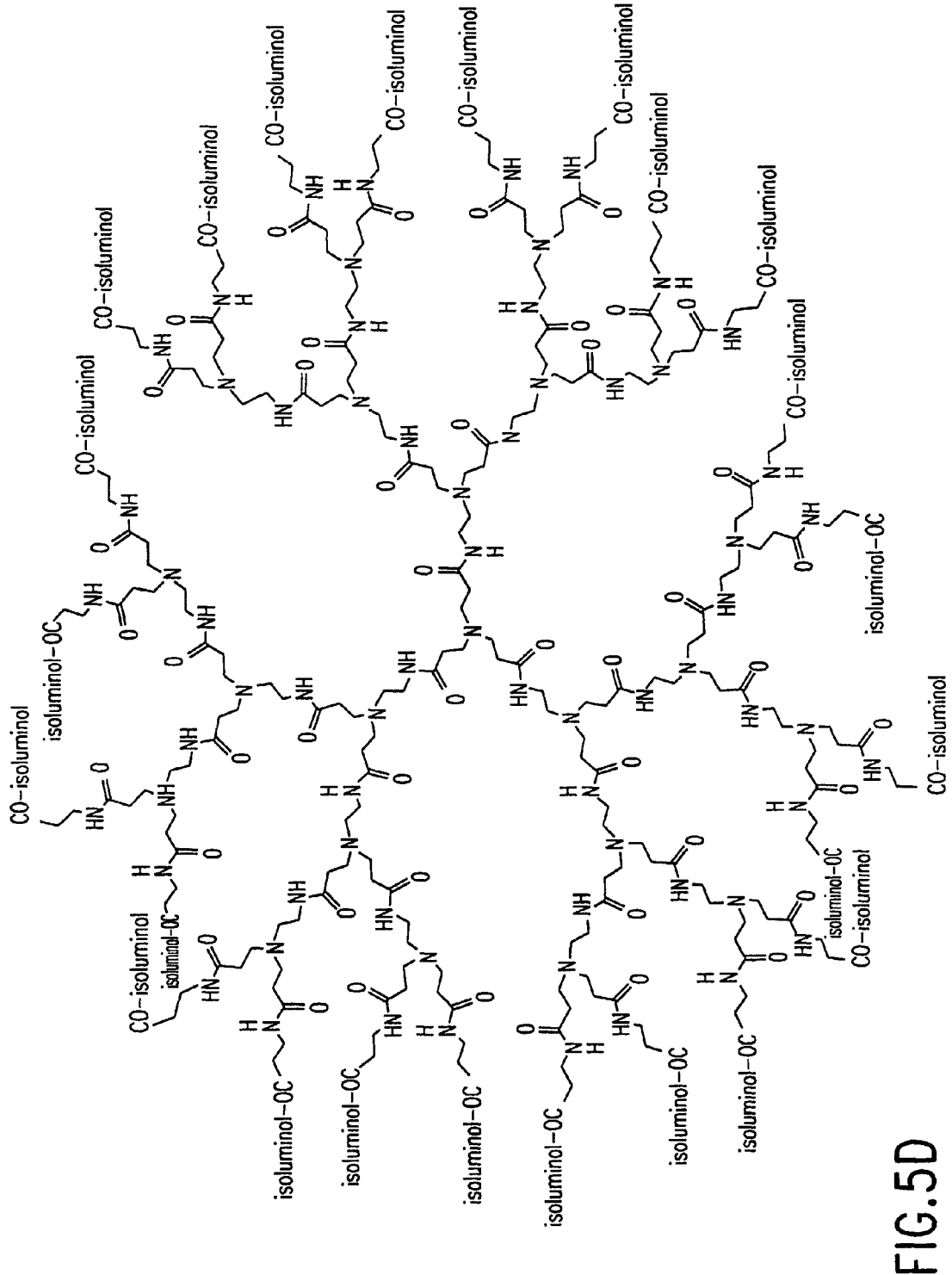
Figure 5E:
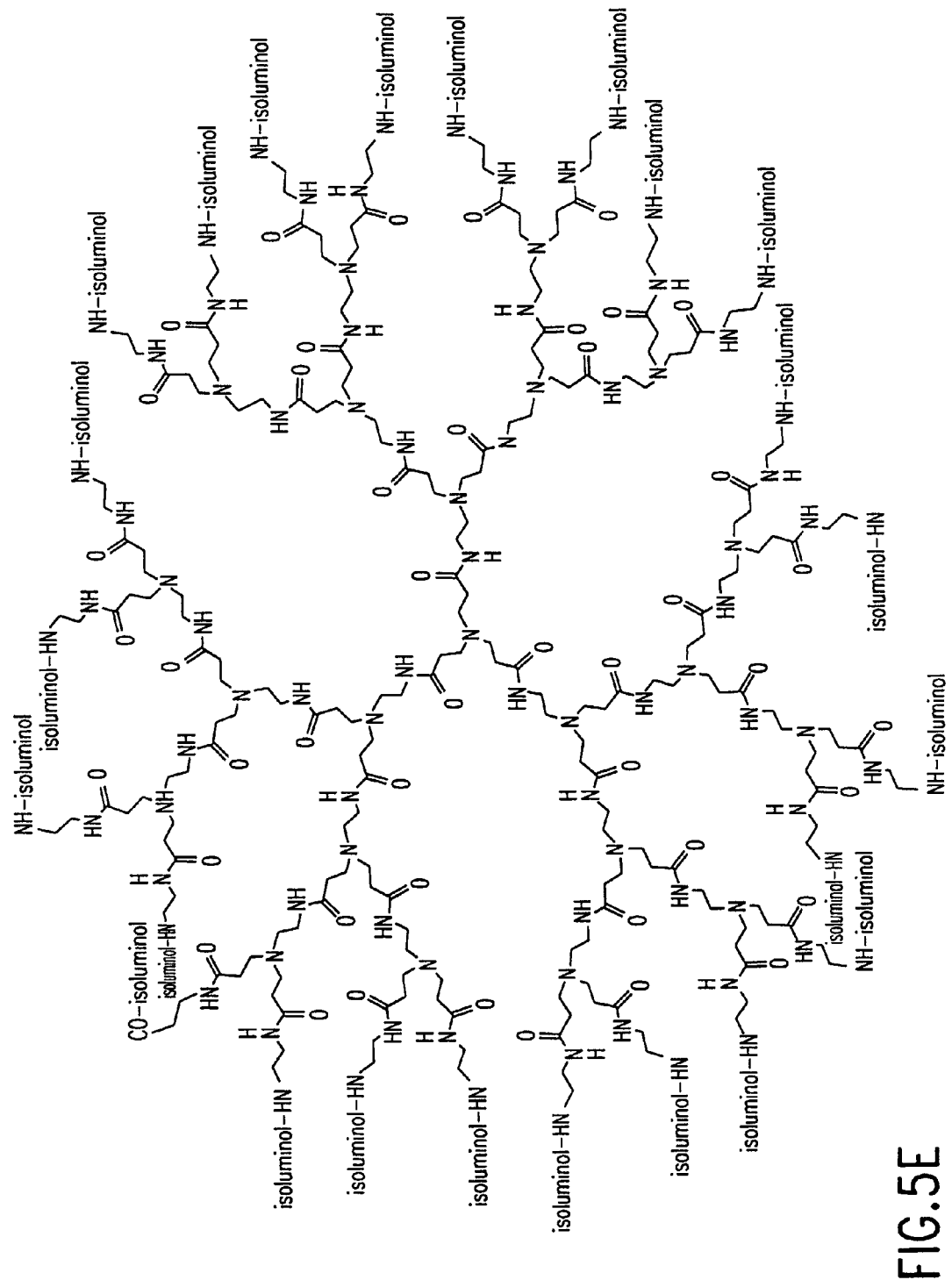
Figure 5F:
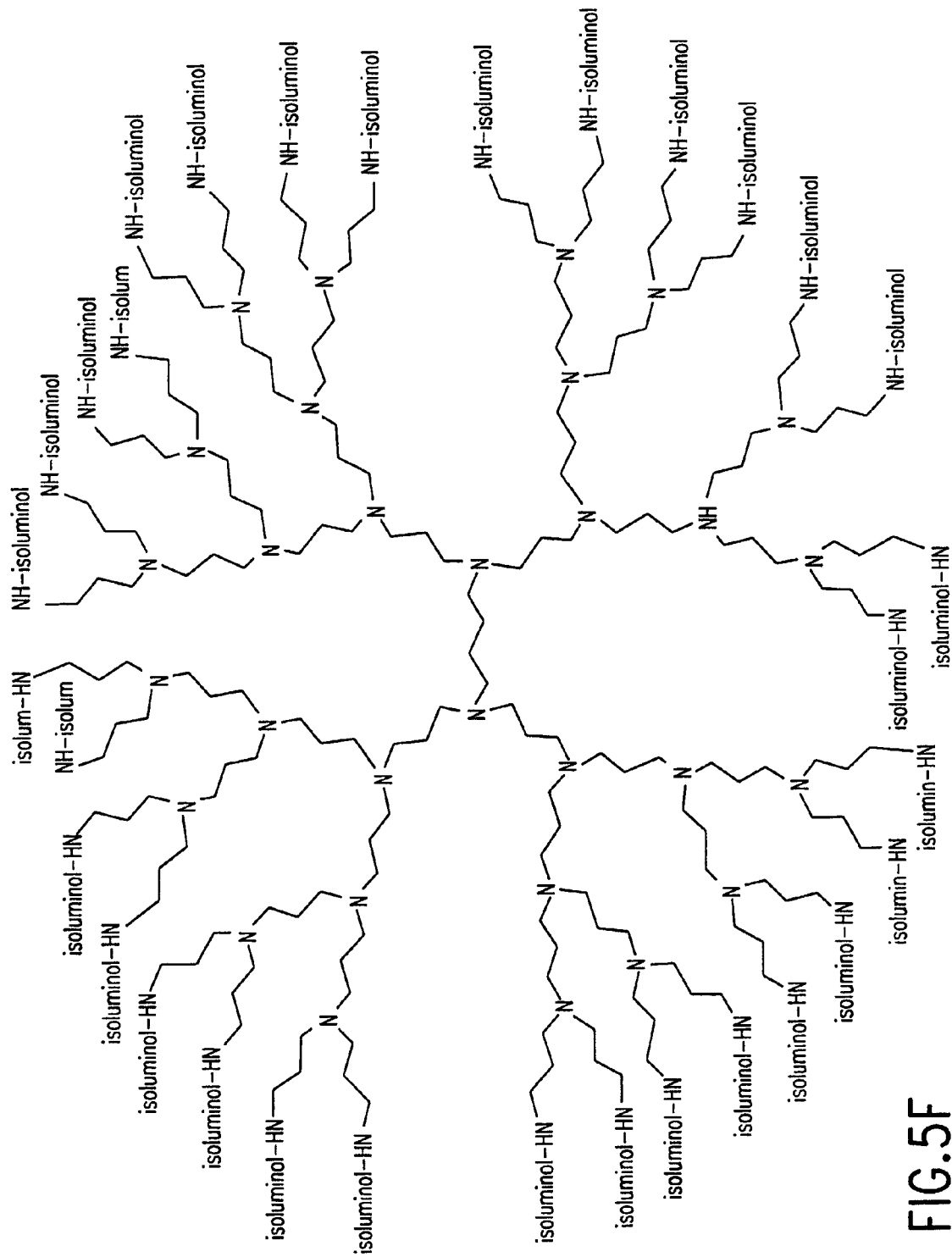

FIG. 5D shows a polyamidoamine (PAMAM) starburst dendrimer having carboxylic acid surface groups conjugated with a plurality of isoluminol moieties according to an embodiment of the invention. FIG. 5E shows a polyamidoamine (PAMAM) starburst dendrimer having amino surface groups conjugated with a plurality of isoluminol moieties according to another embodiment of the invention. FIG. 5F shows a polypropyleneimine (PEI) starburst dendrimer having amino surface groups conjugated with a plurality of isoluminol moieties according to a further embodiment of the invention.

Figure 5G:
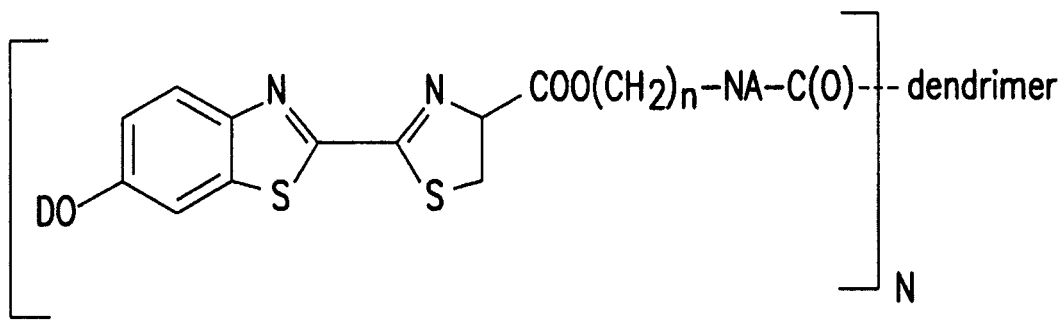
Figure 5H:
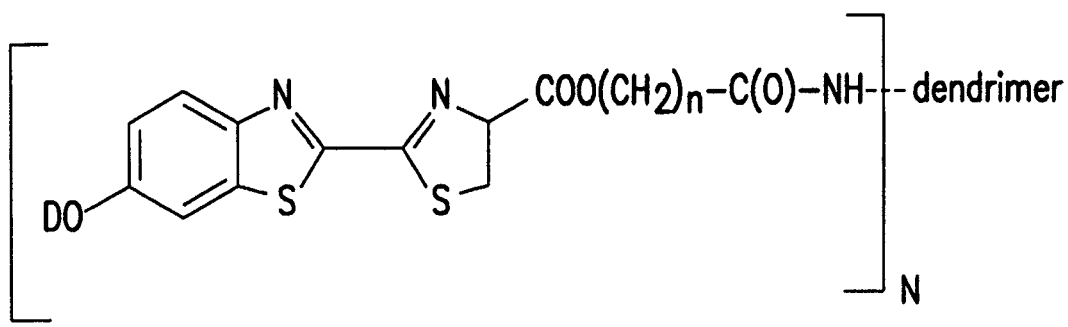
Figure 5I:
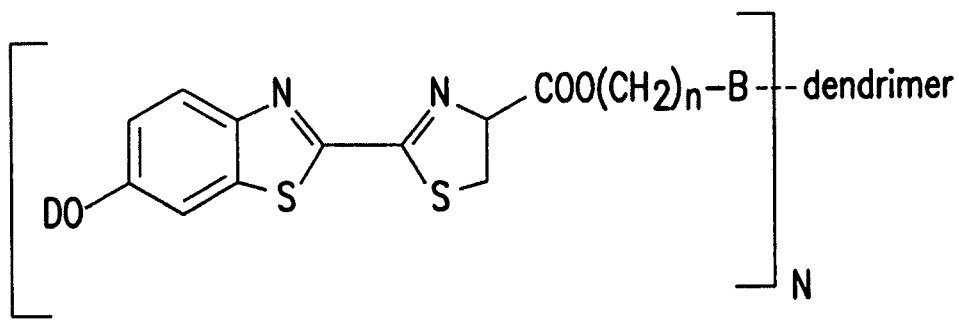

FIGS. 5G-5I show conjugates of dendrimers and luciferins according to the invention. In FIGS. 5G-5I, N is defined as set forth above. In FIG. 5G, the substituent A can be H or an alkyl group. In FIGS. 5G and 5H, the substituent D can be H or $PO_3H_2$. In FIG. 5I, the substituent B can be independently NA, O, S or $CH_2$ wherein the substituent A can be H or an alkyl group.

Figure 6A:
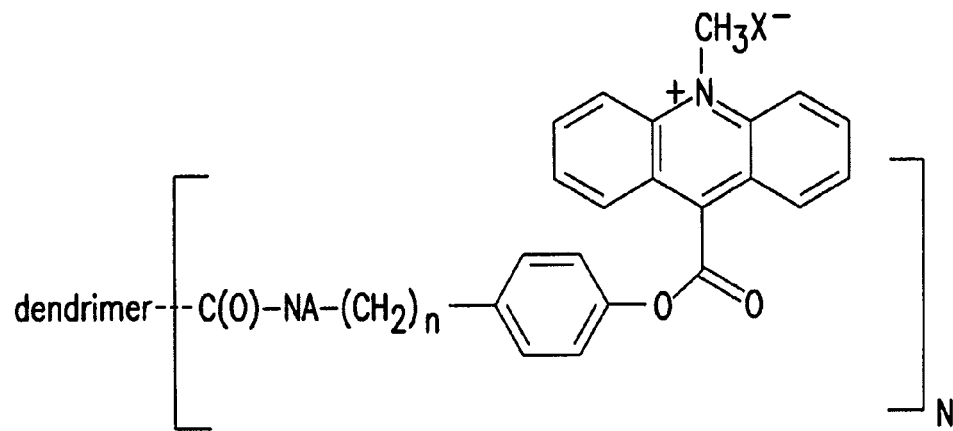
Figure 6B:
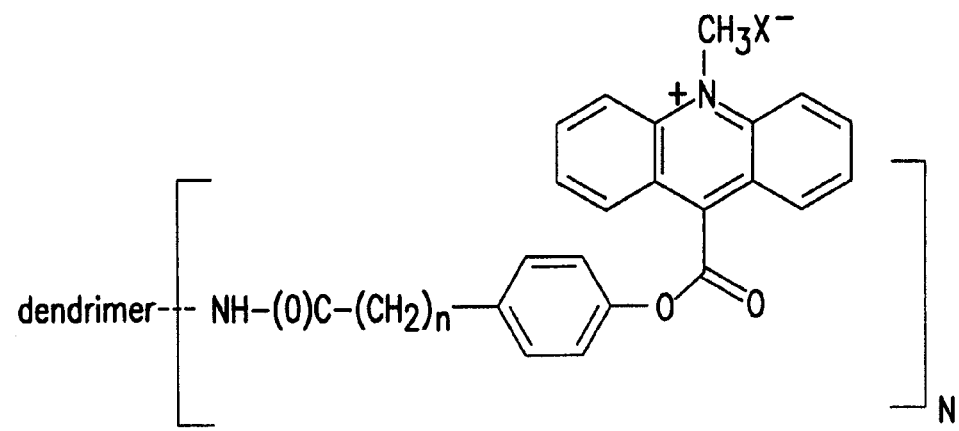
Figure 6C:
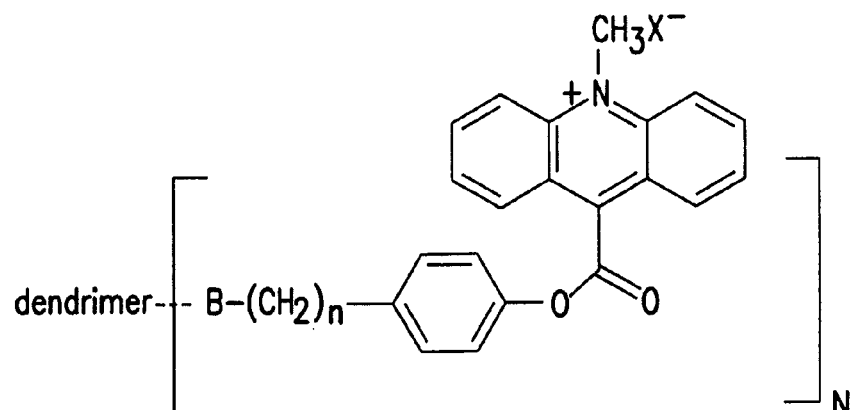

FIGS. 6A-6C show conjugates of dendrimers and acridinium esters according to the invention. In FIGS. 6A-6C, N is defined as set forth above and X is a counterion such as a halide or a triflate. In FIG. 6A, the substituent A can be H or an alkyl group. In FIG. 6C, the substituent B can be NA, NH, O, S or $CH_2$ wherein the substituent A can an alkyl or an aryl group.

Figure 6D:
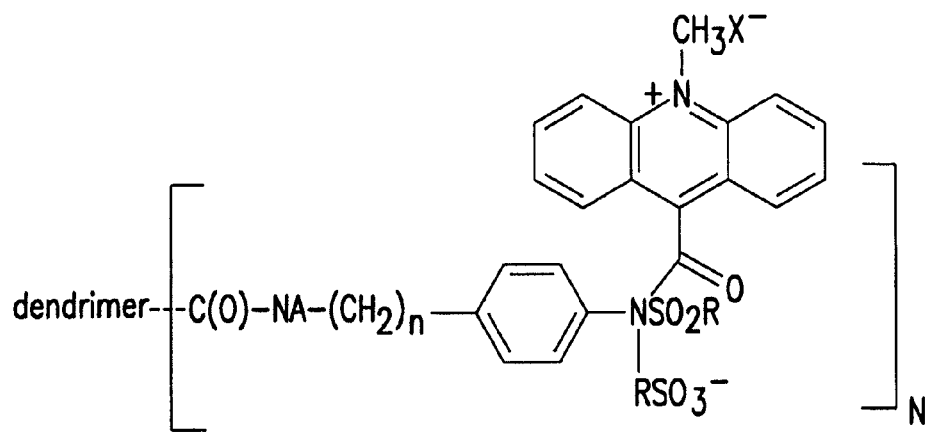
Figure 6E:
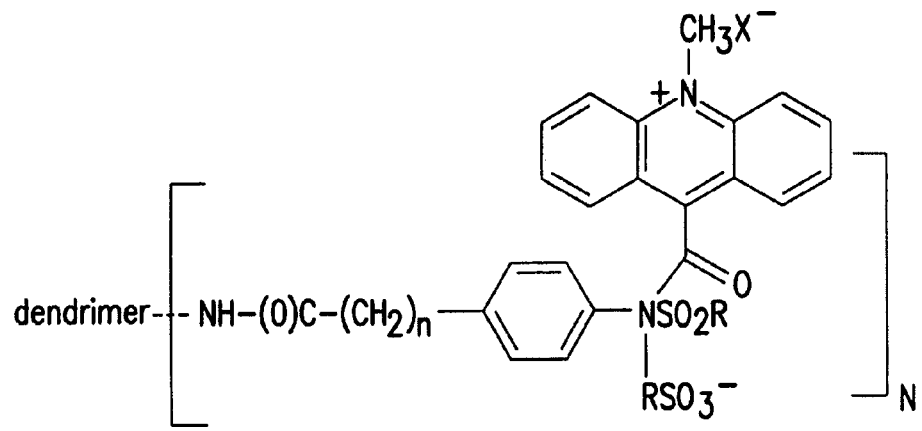
Figure 6F:
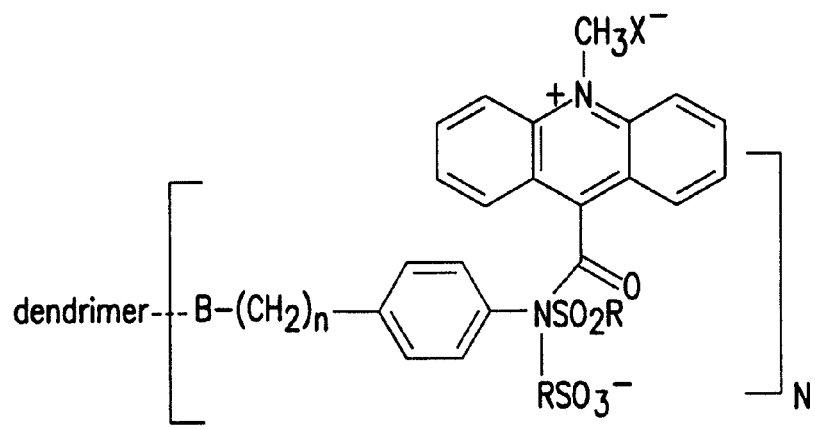
Figure 6G:
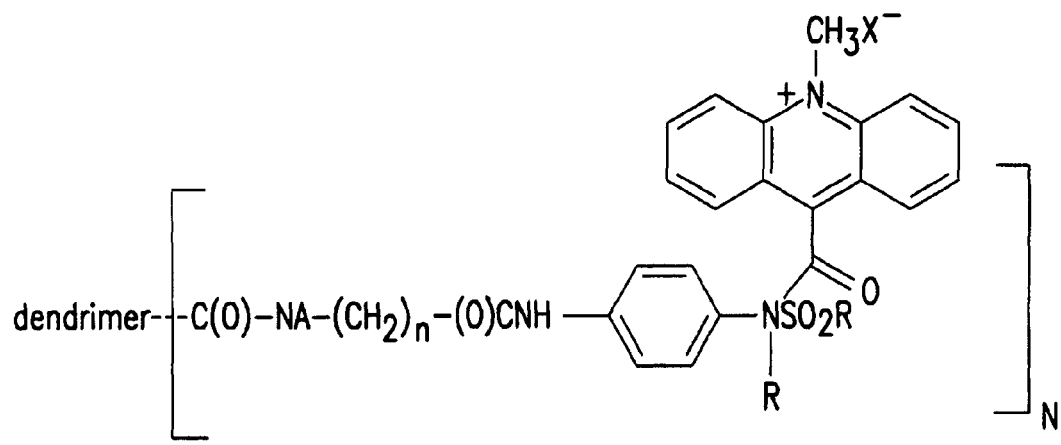
Figure 6H:
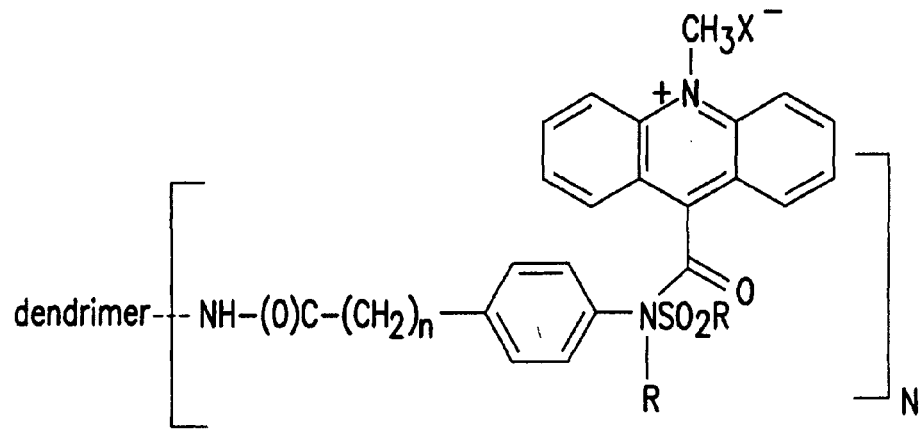
Figure 6:
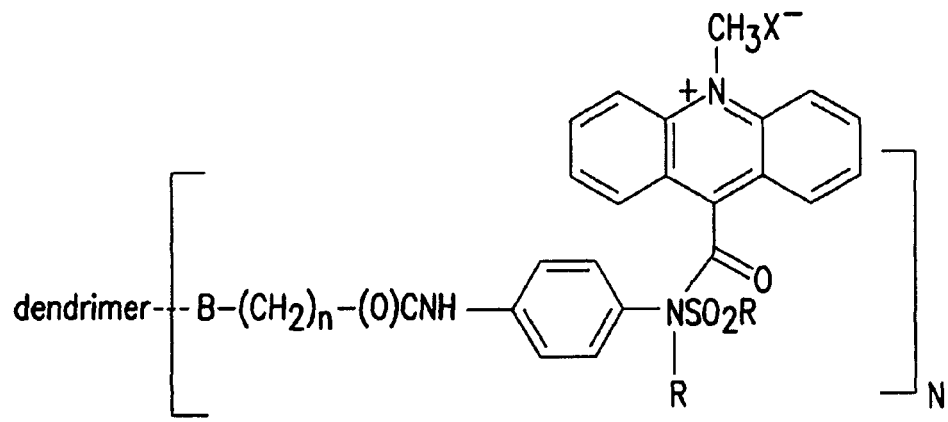

FIGS. 6D-6I show conjugates of dendrimers and acridinium sulfonylamides according to the invention. In FIGS. 6D-6I, N is defined as set forth above and X is a counterion such as a halide or a triflate. In FIGS. 6D and 6G, the substituent A can be H or an alkyl group. In FIGS. 6D, 6E, 6G and 6H, the substituent R can be an alkyl or an aryl group. In FIGS. 6F and 6I, the substituent B can be NA, NH, O, S or $CH_2$ wherein the substituent A can an alkyl or an aryl group.

Figure 6J:
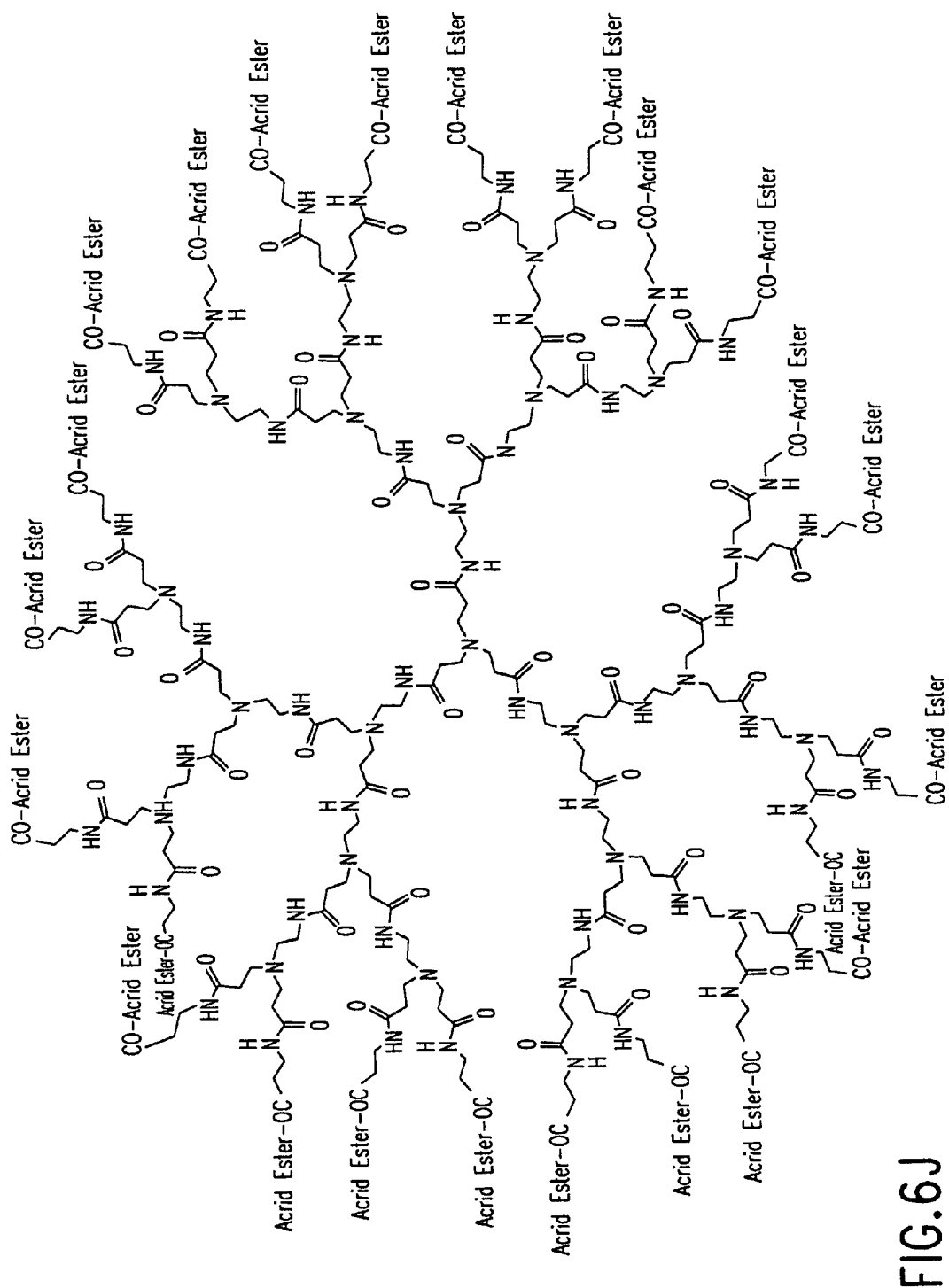
Figure 6K:
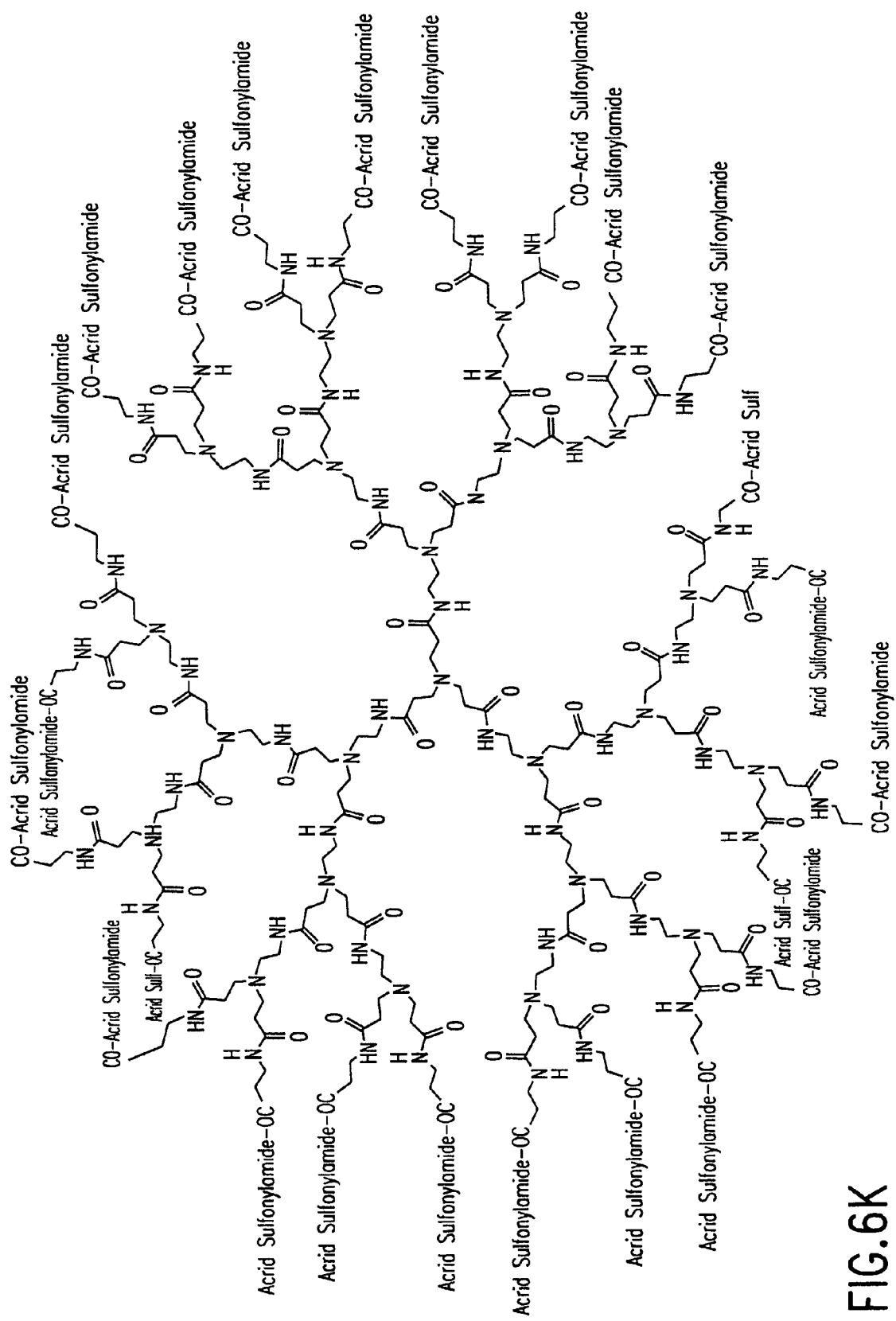
Figure 6L:
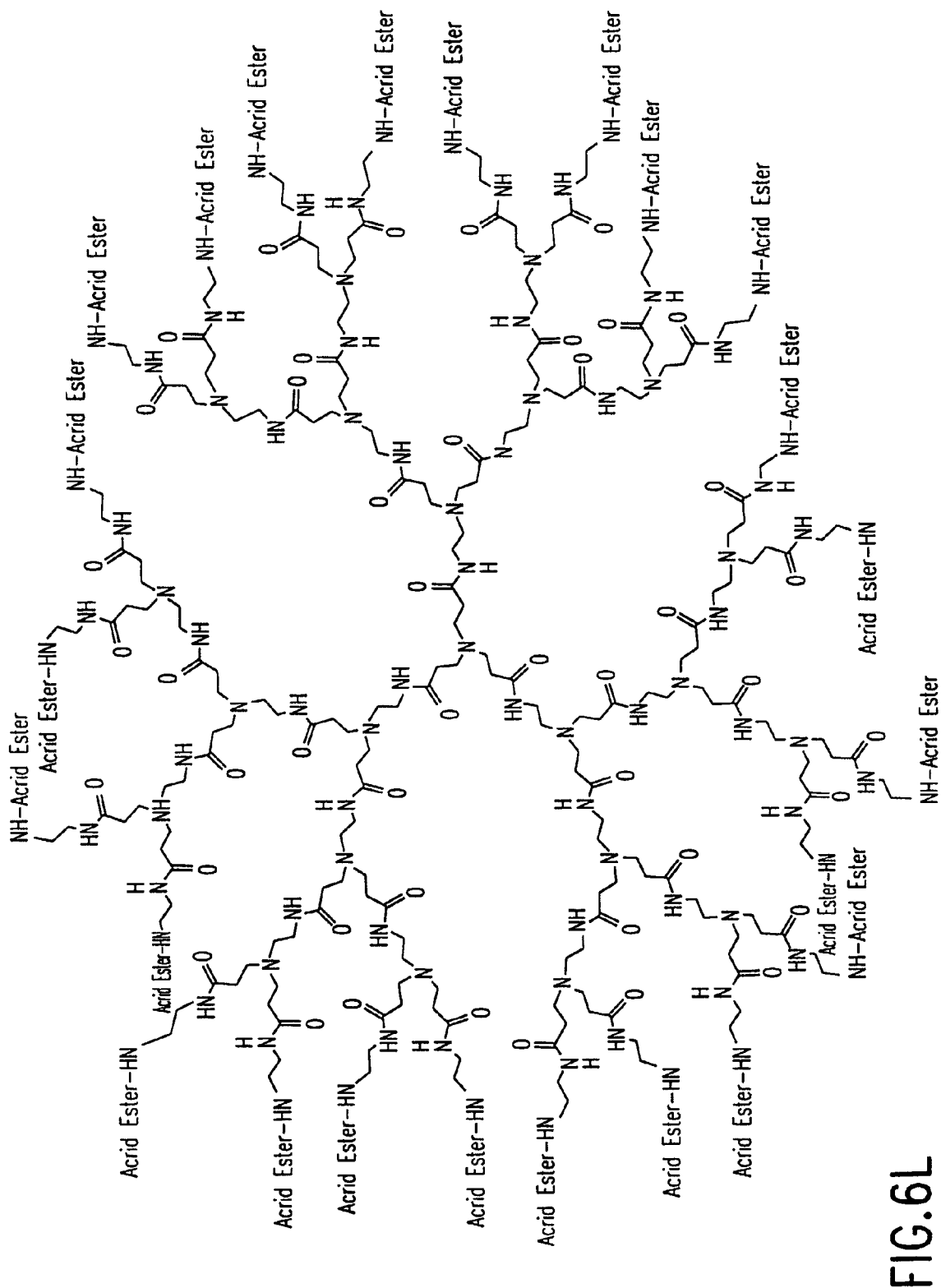
Figure 6M:
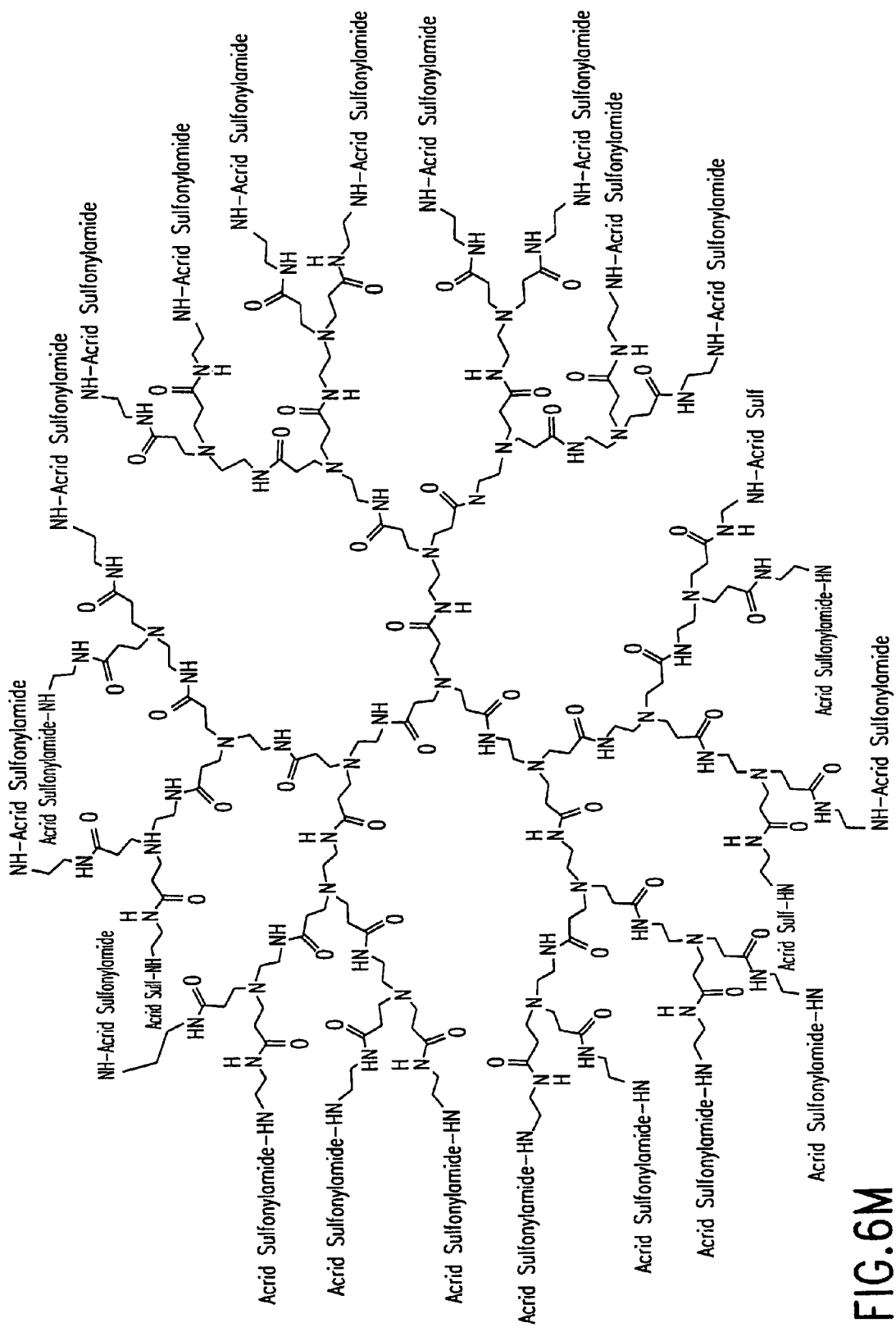
Figure 6N:
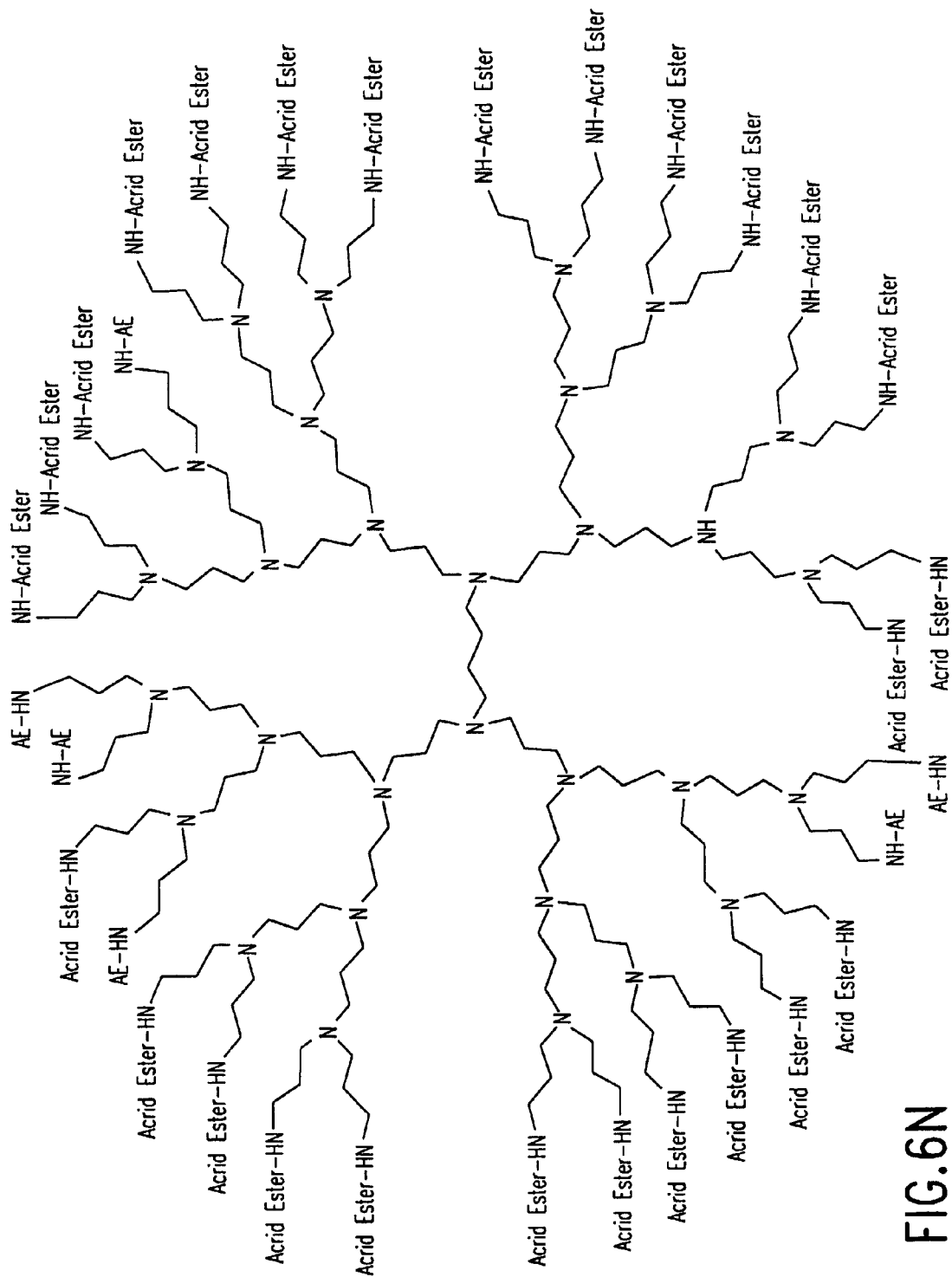
Figure 60:
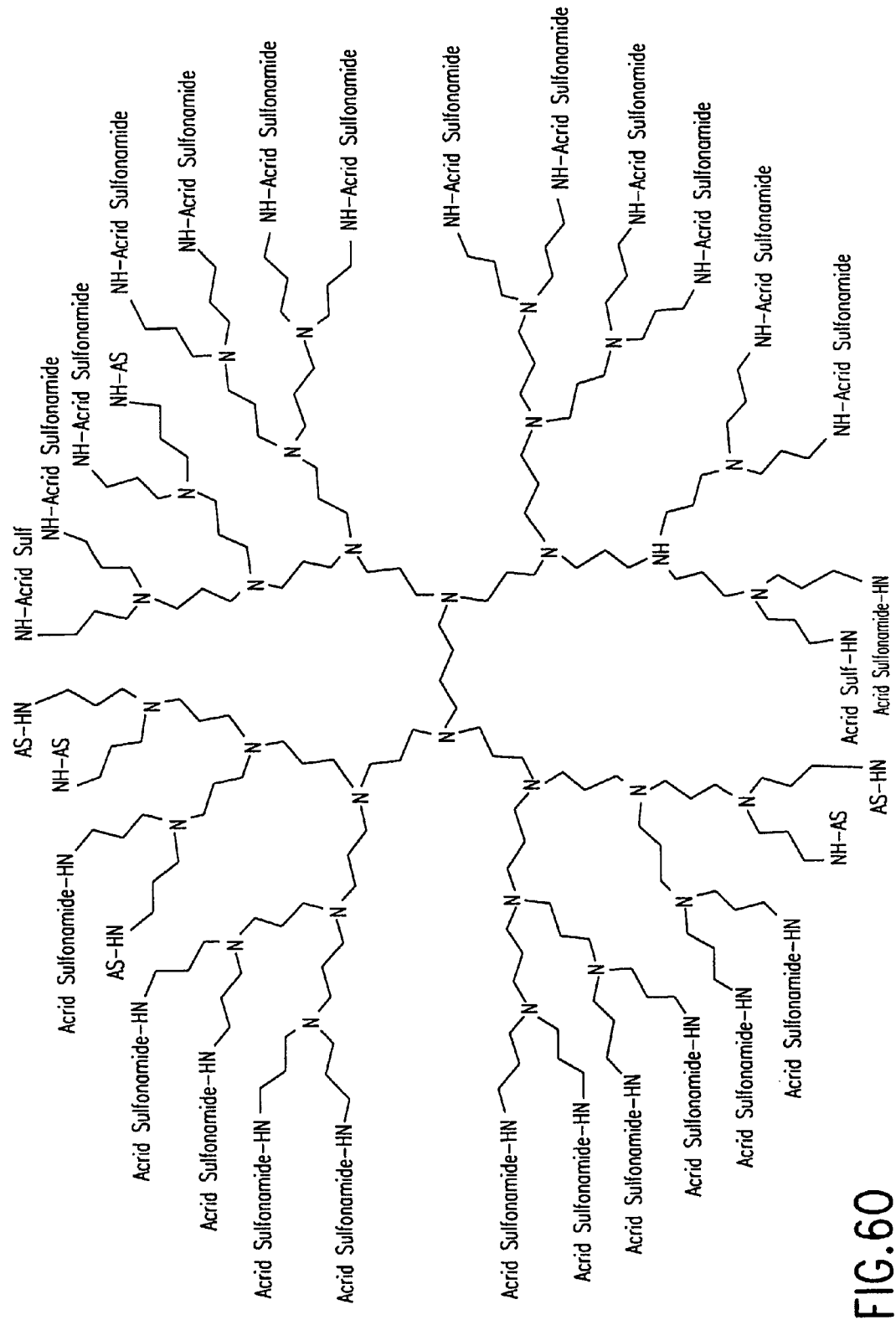

FIG. 6J shows a polyamidoamine (PAMAM) starburst dendrimer having carboxylic acid surface groups conjugated with a plurality of acridinium ester moieties according to an embodiment of the invention. FIG. 6K shows a polyamidoamine (PAMAM) starburst dendrimer having carboxylic acid surface groups conjugated with a plurality of acridinium sulfonamide moieties according to another embodiment of the invention. FIG. 6L shows a polyamidoamine (PAMAM) starburst dendrimer having amino surface groups conjugated with a plurality of acridinium ester moieties according to another embodiment of the invention. FIG. 6M shows a polyamidoamine (PAMAM) starburst dendrimer having amino surface groups conjugated with a plurality of acridinium sulfonamide moieties according to another embodiment of the invention. FIG. 6N shows a polypropyleneimine (PEI) starburst dendrimer having amino surface groups conjugated with a plurality of acridinium ester moieties according to a further embodiment of the invention. FIG. 6O shows a polypropyleneimine (PEI) starburst dendrimer having amino surface groups conjugated with a plurality of acridinium sulfonamide moieties according to a further embodiment of the invention.

Figure 6P:
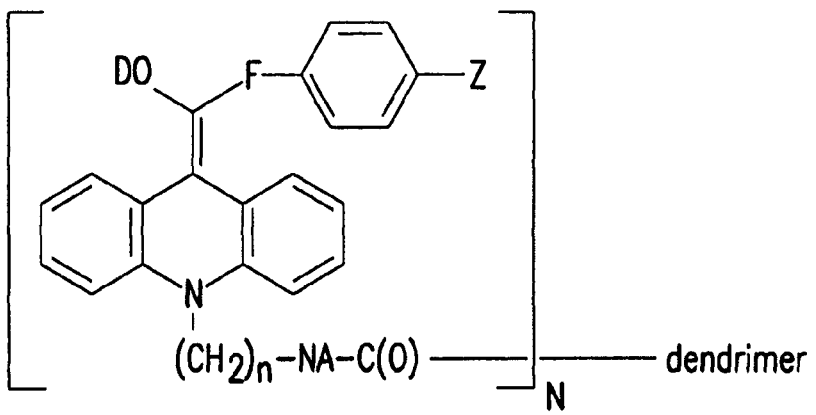
Figure 6Q:
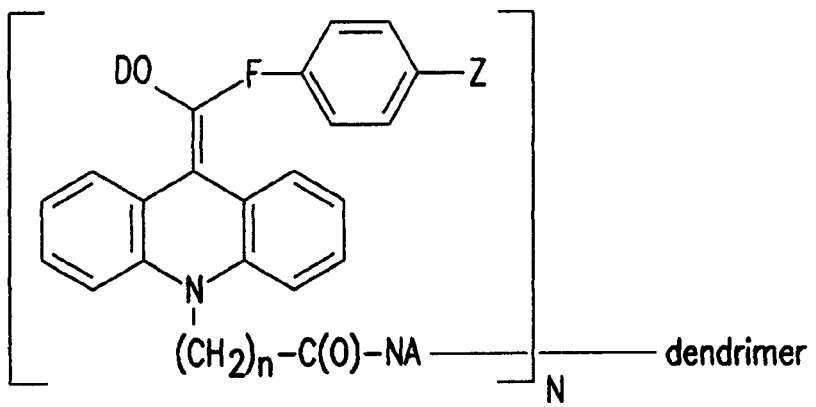
Figure 6R:
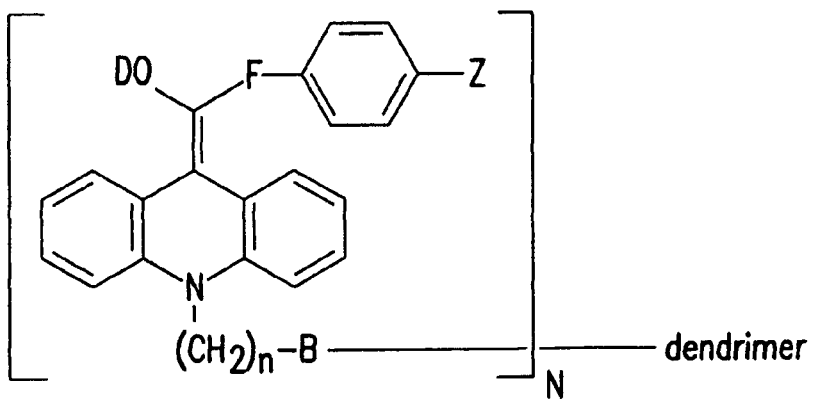

FIGS. 6P-6R show conjugates of dendrimers and acridan moieties according to the invention. In FIGS. 6P-6R, the substituent D can be $PO_3X_2$, a glycoside or a sulfate wherein X is a counterion such as a halide or ammonium. The substituent F can be NA, S or O wherein A can be H or an alkyl group. The substituent Z can be a halo, alkoxy or alkyl group. N is a positive integer. According to a preferred embodiment of the invention, N is an integer from 1 to 10. In FIG. 6R, the substituent B can be NA, O, S or $CH_2$ wherein A can be H or an alkyl group.

Figure 7A:
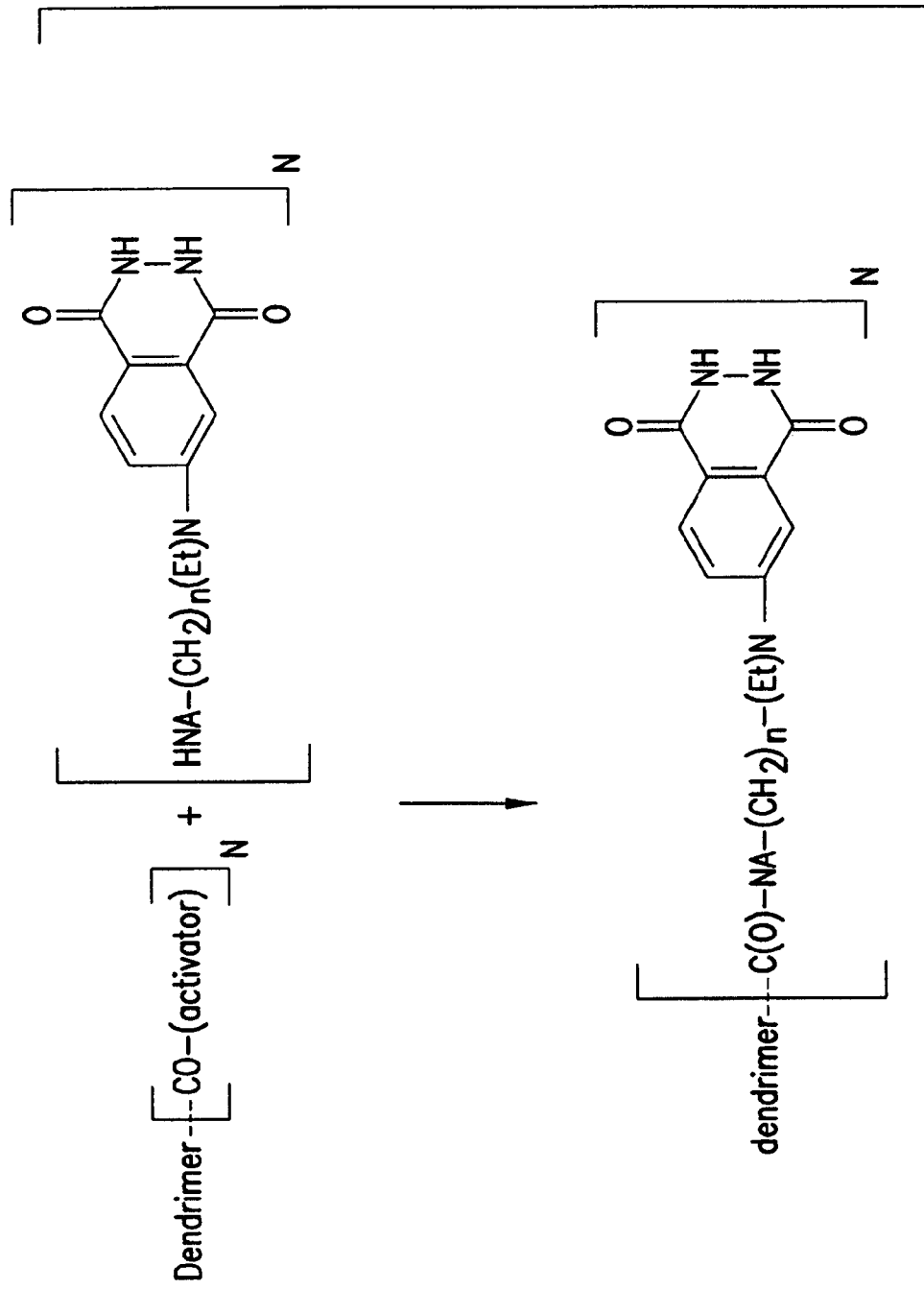
FIG. 7A-7C show the synthesis of dendritic polymer isoluminol conjugates according to the invention.
Figure 7B:
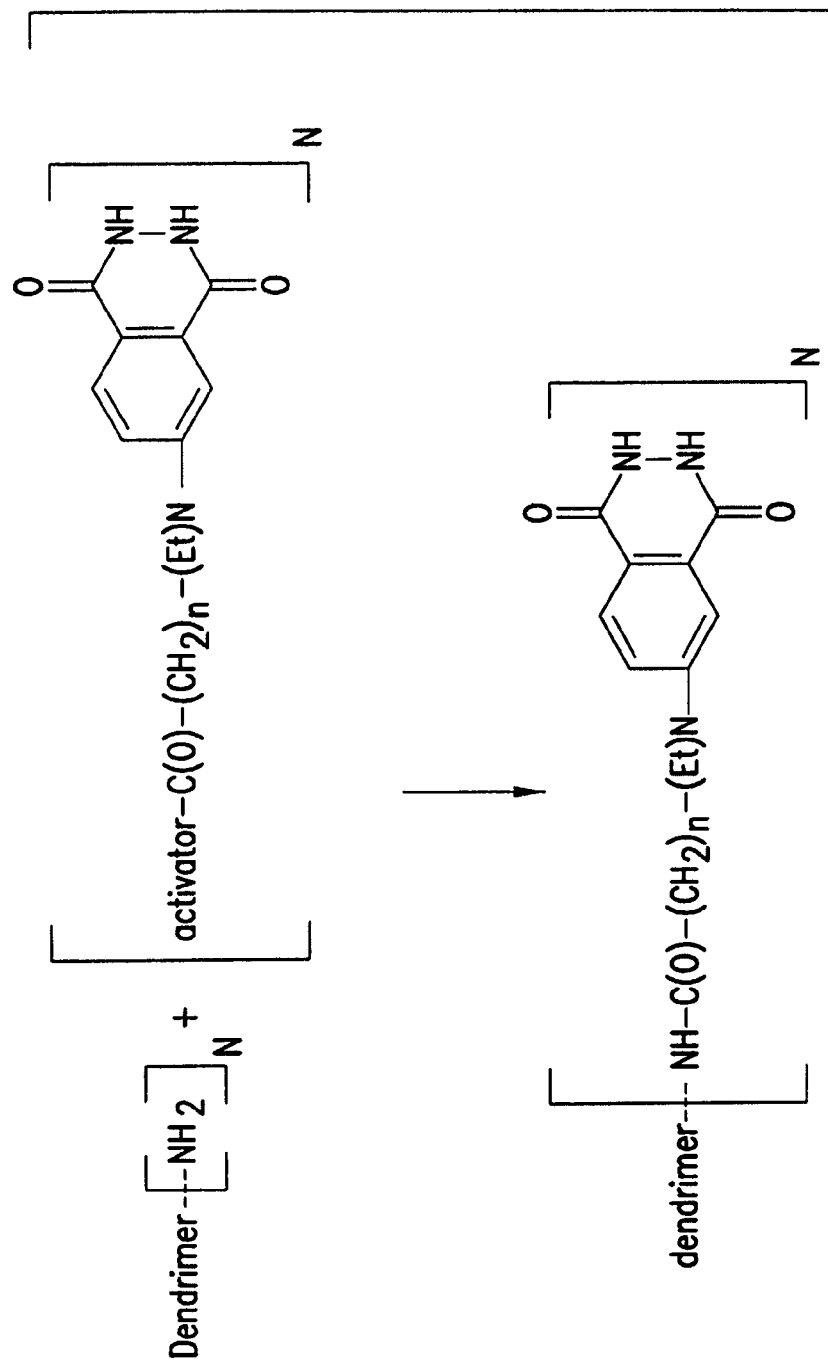
Figure 7C:
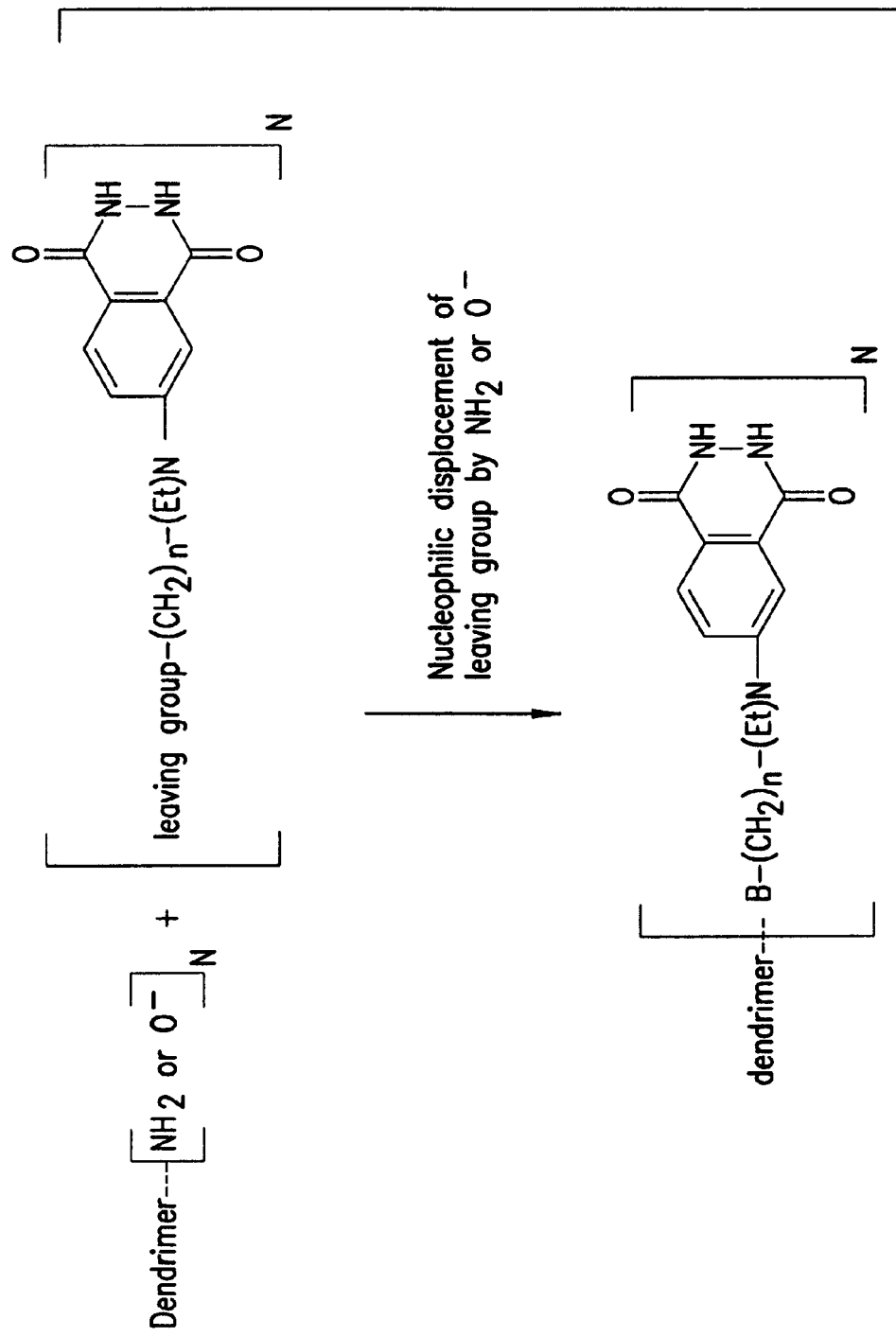

FIGS. 7A-7C show the synthesis of dendritic polymer isoluminol conjugates according to the invention. In FIGS. 7A-7C, "N", which represents the number of chemiluminescent substrates conjugated to the dendrimer, is a positive integer and "n" is 0 or a positive integer. In FIGS. 7A and 7B, "activator" can be a mixed anhydride, an NHS ester or another standard functionality used in peptide chemistry to facilitate peptide bond formation. In FIG. 7A, "A" can be H or an alkyl group. In FIG. 7C, "B" can be NH or O, and "leaving group" can be a halogen or sulfonic acid ester such as a mesylate, a tosylate or a triflate. According to a preferred embodiment of the invention, N in FIGS. 7A-7C is an integer from 6 to 768.

Figure 8A:
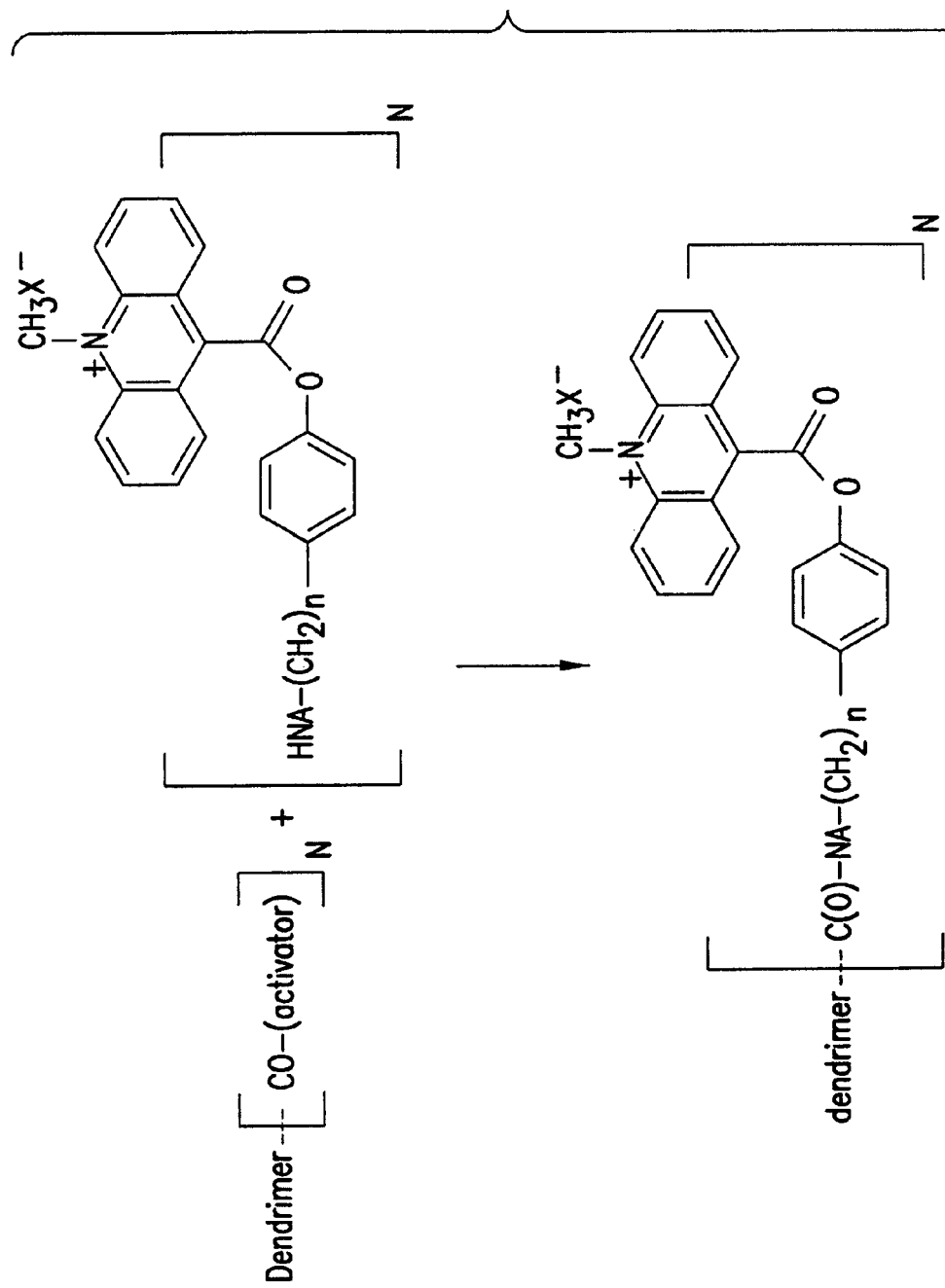
FIG. 8A-8F show synthesis of dendritic polymer acridinium ester and acridinium sulfonylamide conjugates according to the invention.
Figure 8B:
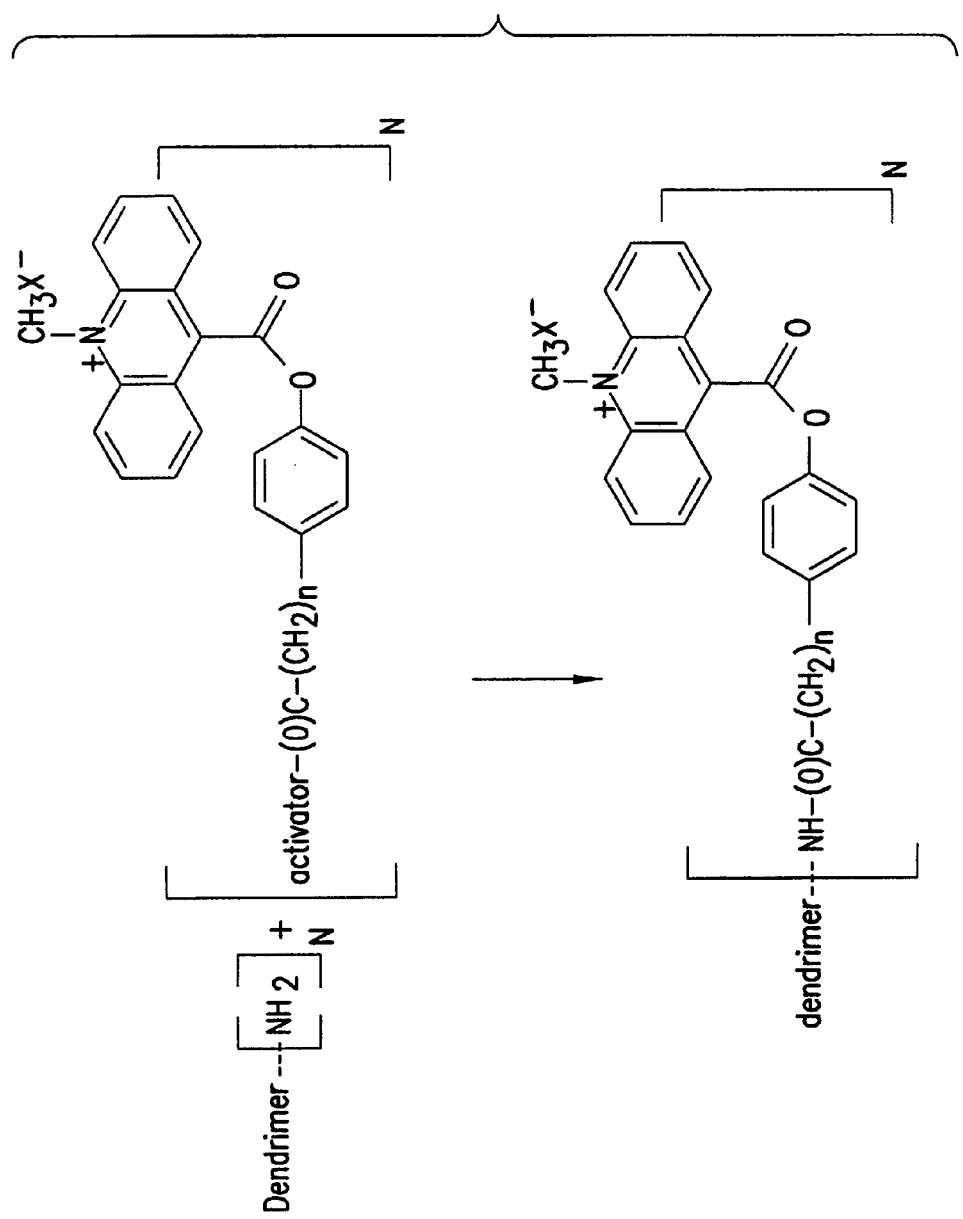
Figure 8C:
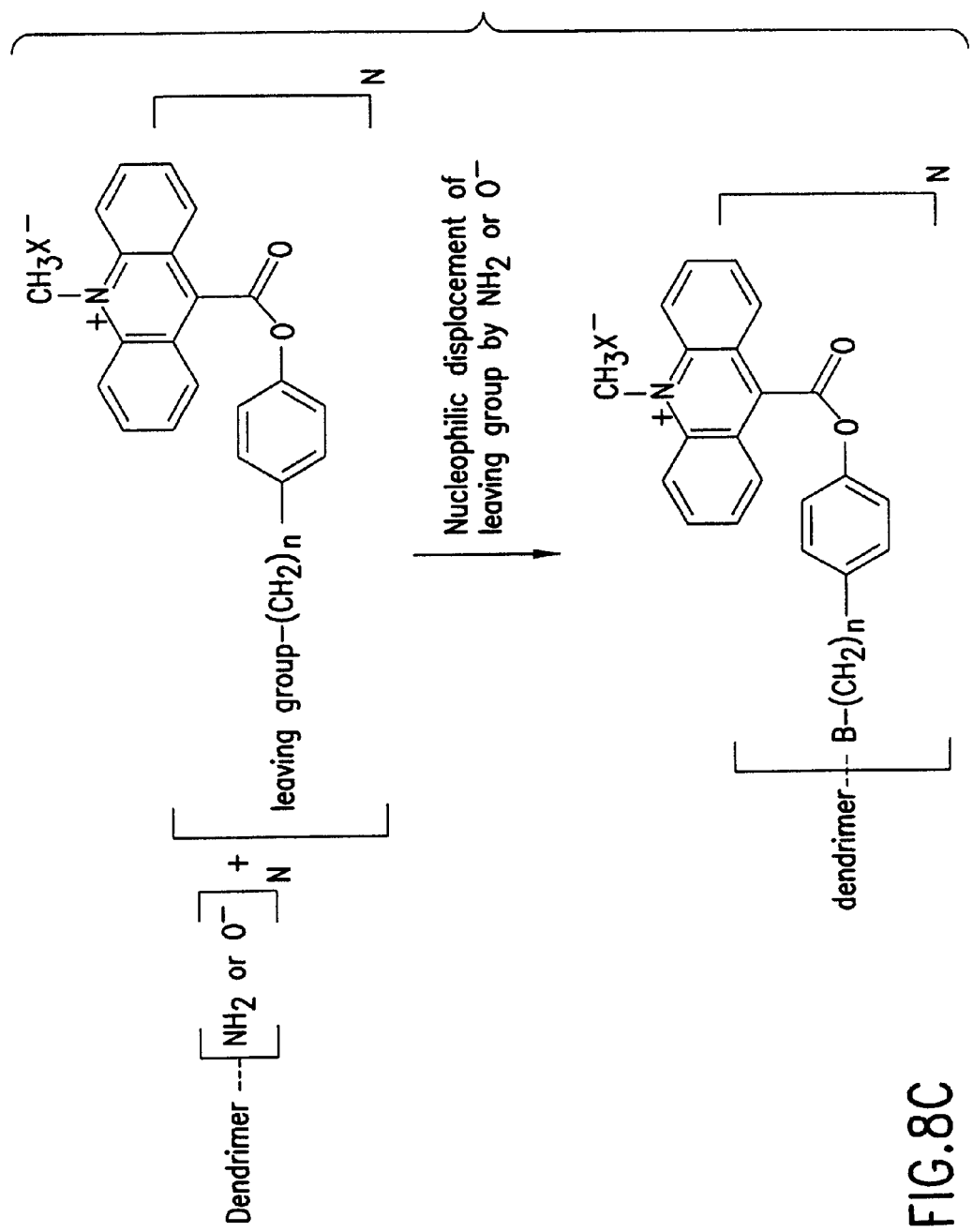
Figure 8D:
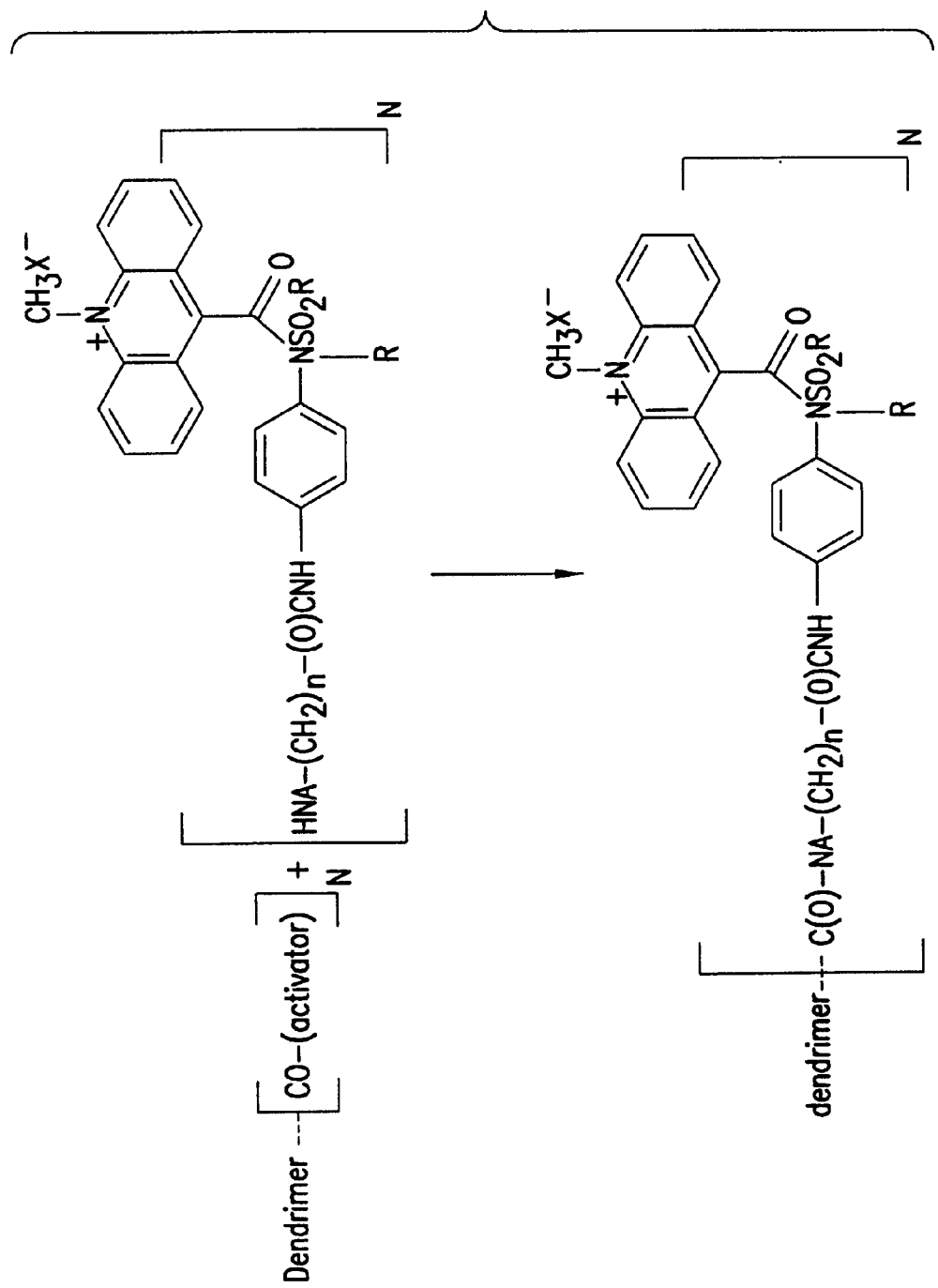
Figure 8E:
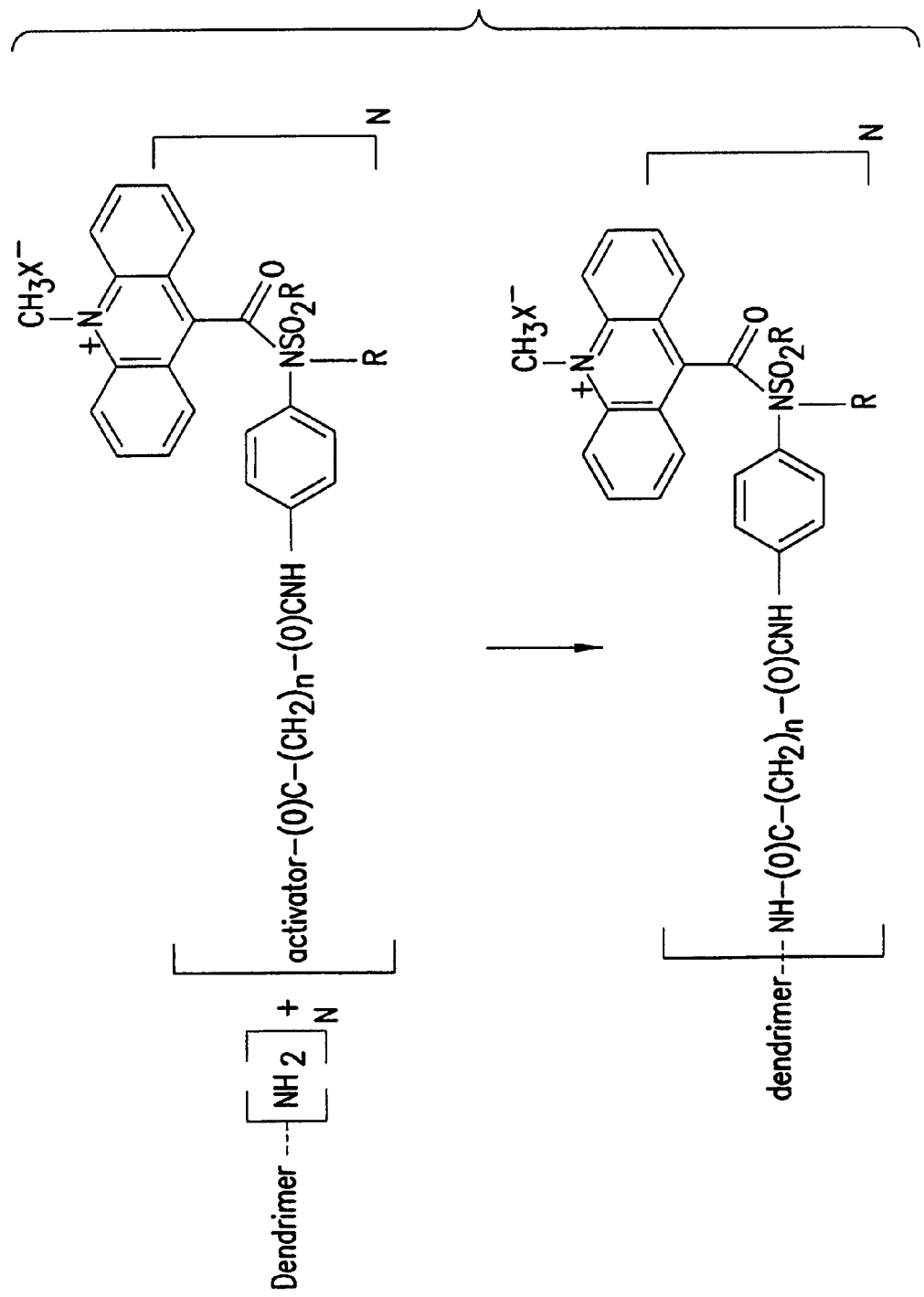
Figure 8F:
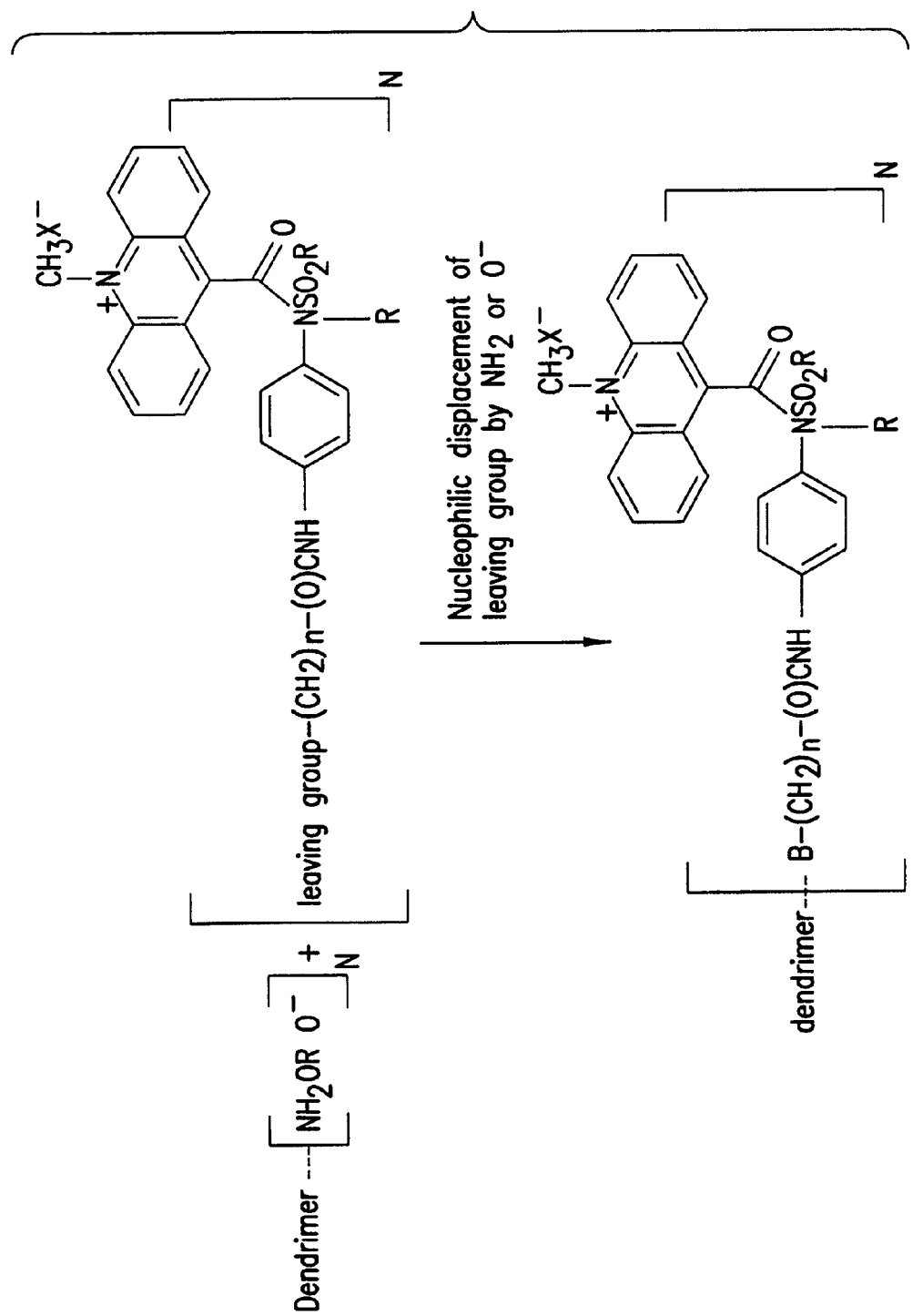

FIGS. 8A-8F show synthesis schemes for a number of dendritic polymer acridinium conjugates. FIGS. 8A-8C show the synthesis of dendritic polymer acridinium ester conjugates according to the invention and FIGS. 8D-8F show the synthesis of dendritic polymer acridinium sulfonylamide conjugates according to the invention. In FIGS. 8A-8F: X represents a counterion such as a halide or a triflate; "N", which represents the number of chemiluminescent substrates conjugated to the dendrimer, is a positive integer; and "n" is 0 or a positive integer. According to a preferred embodiment of the invention, N in FIGS. 8A-8F is an integer from 6 to 768.

In FIGS. 8A, 8B, 8D and 8E, "activator" can be a mixed anhydride, an NHS ester or another standard functionality used in peptide chemistry to facilitate peptide bond formation. In FIGS. 8A and 8D, "A" can be H or an alkyl group. In FIGS. 8C and 8F: "B" can be NH or O; and "leaving group" can represent a halogen or sulfonic acid ester such as a mesylate, a tosylate or a triflate. In FIGS. 8D-8F, the substituent "R" can be an alkyl or an aryl group.

Figure 9A:
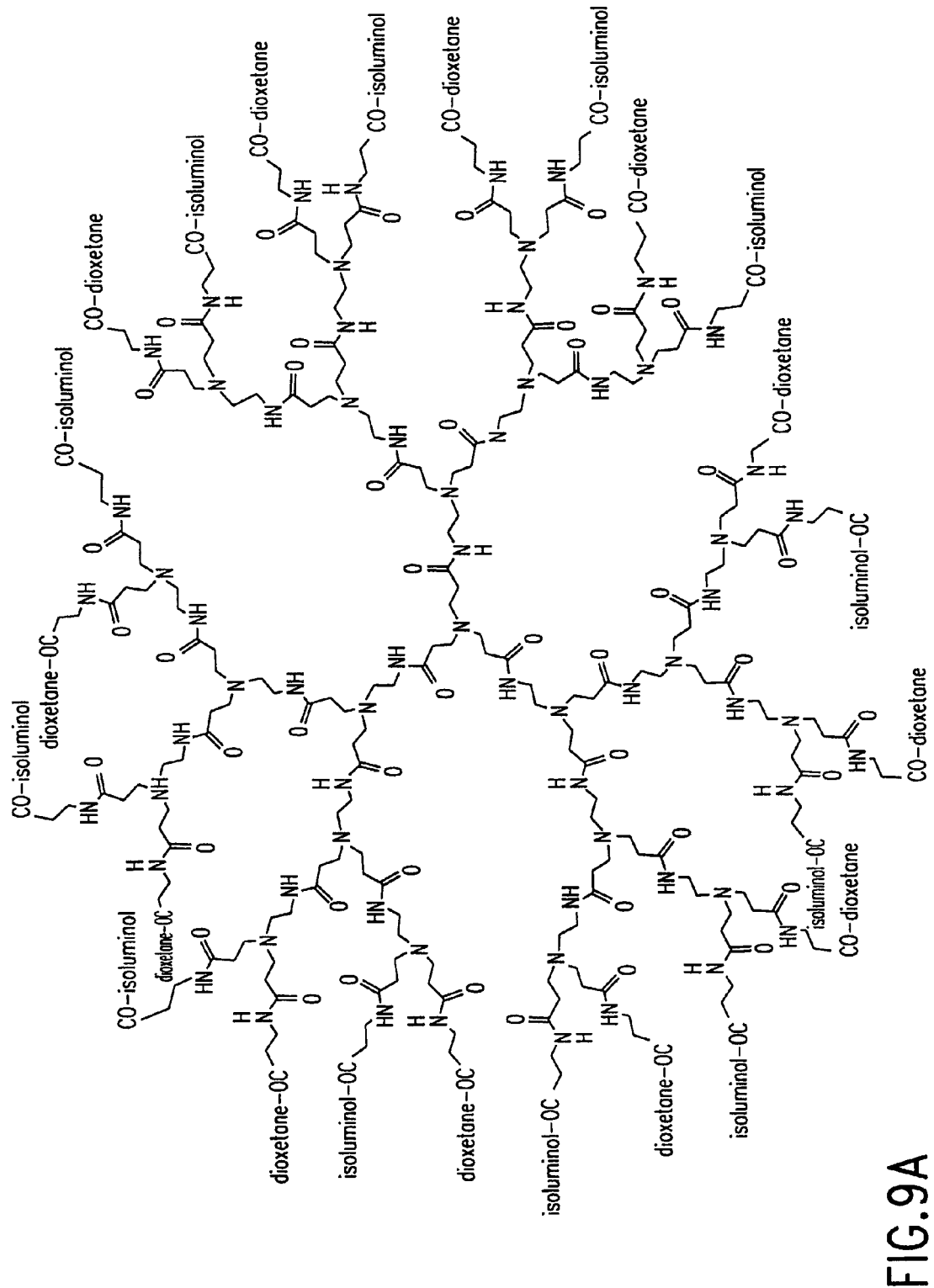
FIG. 9A-9C show dendritic polymer dioxetane and isoluminol, dioxetane and acridinium ester, and dioxetane and acridinium sulfonylamide conjugates according to the invention.
Figure 9B:
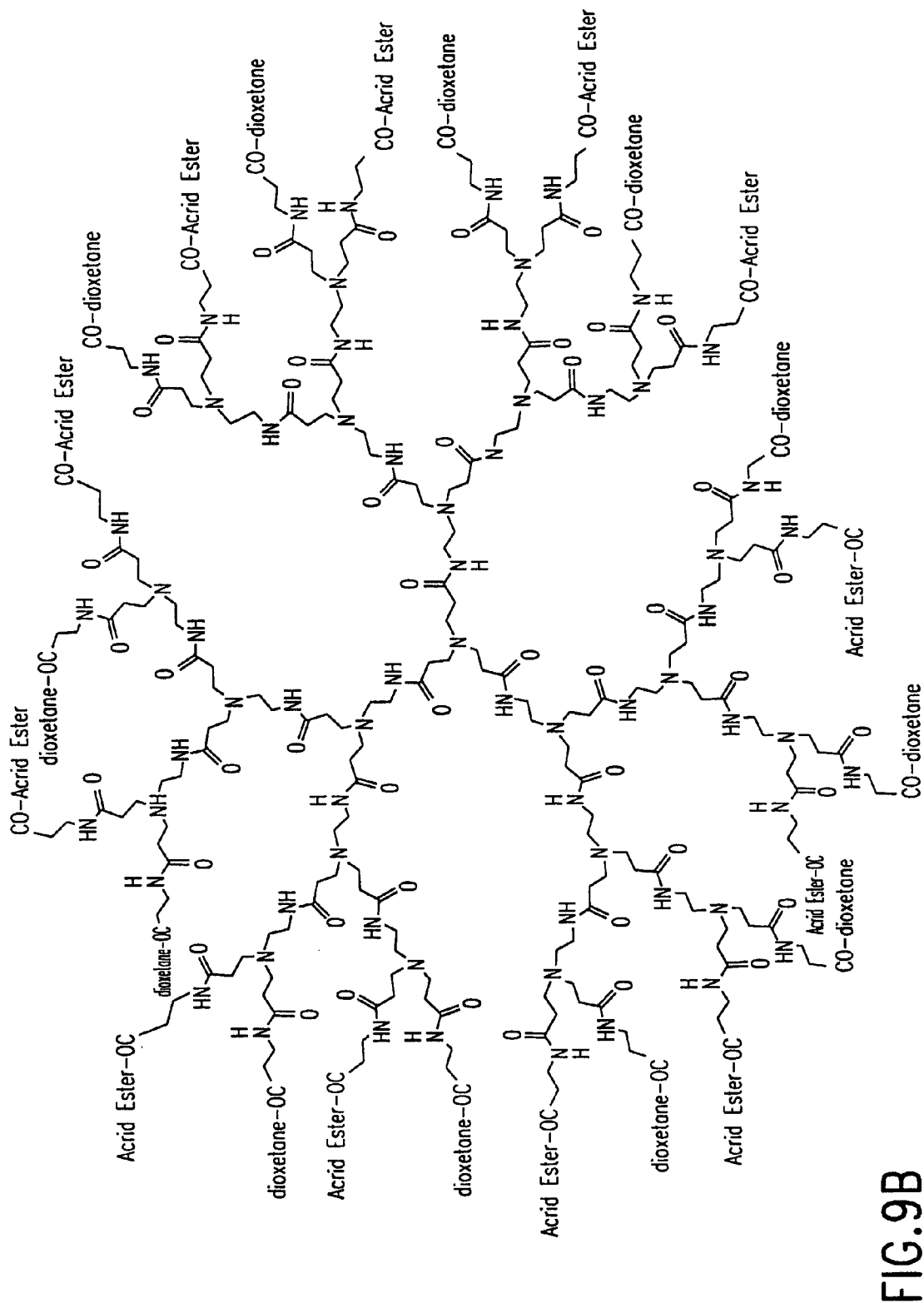
Figure 9C:
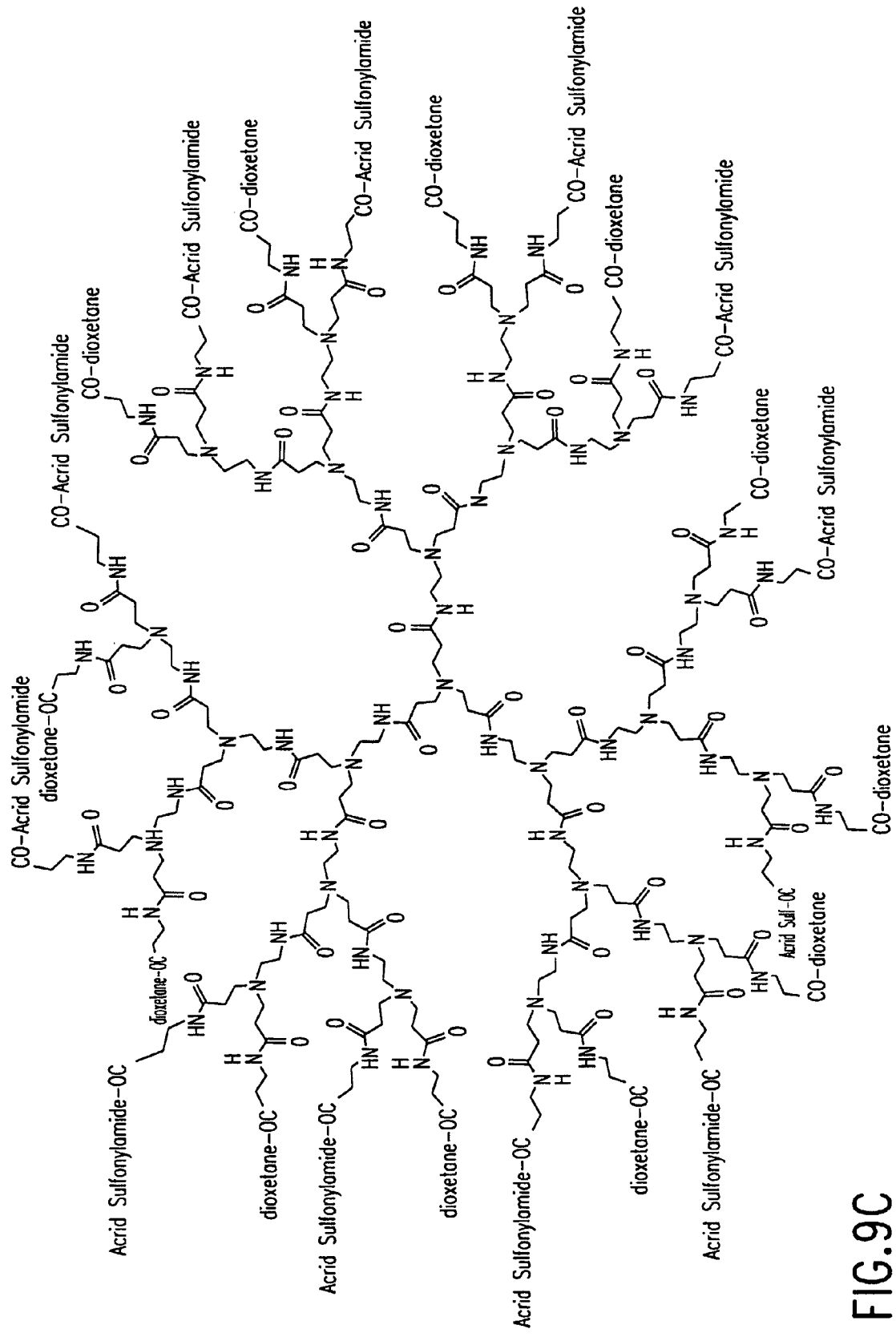

It may also be desirable to couple two or more different chemiluminescent substrates to a dendrimer backbone. Examples of such dendritic polymer dual enzyme label chemiluminescent substrates are shown in FIGS. 9A-9C. FIG. 9A shows a polyamidoamine (PAMAM) starburst dendrimer conjugated with dioxetane and isoluminol moieties according to an embodiment of the invention. FIG. 9B shows a polyamidoamine (PAMAM) starburst dendrimer conjugated with dioxetane and acridinium ester moieties according to a further embodiment of the invention. FIG. 9C shows a polyamidoamine (PAMAM) starburst dendrimer conjugated with dioxetane and acridinium sulfonamide moieties according to a further embodiment of the invention.

Figure 10:
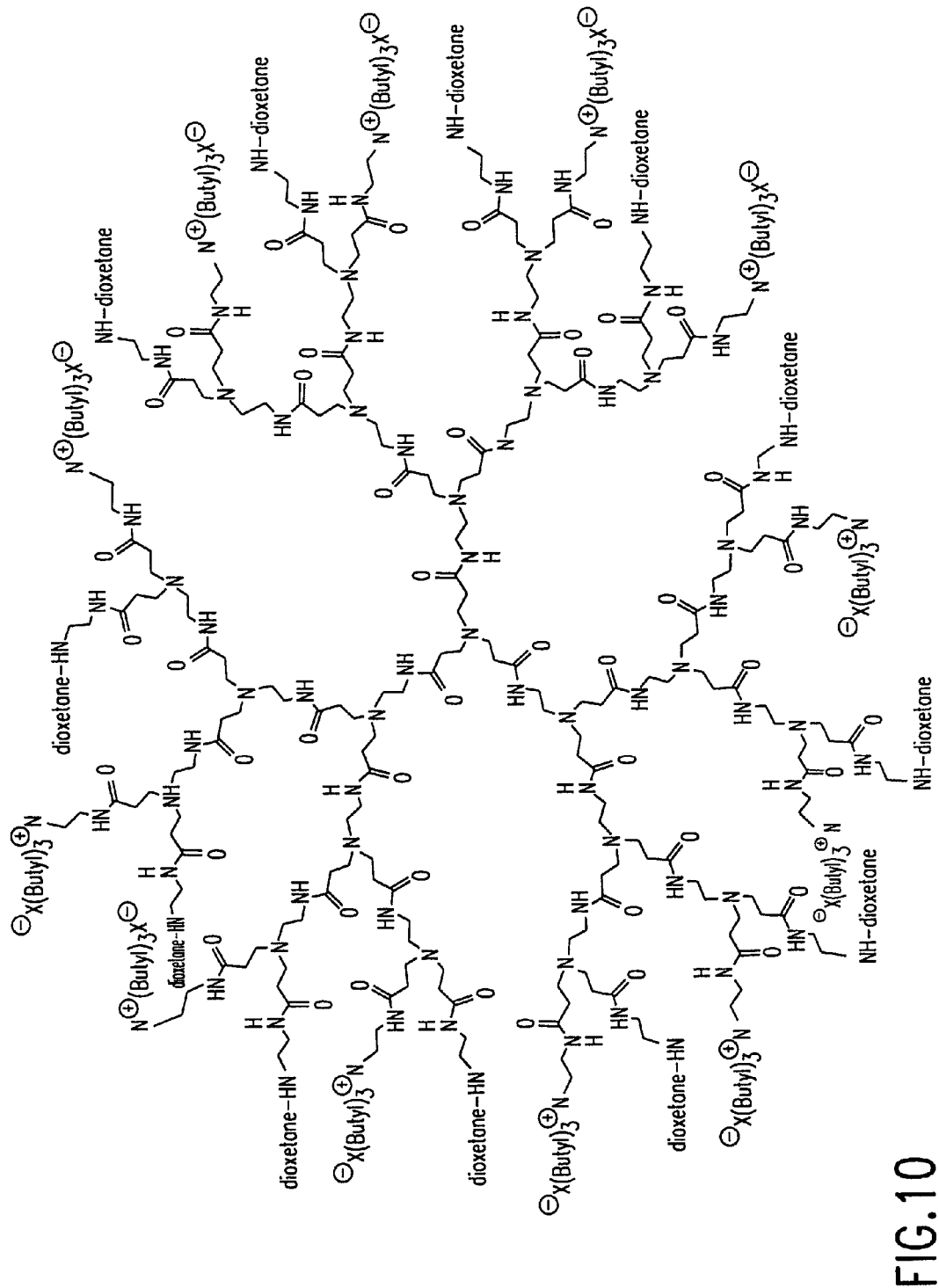
FIG. 10 shows linked dioxetanes and quaternary amino enhancers according to the invention.

FIG. 10 shows a polyamidoamine (PAMAM) dendrimer having amino surface groups conjugated to dioxetane moieties and quarternary ammonium enhancer moieties according to an embodiment of the invention. As shown in FIG. 10, the quarternary ammonium enhancer moieties are perbutylated ammonium moieties.

Figure 11:
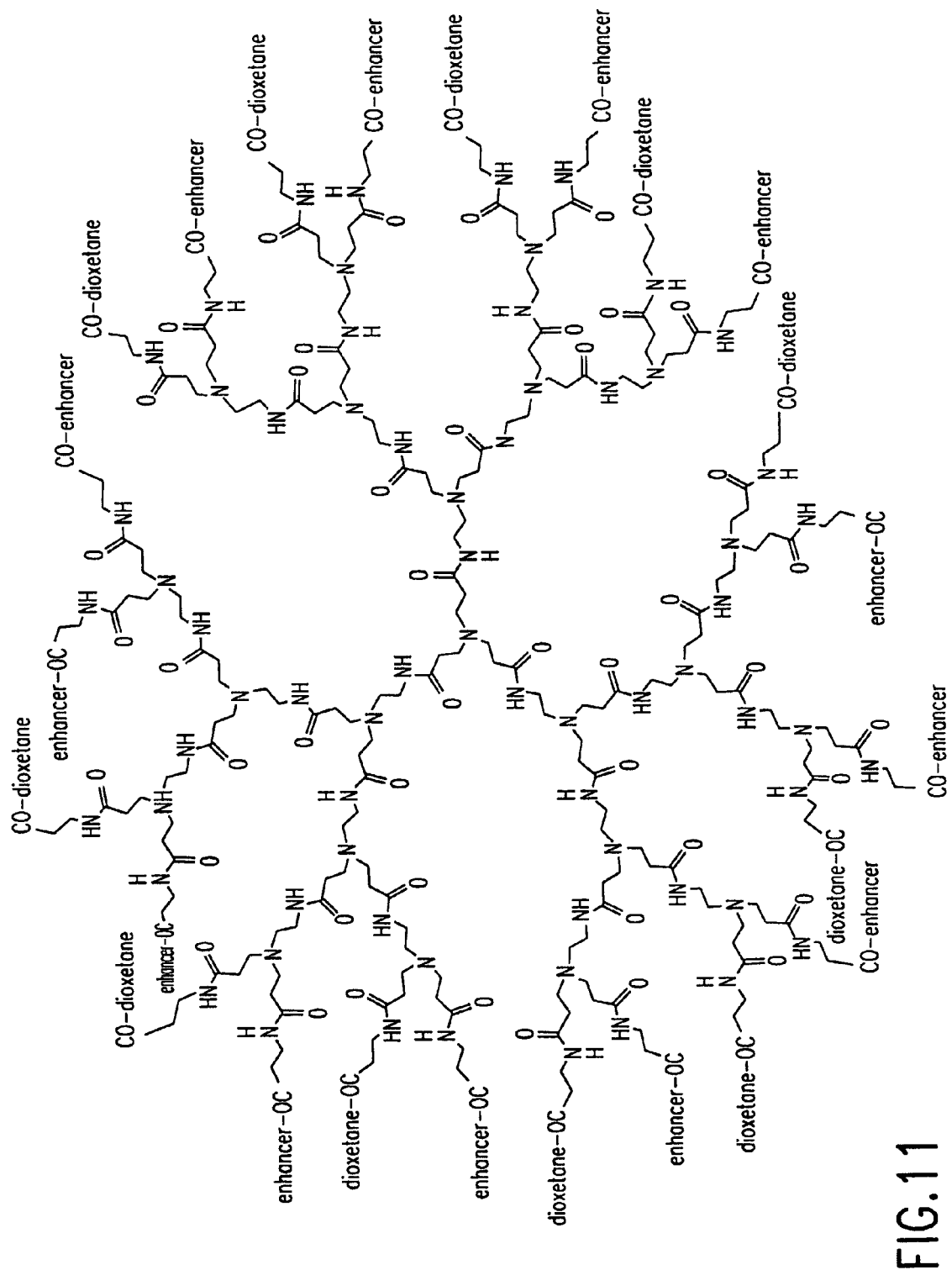
FIG. 11 shows dendritic dioxetane enhancer hybrids according to the invention.

FIG. 11 shows a polyamidoamine (PAMAM) dendrimer having carboxylic acid surface groups conjugated to both dioxetane moieties and enhancer moieties according to a further embodiment of the invention. The enhancer moieties according to the invention can be: amino terminated polymeric quaternary ammonium, phosphonium or sulfonium salts; amino terminated quaternized Jeffamines; amino terminated quaternized polyethyleneimines; or amino terminated poly (2-, 3-, or 4-vinylpyridinium) salts.

A "dendritic polymer" is a polymer exhibiting regular dendritic branching, formed by the sequential or generational addition of branched layers to or from a core. The term dendritic polymer encompasses "dendrimers," which are characterized by a core, at least one interior branched layer, and a surface branched layer. (See Petar R. Dvornic and Donald A. Tomalia in Chem. in Britain, 641-645, August 1994.) A "dendron" is a species of dendrimer having branches emanating from a focal point which is or can be joined to a core, either directly or through a linking moiety to form a dendrimer. Many dendrimers comprise two or more dendrons joined to a common core. However, the term dendrimer is used broadly to encompass a single dendron.

Dendritic polymers include, but are not limited to, symmetrical and unsymmetrical branching dendrimers, cascade molecules, arborols, and the like, though the most preferred dendritic polymers are dense star polymers. The PAMAM dense star dendrimers disclosed herein are symmetric, in that the branch arms are of equal length. The branching occurs at the hydrogen atoms of a terminal —$NH_2$ group on a preceding generation branch.

Even though not formed by regular sequential addition of branched layers, hyperbranched polymers, e.g., hyperbranched polyols, may be equivalent to a dendritic polymer where the branching pattern exhibits a degree of regularity approaching that of a dendrimer.

Topological polymers, with size and shape controlled domains, are dendrimers that are associated with each other (as an example covalently bridged or through other association as defined hereafter) through their reactive terminal groups, which are referred to as "bridged dendrimers." When more than two dense star dendrimers are associated together, they are referred to as "aggregates" or "dense star aggregates."

Therefore, dendritic polymers include bridged dendrimers and dendrimer aggregates. Dendritic polymers encompass both generationally monodisperse and generationally polydisperse solutions of dendrimers. The dendrimers in a monodisperse solution are substantially all of the same generation, and hence of uniform size and shape. The dendrimers in a polydisperse solution comprise a distribution of different generation dendrimers.

Dendritic polymers also encompass surface modified dendrimers. For example, the surface of a PAMAM dendrimer may be modified by the addition of an amino acid (e.g., lysine or arginine).

Several general coupling schemes may be employed to link chemiluminescent substrate precursors to dendritic polymers. A first method involves reacting primary or secondary amino-linked precursors such as alkenes or enol ethers (i.e., for the preparation of dioxetanes), luminols, isoluminols or acridinium esters or acridinium sulfonylamides with a carboxylate-terminated dendritic polymer that is activated as a mixed anhydride or an activated ester, or activated with a coupling agent such as carbodiimides, phosphonium or ammonium salts, to form an amide bond. Alternatively, an amino-terminated dendritic polymer can react with activated ester-linked chemiluminescent substrate precursor to form amide bonds. These types of amide bond forming reactions are well documented in the peptide synthetic literature and can be readily carried out by one skilled in the art. A second method involves forming ether or amine linkages by nucleophilic displacement of a leaving group, such as a halide or a sulfonic ester, on the chemiluminescent substrate precursor linker by dendritic polymer amino or alkoxide end groups. Similarly, the same type of linkage can be synthesized by nucleophilic displacement of leaving groups on the dendritic polymer surface by amine- or alkoxide-terminated linkers having attached chemiluminescent substrate precursors. A third method, well known in dye chemistry, involves coupling 1-2 dendritic polymer surface groups to cyanuric chloride, with the remaining 1-2 reactive chlorides on cyanuric chloride displaced by an amino-, sulfhydryl-, hydroxyl- or phenoxy-terminated linker on the chemiluminescent substrate precursor. A fourth method conjugates avidin- or streptavidin-linked chemiluminescent substrate precursors to biotinylated dendrimers, or conversely, conjugates biotinylated chemiluminescent substrate precursors to avidin- or streptavidin-modified dendrimers. Any known linker attached with standard coupling methods described in the literature can be used to couple chemiluminescent substrate precursors to dendritic polymers; the linkers and coupling methods described above serve only as examples. Appropriate coupling agents and conditions can be chosen and readily prepared by one skilled in the art.

After the dendritic polymer and chemiluminescent substrate precursors have been coupled, the chemiluminescent substrate precursors can be modified to form the dendritic polymer chemiluminescent substrates. For example, to complete the synthesis of dendritic polymer dioxetane, the linked precursor enol ethers are photooxygenated to the corresponding dioxetanes and any modifications to complete formation of the enzyme-cleavable groups, such as deprotection of triester phosphates to monoester phosphates or deacylation to the β-galactoside ethers, are carried out. If desired for dioxetane stability and/or enhanceability, the dendrimer-enol ether conjugates may be peralkylated with an arylalkyl or alkylhalide at any amino sites before proceeding with oxidation to the dioxetane.

The dendritic polymer chemiluminescent substrate conjugates described above show improved light intensity and/or sensitivity, as well as improved signal resolution. These substrate conjugates are specifically prepared for use in enzymatic assays, where hydrolytic enzymatic removal of enzyme labile (e.g., X) substituent on the dendritic polymer dioxetane conjugates (e.g., by alkaline phosphatase, β-galactosidase or β-glucuronidase), induces dioxetane decomposition and chemiluminescence. Alternatively, oxidation (e.g., by horseradish peroxidase, glucose, galactose oxidase or luciferase) of the dendritic polymer luminol, isoluminol, acridinium ester, acridinium sulfonylamide or luciferin substrate conjugates induces dioxetanone decomposition and chemiluminescence. The enzyme may be the target analyte in the sample, or may be a reporter molecule attached to a probe, an antigen or an antibody, or any member of a specific binding pair, to detect the presence of the other member of the specific binding pair. Generally there are a wide variety of assays and assay formats that exist, including immunoassay and array formats, which can make use of the dendritic polymer chemiluminescent substrate conjugates, all employing a visually detectable chemiluminescent signal to indicate the presence and/or concentration of a particular substance in a sample.

For example, to detect an enzyme in a sample, the sample can be contacted with dendritic polymer dioxetane conjugates bearing a group capable of being cleaved by the enzyme being detected. The enzyme cleaves the dioxetane's enzyme cleavable group to form a negatively charged substituent (e.g., an oxygen anion) bonded to the dioxetane. This negatively charged substituent in turn destabilizes the dioxetane, causing the dioxetane to decompose to form a chemiluminescent chromophore that emits light. It is this light emission that is detected as an indication of the presence of the enzyme. By measuring the intensity of luminescence, the concentration of the enzyme in the sample can be determined.

Alternatively, the sample can be contacted with dendritic polymer luminol, isoluminol, acridinium ester, acridinium sulfonylamide or luciferin conjugates capable of being oxidized by an oxidase label. The enzyme directly oxidizes the luminol, isoluminol, or luciferin, or indirectly oxidizes the acridinium ester, or acridinium sulfonylamide via hydrogen peroxide generation to an unstable peroxygenated intermediate that decomposes to emit light. The detected light emission indicates the presence of the oxidative enzyme. By measuring the intensity of luminescence, the concentration of the enzyme in the sample can also be determined.

It is well known that light quenching reactions occur if the peroxygenated chemiluminescent substrate decomposes in protic solvent such as water. Since assays generally take place in an aqueous environment, the light-quenching reactions may substantially reduce the chemiluminescence intensity observed. It is also known that water-soluble naturally-occurring and synthetic substances, that are generally macromolecular in size, can increase the light intensity of light-emitting fluorophores produced by the decomposition of chemiluminescent chemical compounds in aqueous and mixed, i.e., having an aqueous and a non-aqueous component, media. These enhancement agents improve the chemiluminescent signal of chemiluminescent substrates, apparently by providing a hydrophobic environment. Water, an unavoidable aspect of most assays due to the use of body fluids or biological agents, is a natural "quencher" of the chemiluminescence. The enhancement molecules apparently exclude water from the microenvironment in which the excited state emitter species reside, resulting in enhanced chemiluminescence. Other effects associated with the enhancer-chemiluminescent substrate could also contribute to the chemiluminescence enhancement. As discussed herein, enhancement agents, including water-soluble polymeric quaternary ammonium, phosphonium or sulfonium salts, and copolymers and/or mixtures thereof such as poly(vinylbenzyltrimethylammonium chloride), poly(vinyl) benzyltributylammonium chloride), and poly(vinylbenzyldimethylbenzylammonium chloride), which are disclosed in detail in U.S. Pat. No. 5,145,772, can be employed to increase the sensitivity of the assay.

As disclosed in U.S. Pat. No. 5,145,772, certain water soluble naturally-occurring and synthetic substances, generally macromolecular in nature, for example water soluble globular proteins that include hydrophobic regions: mammalian serum albumins such as bovine serum albumin (BSA) and human serum albumin (HSA), or water soluble polymeric quaternary ammonium, phosphonium or sulfonium salts: poly(vinylbenzyltrimethyl-ammonium chloride) (TMQ) or poly[vinylbenzyl(benzyldimethyl-ammonium chloride)] (BDMQ), permit the stabilization, and hence increase the light intensity, of light-emitting fluorophores produced by the decomposition of chemiluminescent chemical compounds in aqueous and mixed media. Such chemiluminescent compounds are enzymatically cleavable 1,2-dioxetanes; and mixtures of such chemiluminescent compounds with each other and with one or more auxiliary fluorophores, e.g., fluorescein, that accept energy from energy-emitting fluorophores produced by the decomposition of chemiluminescent compounds and in turn emit detectable energy. By virtue of the presence of effective amounts of an enhancer substance or substances the intensity of the light emitted in aqueous medium by the thus-stabilized fluorophores is increased significantly as compared to the intensity of light emitted by the same quantities of fluorophores in the absence of such enhancers.

An additional embodiment of the invention thus involves coupling enhancer molecules to the dendritic polymer, or modifying residual reactive surface groups on the dendritic polymer to contain enhancer sites. Once the dendritic polymer has been coupled to the chemiluminescent substrate precursor (as described above) at 10-90% of the reactive sites, the remaining reactive sites can be coupled to an enhancing agent or can be chemically modified to become an enhancing surface group. Or, if required by synthetic constraints, the chemiluminescent substrate precursors can be linked to reactive dendritic polymer sites after the enhancer macromolecules are coupled or after some of the dendritic reactive groups are modified. According to a first approach, the enhancer molecules, including, e.g., naturally-occurring macromolecular substances such as mammalian serum albumin, bovine serum albumin, human serum albumin, Protein A or mammalian IgG, can be coupled to dendritic polymer surface groups through methods well known in the art of peptide chemistry and bioconjugation (e.g., coupling of two agents through a streptavidin-biotin affinity). According to a second approach, the enhancer molecules include synthetic macromolecular substances with a reactive terminal group or a reactive linker each of which can be coupled to dendritic polymer surface groups. Possible synthetic enhancing substances, appropriately modified with a reactive linker or reactive terminal group, include poly(vinylarylquaternaryammonium) salts, poly-N-vinyloxazolidinones, polyvinylcarbamates, polyhydroxyacrylates and polyhydroxymethacrylates, quaternized amine-containing oligomers (e.g., Jeffamines), synthetic polypeptides (including polylysine and nylons), polyvinylalkylethers, polyacrylamides and polymethacrylamides, polyvinyl alcohols, poly 2-, 3-, or 4-vinylpyridinium salts, polyvinylalkylpyrrolidinones, polyvinylalkyloxazolidones, quaternized polyethyleneimines, poly-N-vinylamines, alkylated or arylated polyvinylpiperidine, polyacryloyl, polymethacryloyl, or 4-vinylbenzoylaminimides, and dendritic or hyperbranched analogues of the same. According to a third approach, reactive surfaces and/or interior groups on the dendritic polymer are chemically modified to provide enhancer moieties. Examples of dendritic polymer modification to enable chemiluminescence enhancement include peralkylation of terminal and/or interior amines, alkylation of terminal and/or interior amides, and reaction of terminal active esters with amino-linked ammonium, phosphonium or sulfonium salts. According to a fourth approach, a dendritic polymeric chemiluminescent substrate is attached to a dendritic polymeric enhancer through a linker to form a bridged dendrimer structure.

In addition, a water-solubilizing group (one or more in number), i.e., a substituent which enhances the solubility of the dioxetane in aqueous solution, including carboxylic acids or esters, alkyl- or aryloxides, alkyl-, aryl- or aralkylamides, alkyl- or arylurethanes, alkyl- or arylsulfonamides, alkyl- or arylsulfonic acids and quaternary amino salts; the most preferred solubilizing substituents are alkyl- or aryloxides, amides, and sulfonamides can be added to the chemiluminescent substrate or the dendrimer to enhance the substrate's solubility in the sample, which is generally aqueous in nature. Depending on whether the substituent selected is hydrogen or electron active, the identity may affect, in addition to solubility, half-life ($T_{1/2}$) of the decomposition reaction, chemiluminescent yield, and signal to noise ratio (S/N). Suitable substituents and their impact on the dioxetane chemiluminescence, are discussed in connection with phenoxy-substituted dioxetanes and disclosed and claimed in U.S. Pat. No. 5,330,900, the entire contents of which are incorporated by reference herein.

The above-described dendritic polymer chemiluminescent substrates can be used in any reporter molecule-based assay with an acceptable environment. Examples of such assays include immunoassays to detect antibodies or antigens, e.g., enzyme assays and nucleic acid assays to detect, e.g., viruses (e.g., HTLV III or cytomegalovirus), or bacteria (e.g., *E. Coli*), and certain cell functions (e.g., receptor binding sites).

To detect a substance such as an antibody, an antigen or a nucleic acid, the enzyme capable of cleaving the enzyme cleavable group of the dioxetane, or the enzyme capable of oxidizing the luminol, isoluminol, acridinium ester, acridinium sulfonylamide or luciferin, is preferably bonded to a substance having a specific affinity for the detectable substance (i.e., a substance that binds specifically to the detectable substance), e.g., the antigen, the antibody or the nucleic acid probe. In addition to the direct attachment of an enzyme, a ligand can be attached to the substance having a specific affinity to the detectable substance. The ligand is then detected with a high affinity ligand-binding agent labeled with an enzyme capable of cleaving the enzyme cleavable group of the dioxetane, or oxidizing luminol, isoluminol, acridinium ester, acridinium sulfonamide or luciferin. Conventional methods, e.g., carbodiimide coupling, are used to bond the enzyme to the specific affinity substance; bonding is preferably through an amide linkage.

In general, assays are performed as follows. In one example, a sample suspected of containing a detectable substance is contacted with a buffered solution containing an enzyme bonded to a substance having a specific affinity for the detectable substance. The resulting solution is incubated to allow the detectable substance to bind to the specific affinity portion of the specific affinity-enzyme complex. Excess specific affinity-enzyme complex is washed away, and a dendritic chemiluminescent substrate having a group cleavable by the enzyme label of the specific affinity-enzyme complex, or having a group oxidizable by the enzyme label of the specific affinity-enzyme complex, is added. In a second example, a sample suspected of containing a detectable substance is contacted with a buffered solution containing a ligand bonded to a substance having specific affinity for the detectable substance. The resulting solution is incubated to allow the detectable substance to bind to specific affinity-ligand complex. Excess specific affinity-ligand complex is washed away, and an enzyme-labeled ligand binding agent is added and incubated to allow the enzyme-labeled ligand binding agent to bind to the ligand. Excess enzyme-labeled ligand binding agent is then washed away, and a dendritic chemiluminescent substrate having a group cleavable by the enzyme portion of the enzyme-labeled ligand binding agent is added. In both examples, the enzyme-activated peroxygenated intermediate decomposes and luminesces. Luminescence is detected using, e.g., a cuvette, or a light-sensitive film in a camera luminometer, or CCD, or a photoelectric cell or photomultiplier tube, to measure the presence and concentration of the detectable substance in the same.

In another type of assay, substances with specific affinity for detectable substances in biological samples are arrayed on solid supports in spacially well-defined patterns. Solid supports such as glass, plastic, silicon, polymer in planar or nonplanar, porous or nonporous, solid or beaded formats are used. The detectable substances in biological samples may be nucleic acids or proteins. The biological sample containing the detectable substance(s) is contacted with the solid phase array and incubated under conditions optimized for the binding of the detectable substance(s). In one case, the detectable substance(s) are prelabeled with detectable ligands by chemical or enzymatic means and subsequently detected with enzyme-labeled ligand binding agents. In another case, the bound unlabeled substance is detected with a second enzyme- or ligand-labeled substance that also has affinity for the bound detectable substance form the biological sample. This binding of the labeled substance can be prior to capture of the detectable substance on the array or after capture. If the detection involves a ligand-labeled substance, an additional incubation with an enzyme-labeled ligand binding agent is required. Suitable washes are performed between incubations as required. The final step in all cases will be the addition of a dendritic chemiluminescent substrate having a group cleavable by the enzyme portion of the enzyme-labeled detection agent, or having a group oxidizable by the enzyme portion of the specific enzyme labeled complex. The enzyme-activated peroxygenated intermediate decomposes and luminesces. Luminescence is detected using a charge-coupled camera (CCD), film or other light sensitive imaging device and the intensity of the light measured in specific areas is determined.

The following examples further illustrate the invention but are not to be construed as a limitation to the scope of the invention.

EXAMPLES

Synthesis of Activated Ester Dendrimers

A solution of 100 mg carboxylate-terminated dendrimer (e.g., Starburst PAMAM dendrimer, adjusted to pH 7) and N-hydroxysuccinimide (1.0 eq per carboxylate end group) in 20 ml dry 1,2-dimethoxymethane is stirred at 0° C. A coupling agent, e.g., dicyclohexylcarbodiimide (DCC, 1.0 eq per carboxylic acid end group) or 1-(3-dimethylaminopropyl)-3-ethylcarbodiimide hydrochloride (EDCl, 1.0 eq per carboxylic acid end group), is added at 0° C. and the solution is stored in the refrigerator overnight. The urea byproduct is removed by filtration or by an aqueous wash (EDCl byproduct), the organic solvent is evaporated, and the crude product is purified by chromatography.

Synthesis of Dendritic Polymer Enol Ether Conjugates Having the General Structure Depicted in FIG. 4A or 4E To a stirred solution of 100 mg activated ester-terminated dendrimer in 15 ml $CH_2Cl_2$ with 0.1 ml triethylamine is added enol ether with a linker terminated with a primary or secondary amine (1.01 eq enol ether per activated ester end group; e.g., activator=N-hydroxysuccinimide ester). The reaction is stirred overnight at room temperature, diluted with $CH_2Cl_2$ to 75 ml and washed with water (3×30 ml) and saturated $Na_2CO_3$ (3×30 ml). The organic layer is dried over $Na_2SO_4$ and stripped of solvent to yield the dendritic enol ether conjugate depicted in FIG. 4A or 4E.

Synthesis of Dendritic Polymer Enol Ether Conjugates Having the General Structure Depicted in FIG. 4B or 4F To a stirred solution of 100 mg amino-terminated dendrimer (e.g., Starburst PAMAM dendrimer or polypropylenimine tetrahexacontaamine dendrimer) in 15 ml $CH_2Cl_2$ with 0.1 ml triethylamine is added enol ether with a linker terminated with an activated ester (1.01 eq enol ether per $NH_2$ end group; e.g., activator=N-hydroxysuccinimide ester). The reaction is stirred overnight at room temperature, diluted with $CH_2Cl_2$ to 75 ml and washed with water (3×30 ml) and saturated $Na_2CO_3$ (3×30 ml). The organic layer is dried over $Na_2SO_4$ and stripped of solvent to yield the dendritic enol ether conjugate depicted in FIG. 4B or 4F.

Synthesis of Dendritic Polymer Enol Ether Conjugates Having the General Structure Depicted in FIG. 4C or 4D Synthesis Scheme 1:

To a stirred solution of 100 mg amino-terminated dendrimer (e.g., Starburst PAMAM dendrimer or polypropylenimine tetrahexacontaamine dendrimer) in 15 ml $CH_2Cl_2$ with 0.1 ml triethylamine is added enol ether with a linker terminated with a halide (e.g., I or Br) or sulfonic ester (e.g., mesylate, tosylate, brosylate). The reaction is stirred overnight at room temperature, diluted with $CH_2Cl_2$ to 75 ml and washed with water (3×30 ml) and saturated $Na_2 CO_3$ (3×30 ml). The organic layer is dried over $Na_2SO_4$ and stripped of solvent to yield the dendritic enol ether conjugate depicted in FIG. 4C or 4D.

Synthesis Scheme 2:

To a stirred solution of 100 mg bromo- or mesylate- or tosylate- or brosylate-terminated dendrimer (e.g., Starburst PAMAM-OH modified with a leaving group) in 15 ml $CH_2Cl_2$ with 0.1 ml triethylamine is added enol ether with a linker terminated with an amine or hydroxyl group. The reaction is stirred overnight at room temperature, diluted with $CH_2Cl_2$ to 75 ml and washed with water (3×30 ml) and saturated $Na_2 CO_3$ (3×30 ml). The organic layer is dried over $Na_2SO_4$ and stripped of solvent to yield the dendritic enol ether conjugate depicted in FIG. 4C or 4D.

Synthesis of Dioxetane-Polyammonium and Dioxetane-Polyvinylpiperdinium Dendrimer A solution of 100 mg carboxylate-terminated dendrimer (e.g., Starburst PAMAM dendrimer, adjusted to pH 7), an enol ether with an amino-terminated linker (0.5 eq per carboxylate end group) and amino-terminated polymer (0.5 eq per carboxylate end group, e.g., polyethylenimine, poly-N-vinylamine or polyvinylpiperidine) in 20 ml dry 1,2-dimethoxymethane is stirred at 0° C. A coupling agent, e.g., dicyclohexylcarbodiimide (DCC, 1.0 eq per carboxylic acid end group) or 1-(3-dimethylaminopropyl)-3-ethylcarbodiimide hydrochloride (EDCl, 1.0 eq per carboxylic acid end group), is added at 0° C. and the solution is stored in the refrigerator overnight. The urea byproduct is removed by filtration or by an aqueous wash (EDCl urea byproduct), the organic solvent is evaporated, and the crude enol ether-enhancer dendrimer is purified by chromatography. The amine sites are peralkylated to ammonium groups by reaction with an alkylhalide (e.g., iodomethane to permethylate or butylbromide to perbutylate), and the enol either is oxygenated to the dioxetane as described below to complete the synthesis of a dendritic dioxetane-polyammonium or dendritic dioxetane-polyvinylpiperidinium substrate.

Synthesis of Biotinylated Starburst Dendrimers

A 0.1 mol solution of amino-terminated dendrimer (e.g., Starburst PAMAM dendrimer or Starburst PEI dendrimer, adjusted to pH 7) in tris, hepes, phosphate, carbonate or borate buffer is reacted with N-hydroxysuccinimidobiotin (0.1-10 mol) at ambient temperature 12-48 hrs. The biotinylated dendrimer is purified by dialysis, size-exclusion chromatography (SEC) or ion-exchange chromatography.

Synthesis of Avidin- or Streptavidin-Conjugated Starburst Dendrimers

A 0.1 mol solution of amino-terminated dendrimer (e.g., Starburst PAMAM dendrimer or Starburst PEI dendrimer, adjusted to pH 7) in DMF is reacted with succinyl-avidin (Sigma) or succinyl-streptavidin in the presence of a coupling agent (e.g., dicyclohexylcarbodiimide (DCC) or 1-(3-dimethylaminopropyl)-3-ethylcarbodiimide hydrochloride (EDCl). The reaction is stirred at ambient temperature for 2-24 hours. The avidin-conjugated dendrimer is purified by ultrafiltration or Sephadex column chromatography.

Alternatively, to a stirred solution of 100 mg carboxylate-terminated PAMAM dendrimer in 15 ml deionized water is added avidin or streptavidin and the coupling agent 1-(3-dimethylaminopropyl)-3-ethylcarbodiimide hydrochloride (EDCl). The reaction is stirred at room temperature for 8-24 hrs while maintaining the solution at or near pH 5. The reaction solution is ultrafiltered or eluted through a Sephadex column to yield the avidin- or streptavidin-conjugated dendrimer.

Synthesis of Isoluminol-Bovine Serum Albumin Dendrimer

An aqueous pH 7 solution of 100 mg avidin-conjugated dendrimer is added to a solution of biotinylated aminobutyl-ethylisoluminol (ABEI) and biotinylated bovine serum albumin (BSA) (present in a 1:1 molar ratio) and stirred at ambient temperature for 1-24 hrs. The solution is ultrafiltered to remove unreacted biotinylated agents to yield dendritic isoluminol-BSA substrate.

Synthesis of Dendritic Polymer Dioxetane Conjugates

A 10% MeOH/CHCl$_3$ solution (50 ml) of dendrimer-enol ether conjugate (250 mg), with tetraphenylporphine (TPP, 10 mg in 5 ml CHCl$_3$), is cooled in an ice bath while sparging with oxygen through a Pasteur pipette for 5 minutes. The oxygen flow is continued while the solution is irradiated with a 400 watt sodium vapor lamp, which is filtered with a 3.0 ml thickness of DuPont Kapton film. When the photooxidation is complete, the reaction is stripped of solvents, dissolved in water and preparatively chromatographed on a one inch PLRP-S column (Polymer Laboratories) using an acetonitrile/water gradient. The product peak is shaved on the front and back, collecting only the middle cut. The eluent is freeze-dried to obtain the dendritic dioxetane product as a white solid.

Synthesis of Dendritic Isoluminol Conjugates

To a stirred solution of 100 mg bromo- or mesylate- or tosylate- or brosylate-terminated dendrimer (e.g., PAMAM-OH modified with a leaving group) in 15 ml CH$_2$Cl$_2$ with 0.1 ml triethylamine is added N-(4-aminobutyl)-N-ethylisoluminol (ABEI). The reaction is stirred overnight at room temperature, diluted with CH$_2$Cl$_2$ to 75 ml and washed with water (3×30 ml) and saturated Na$_2$CO$_3$ (3×30 ml). The organic layer is dried over Na$_2$SO$_4$ and stripped of solvent to yield the dendritic isoluminol conjugate.

Synthesis of Dendritic Isoluminol Conjugates

To a stirred solution of 100 mg activated ester-terminated dendrimer (e.g., PAMAM-CONHS) in 15 ml CH$_2$Cl$_2$ with 0.1 ml triethylamine is added N-(4-aminobutyl)-N-ethylisoluminol (ABEI, 1.01 eq isoluminol per activated ester end group). The reaction is stirred overnight at room temperature, diluted with CH$_2$Cl$_2$ to 75 ml and washed with water (3×30 ml) and saturated Na$_2$CO$_3$ (3×30 ml). The organic layer is dried over Na$_2$SO$_4$ and stripped of solvent to yield the dendritic isoluminol conjugate.

Synthesis of Dendritic Acridinium Ester Conjugates

A solution of 100 mg amine-terminated dendrimer (e.g., PAMAM-NH$_2$ or PEI Starburst Dendrimer), and 1 mol equivalent of acridinium ester with an activated carboxylate-terminated linker in 20 ml dry 1,2-dimethoxymethane is stirred at 0° C. A coupling agent, e.g., dicyclohexylcarbodiimide (DCC, 1.0 eq per carboxylic acid end group) or 1-(3-dimethylaminopropyl)-3-ethylcarbodiimide hydrochloride (EDCl, 1.0 eq per carboxylic acid end group), is added at 0° C. and the solution is stored in the refrigerator overnight. The urea byproduct is removed by filtration or by an aqueous wash (EDCl urea byproduct), the organic solvent is evaporated, and the crude dendritic acridinium ester is purified by chromatography.

Synthesis of Dendritic Acridinium Sulfonylamide Conjugates

A solution of 100 mg amine-terminated dendrimer (e.g., PAMAM-NH$_2$ or PEI Starburst Dendrimer), and 1 mol equivalent of acridinium sulfonylamide with an activated carboxylate-terminated linker in 20 ml dry 1,2-dimethoxymethane is stirred at 0° C. A coupling agent, e.g., dicyclohexylcarbodiimide (DCC, 1.0 eq per carboxylic acid end group) or 1-(3-dimethylaminopropyl)-3-ethylcarbodiimide hydrochloride (EDCl, 1.0 eq per carboxylic acid end group), is added at 0° C. and the solution is stored in the refrigerator overnight. The urea byproduct is removed by filtration or by an aqueous wash (EDCl urea byproduct), the organic solvent is evaporated, and the crude dendritic acridinium sulfonylamide is purified by chromatography.

Determination of the Chemiluminescence Half-Life of Dephosphorylated Dioxetane

A 1 mL aliquot of dendritic polymer dioxetane conjugate (0.004 mM) is equilibrated to 30° C. in 0.1M diethanolamine, 1 mM MgCl$_2$, pH 10. Alkaline phosphatase (at final concentration of $1.05 \times 10^{-9}$ M) is added to the test tube and the chemiluminescent signal kinetics is measured in a Turner TD-20E luminometer for 10 to 20 minutes. The half-life is calculated from the plot of log RLU versus time. The chemiluminescence half-life is also determined in the presence of Sapphire-II™ enhancer (in 0.1M diethanolamine, 1 mM MgCl$_2$, 10% polyvinylbenzyltributyl ammonium chloride qt 1 mg/mL).

Determination of the Peak Light Intensity of Dephosphorylated Dioxetanes

A 0.5 mL aliquot of dendritic polymer dioxetane conjugate (0.004 mM) is equilibrated to 30° C. in 0.1M diethanolamine, 1 mM MgCl$_2$, pH 10. Alkaline phosphatase (final concentration of $1.05 \times 10^{-9}$M) is added to the tube and the chemiluminescent signal is measured in a Turner TD-20E luminometer for 10 to 20 minutes. The peak light intensity is recorded. The peak light intensity is also determined in the presence of Sapphire-II™ enhancer (in 0.1M diethanolamine, 1 mM MgCl$_2$, 10% polyvinylbenzyltributyl ammonium chloride qt 1 mg/mL).

A dendritic polymer dioxetane conjugate of the invention may be employed in a TSH assay as follows:

Materials
  Mouse monoclonal anti-TSH-β antibody can be used to coat ⅛ inch beads for analyte capture. Mouse monoclonal anti-TSH antibody can be conjugated with alkaline phosphatase and used as a detection antibody.
  TSH can be obtained from Calbiochem, Catalog No. 609396, and BSA (type V—fatty acid free) can be obtained from Sigma, Catalog No. A6003.
  The buffer solution used for the analyte and conjugate can contain 0.1M Tris-HCl, 1 mM MgCl$_2$, and 2% by weight BSA (pH=7.5) The substrate buffer solution can contain 0.1M Tris, 0.1 mM MgCl$_2$, 0.1% by weight BSA (pH=9.5), and a dendritic polymer dioxetane conjugate as the chemiluminescent compound. (50 μg/ml).

Protocol
  15 μl of a TSH-containing analyte solution is mixed with 135 μl of conjugate antibody solution. Two ⅛ inch beads coated as described above are added to the solution and incubated for 2 hours at 23° C. The beads are then washed four times with 0.1M Tris (pH=7.5) and transferred to a reaction tube. 200 μl of the same chemiluminescent compound used in the substrate buffer solution described above is added to the tube. Following an incubation period of 20 minutes, light emission is recorded as ten second counts using a Berthold Clinilumat Luminescence Analyzer.

In addition, a dendritic polymer dioxetane conjugate of the invention may be employed in an assay for human IgG, for hCG, for serum alkaline phosphatase, for alpha feto protein, for TSH, or for any of the substances assayed for and in accordance with the protocols disclosed in U.S. Pat. No. 4,978,614, the entire contents of which are incorporated herein by reference.

The dendritic polymer dioxetane conjugates of the invention may be employed in a nucleic acid hybridization assay as follows:

A sample of cerebrospinal fluid (CSF) suspected of containing cytomegalovirus is collected and placed on a nitrocellulose membrane. The sample is then chemically treated with urea or guanidinium isothiocyanate to break the cell walls and to degrade all cellular components except the viral DNA. The strands of the viral DNA thus produced are separated and attached to the nitrocellulose filter. A DNA probe specific to the viral DNA and labeled with alkaline phosphatase is then applied to the filter; the probe hybridizes with the complementary viral DNA strands. After hybridization, the filter is washed with an aqueous buffer solution containing 0.2 M NaCl and 0.1 mM Tris-HCl (pH=8.10) to remove excess probe molecules. A phosphate-containing dendritic polymer dioxetane conjugate is added and the resulting luminescence from the enzymatic degradation of the dioxetane is measured in a luminometer or detected with photographic film.

The dendritic polymer dioxetane conjugates of the invention may also be employed in any of the DNA probe assays disclosed in U.S. Pat. No. 4,978,614, the entire contents of which are incorporated by reference herein.

The above discussion of this invention is directed primarily to preferred embodiments and practices thereof. It will be readily apparent to those skilled in the art that further changes and modifications in the actual implementation of the concepts described herein can easily be made without departing from the spirit and scope of the invention.

What is claimed is:

1. A kit for conducting an assay to determine the presence or concentration of an analyte in a sample, wherein the kit comprises:
  a dendrimer comprising at least one enzymatically active chemiluminescent substrate moiety, wherein the substrate moiety comprises a dioxetane having an enzyme labile group; and
  an enzyme capable of cleaving the enzyme labile group of the dioxetane to produce a peroxygenated intermediate that decomposes to produce light;
  wherein the dendrimer comprising at least one enzymatically active chemiluminescent substrate moiety is represented by the formula selected from the group consisting of

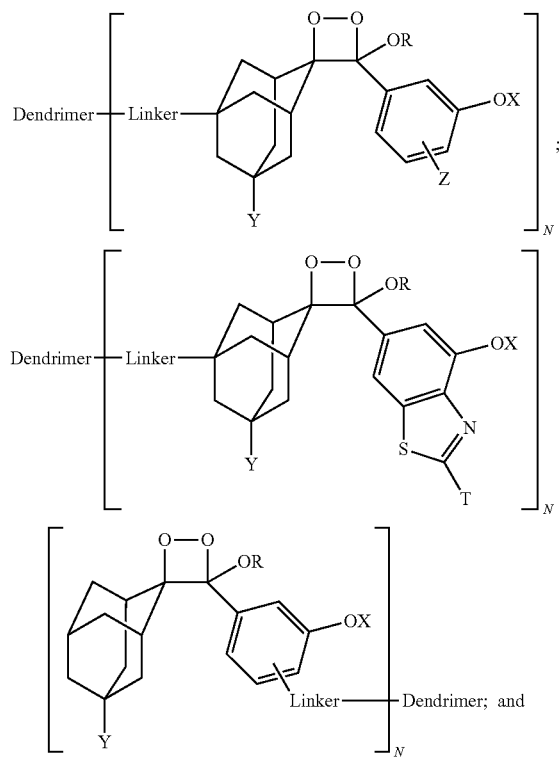

-continued

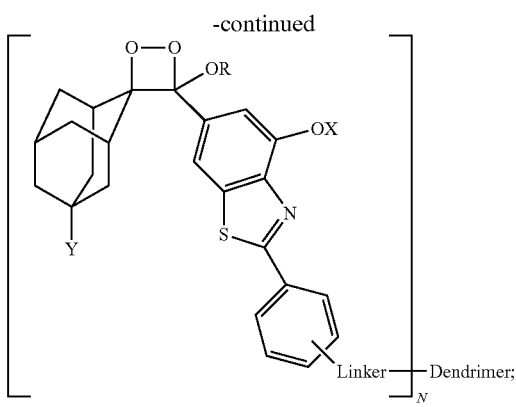

wherein

"Linker" represents a linker moiety;

"Dendrimer" represents a dendrimer moiety resulting from the reaction of a surface functional group on the dendrimer with a functional group on the linker moiety, wherein said dendrimer moiety comprises a chemiluminescent enhancement substance selected from the group consisting of water soluble polymeric quaternary ammonium salts, water soluble polymeric quaternary phosphonium salts, water soluble polymeric quaternary sulfonium salts, and mixtures thereof;

N is a positive integer representing the number of chemiluminescent substrates conjugated to the dendrimer moiety;

Y is H, a hydroxyl group, a halogen, an unsubstituted alkyl group, a hydroxy substituted alkyl group, a halogen substituted alkyl group, a phenyl group, a halogenated phenyl group, an alkoxy substituted phenyl group, an alkoxy phenoxy group, a hydroxy alkoxy group, a cyano group, an amide group, an alkoxy group or a carboxyl group;

R is a $C_1$-$C_{12}$ alkyl, mono-, di-, or trihaloalkyl, an aryl or an aralkyl;

X is an enzyme-labile group selected from the group consisting of a phosphate, galactoside, acetate, 1-phospho-2,3-diacylglyceride, 1-thio-D-glucoside, adenosine triphosphate, adenosine diphosphate, adenosine monophosphate, adenosine, α-D-glucoside, β-D-glucoside, β-D-glucuronide, β-D-mannoside, β-D-mannoside, β-D-fructofuranoside, β-glucosiduronate, 5-acetamido-3,5-dideoxy-α-D-glycero-D-galacto-2-nonulopyranoside, alkoxy derivatives of 5-acetamido-3,5-dideoxy-α-D-glycero-D-galacto-2-nonulopyranoside, p-toluenesulfonyl-L-arginine ester, and p-toluenesulfonyl-L-arginine amide;

Z is a halo, alkoxy or alkyl group; and

T is H, an electron donating group, an electron withdrawing group, or an organic linker group which may be attached to an ancillary fluorophore or to a biological moiety.

2. The kit of claim 1, wherein the assay is an immunoassay and the enzyme is complexed with an agent capable of binding to the analyte.

3. The kit of claim 1, wherein the assay is a DNA probe assay, the kit further comprising a membrane on which the assay can be conducted.

4. The kit of claim 3, wherein the enzyme is complexed with an agent and wherein the agent can form a complex with the analyte.

5. The kit of claim 1, wherein the assay is a DNA sequence analysis assay and the kit further comprises a membrane on which said sequence analysis assay can be conducted.

6. The kit of claim 5, wherein the enzyme is complexed with an agent permitting attachment of the enzyme to the DNA to be sequenced in the assay.

7. The kit of claim 1, wherein the enzyme is capable of oxidizing the chemiluminescent substrate to produce the peroxygenated intermediate.

8. A method for detecting the presence of an analyte in a sample comprising:

forming an enzyme complex between an enzyme and a substance capable of binding to the analyte;

adding the enzyme complex to the sample;

allowing the enzyme complex to bind with analyte present in the sample;

removing the enzyme complex which did not bind with the analyte prior to the measuring step;

adding a chemiluminescent delivery system to the sample; and measuring chemiluminescent emissions from the sample;

wherein the chemiluminescent delivery system comprises a dendrimer and at least one enzymatically active chemiluminescent substrate which is conjugated to the dendrimer, wherein the substrate comprises a dioxetane having an enzyme labile group which is capable of being cleaved by the enzyme to produce a peroxygenated intermediate, wherein the amount of chemiluminescent emissions measured indicates the presence and/or the concentration of the analyte in the sample, and wherein the chemical delivery system is represented by the formula selected from the group consisting of

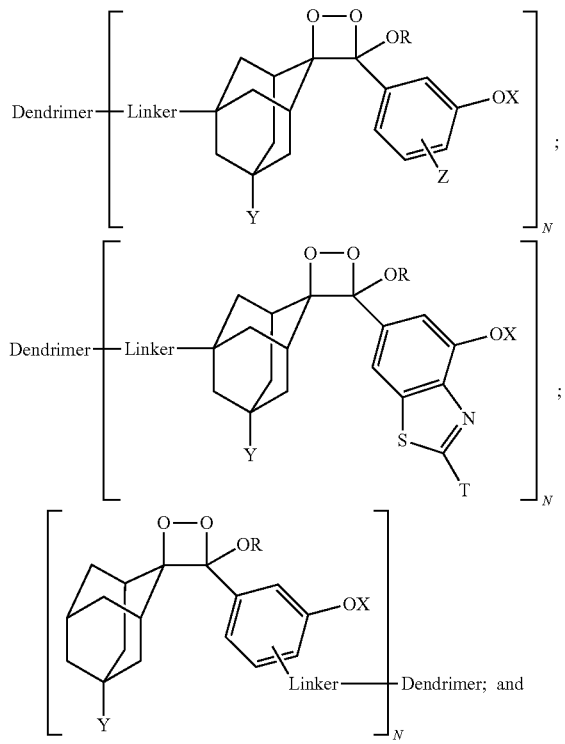

-continued

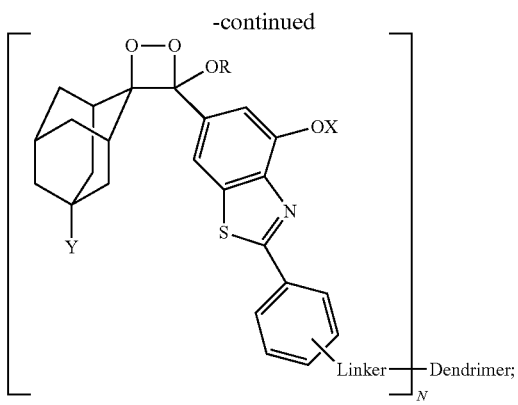

wherein

"Linker" represents a linker moiety;

"Dendrimer" represents a dendrimer moiety resulting from the reaction of a surface functional group on the dendrimer with a functional group on the linker moiety, wherein said dendrimer moiety comprises a chemiluminescent enhancement substance selected from the group consisting of water soluble polymeric quaternary ammonium salts, water soluble polymeric quaternary phosphonium salts, water soluble polymeric quaternary sulfonium salts, and mixtures thereof;

N is a positive integer representing the number of chemiluminescent substrates conjugated to the dendrimer moiety;

Y is H, a hydroxyl group, a halogen, an unsubstituted alkyl group, a hydroxy substituted alkyl group, a halogen substituted alkyl group, a phenyl group, a halogenated phenyl group, an alkoxy substituted phenyl group, an alkoxy phenoxy group, a hydroxy alkoxy group, a cyano group, an amide group, an alkoxy group or a carboxyl group;

R is a $C_1$-$C_{12}$ alkyl, mono-, di-, or trihaloalkyl, an aryl or an aralkyl;

X is an enzyme-labile group selected from the group consisting of a phosphate, galactoside, acetate, 1-phospho-2,3-diacylglyceride, 1-thio-D-glucoside, adenosine triphosphate, adenosine diphosphate, adenosine monophosphate, adenosine, α-D-glucoside, β-D-glucoside, β-D-glucuronide, β-D-mannoside, β-D-mannoside, β-D-fructofuranoside, β-glucosiduronate, 5-acetamido-3,5-dideoxy-α-D-glycero-D-galacto-2-nonulopyranoside, alkoxy derivatives of 5-acetamido-3,5-dideoxy-α-D-glycero-D-galacto-2-nonulopyranoside, p-toluenesulfonyl-L-arginine ester, and p-toluenesulfonyl-L-arginine amide;

Z is a halo, alkoxy or alkyl group; and

T is H, an electron donating group, an electron withdrawing group, or an organic linker group which may be attached to an ancillary fluorophore or to a biological moiety.

9. The method of claim 8, wherein the substance capable of binding to the analyte is an antigen, an antibody or a nucleic acid probe.

10. The method of claim 8, wherein the assay is conducted on a solid support.

11. The method of claim 10, wherein the presence of an analyte is detected in a plurality of samples arranged in an array on the solid support.

12. The method of claim 10, further comprising binding the analyte to the solid support.

13. The method of claim 8, wherein the enzyme is selected from the group consisting of glycosidases, esterases, proteases, oxidases, peptidases and phosphatases.

14. The kit of claim 1, wherein, the linker moiety is represented by the formula

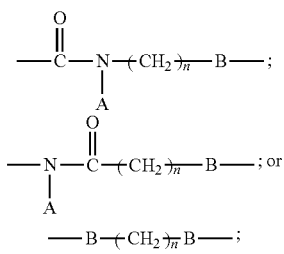

wherein,
n is a positive integer;
A is H, alkyl, trihaloalkyl or aryl and
B is independently NA, NC(O)A, O, S or $CH_2$.

15. The method of claim 8, wherein, the linker moiety is represented by the formula

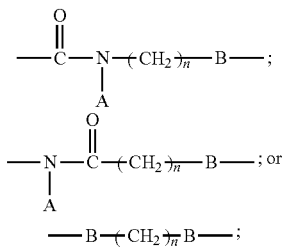

wherein,
n is a positive integer;
A is H, alkyl, trihaloalkyl or aryl and
B is independently NA, NC(O)A, O, S or $CH_2$.

* * * * *